United States Patent
Lu et al.

(10) Patent No.: US 7,115,598 B2
(45) Date of Patent: Oct. 3, 2006

(54) SUBSTITUTED 1,4-DIAZEPINES AND USES THEREOF

(75) Inventors: Tianbao Lu, Churchville, PA (US); Karen L. Milkiewicz, Exton, PA (US); Pierre Raboisson, Mechelen (BE); Maxwell David Cummings, Wayne, PA (US); Raul R. Calvo, Royersford, PA (US); Daniel J. Parks, Downingtown, PA (US); Louis V. Lafrance, III, West Chester, PA (US); Juan Jose Marugan Sanchez, Downingtown, PA (US); Joan Gushue, Conshohocken, PA (US); Kristi Leonard, West Chester, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 163 days.

(21) Appl. No.: 10/829,040

(22) Filed: Apr. 21, 2004

(65) Prior Publication Data

US 2004/0220179 A1    Nov. 4, 2004

Related U.S. Application Data

(60) Provisional application No. 60/465,264, filed on Apr. 25, 2003.

(51) Int. Cl.
*C07D 243/14* (2006.01)
*A61K 31/55* (2006.01)

(52) U.S. Cl. ............... 514/221; 540/506; 540/509
(58) Field of Classification Search ............... 540/506, 540/509; 514/221
See application file for complete search history.

(56) References Cited

OTHER PUBLICATIONS

Chen et al., *Proc. Natl. Acad. Sci. USA*, 95:195-200 (1998).
Keating and Armstrong, *J. Am. Chem. Soc.*, 118:2574-2583 (1996).
Kussie et al., *Science*, 274:948-953 (1996).
Bottger et al., *J. Mol Biol.*, 269:744-756 (1997).
International Search Report dated Oct. 20, 2005 for International Appln. No. PCT/US04/12240.
Hulme et al. Improved Procedure for the Solution Phase Preparation of 1,4-Benzodiazepine-2,5-dione Libraries via Armstrong's Convertible Isonitrile and the Ugi Reaction, J. Org. Chem, 1998, vol. 63, pp. 8021-8023.

*Primary Examiner*—Bruck Kifle
(74) *Attorney, Agent, or Firm*—Laura Donnelly

(57) ABSTRACT

The present invention is directed to novel 1,4-diazepines, pharmaceutical compositions thereof, and the use thereof as inhibitors of HDM2-p53 interactions. Compounds have Formula I:

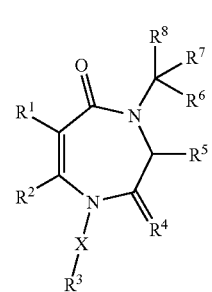

or a solvate, hydrate or pharmaceutically acceptable salt thereof; wherein:

$R^1$, $R^2$, $R^9$, $R^{10}$, $R_a$, $R^d$ and M are defined herein;

X is a bivalent radical of: an alkane, a cycloalkane, an optionally-substituted arene, an optionally-substituted heteroarene, an optionally-substituted arylalkane or an optionally-substituted heteroarylalkane; and $R^3$ is —$CO_2R^d$, —$CO_2M$, —OH, —$NHR^d$, —$SO_2R^d$, —$NHCONHR^d$, optionally-substituted amidino or optionally-substituted guanidino;

or $R^3$—X— is hydrogen or an electron pair;

$R^4$ is oxygen or —$NR^9R^{10}$;

$R^5$ is cycloalkyl, aryl, heteroaryl, cycloalkylalkyl, aralkyl, heteroarylalkyl, or a saturated or partially unsaturated heterocycle, each of which is optionally substituted; and $R^6$, $R^7$ and $R^8$ are independently hydrogen, alkyl, cycloalkyl, aryl, heteroaryl, a saturated or partially unsaturated heterocycle, cycloalkylalkyl, aralkyl or heteroarylalkyl, each of which is optionally substituted; or $R^6$ and $R^7$, together with the carbon atom to which they are attached form a 3- to 7-membered carbocyclic ring optionally substituted 1 to 3 times with $R^a$.

62 Claims, No Drawings

SUBSTITUTED 1,4-DIAZEPINES AND USES THEREOF

CROSS REFERENCE TO RELATED APPLICATIONS

This application claims priority to U.S. Provisional Application Ser. No. 60/465,264, filed Apr. 25, 2003.

BACKGROUND OF THE INVENTION

1. Field of the Invention

The present invention is in the area of novel 1,4-diazepines and salts thereof, their syntheses, and their use as inhibitors of MDM2 and HDM2 oncoproteins.

2. Related Art

This invention relates to compounds that bind to the human protein HDM2 and interfere with its interaction with other proteins, especially the tumor suppressor protein p53. HDM2 is the expression product of hdm2, an oncogene that is overexpressed in a variety of cancers, especially soft tissue sarcomas (Momand, J., et al., Nucl. Acids Res. 26:3453–3459 (1998)).

p53 is a transcription factor that plays a pivotal role in the regulation of the balance between cell proliferation and cell growth arrest/apoptosis. Under normal conditions, the half-life of p53 is very short, and consequently the level of p53 in cells is low. However, in response to cellular DNA damage, cellular stress, or other factors, levels of p53 increase. This increase in p53 levels in turn increases the transcription of a number of genes which induces the cell to either arrest growth or undergo apoptosis (i.e., controlled cell death). The function of p53 is to prevent the uncontrolled proliferation of cells and thus protect the organism from the development of cancer (for a review, see Levine, A. J., Cell 88:323–331 (1997)).

p53 is a latent and short-lived transcription factor which is induced by, and is an integration point for, a range of cellular stresses including DNA damage, UV damage, spindle damage, hypoxia, inflammatory cytokines, viral infection, activated oncogenes, and ribonucleotide depletion. Activation of p53 mediates a change in the balance of gene expression such that expression of many genes involved in proliferation is repressed while a range of genes involved in growth arrest (such as p21WAF1 and GADD45), repair (such as p53RE) and apoptosis (such as Bax, Killer/DR5 and PIGs) is activated. The biological outcome of p53 activation (whether permanent or transient growth arrest or apoptosis) is dependent on several factors including the type and strength of the inducing stress, and the type of cell or tissue.

p53 and MDM2 exist in a negative regulatory feedback loop in which p53 stimulates transcription of the mdm2 gene while MDM2 binds to p53 and targets it for degradation by the 26S proteasome. The key element in the p53 induction process is disruption of the p53-MDM2 complex which permits p53 to accumulate in the nucleus. This mechanism appears to be common to all of the pathways by which p53 becomes activated, although recent evidence has indicated that there is considerable variation in the molecular events by which this is actually achieved.

Inactivation of the p53 tumor suppressor is a frequent event in human neoplasia. The inactivation can occur by mutation of the p53 gene or through binding to viral or cellular oncogene proteins, such as the SV40 large T antigen and MDM2. While the mechanism through which wild-type p53 suppresses tumor cell growth is as yet poorly defined, it is clear that one key feature of the growth suppression is the property of p53 to act as a transcription factor (Farmer, G., et al., Nature 358:83–86 (1992); Funk, W. D. et al., Mol. Cell. Biol. 12: 2866–2871 (1992); Kern, S. E., et al., Science 256:827–830 (1992)). Currently, considerable effort is being made to identify growth control genes that are regulated by p53 binding to sequence elements near or within these genes. A number of such genes have been identified. In cases such as the muscle creatine kinase gene (Weintraub, H., et al., Proc. Natl. Acad. Sci. U.S.A., 88:4570–4571 (1991); Zambetti, G. P., et al., Genes Dev. 6:1143–1152 (1992)) and a GLN retroviral element (Zauberman, A., et al., EMBO J. 12:2799–2808 (1993)), the role these genes might play in the suppression of growth control is unclear. Yet there are other examples, namely mdm2 (Barak, Y., et al. EMBO J. 12:461–468 (1993); Wu, X., et al., Genes Dev. 7:1126–1132 (1993)) GADD 45 (Kastan, M. B., et al., Cell 71:587–597 (1992)) and WAF1 or CIP1 (El-Beiry, W. S., et al., Cell 75:817–825 (1993); Harper, J. W., et al., Cell 75:805–816 (1993)), where their involvement in the regulation of cell growth is better understood.

mdm2, a known oncogene, was originally found on mouse double minute chromosomes (Cahilly-Snyder., L., et al., Somatic Cell Mol. Genet. 13:235–244 (1987)). Its protein product was subsequently found to form a complex with p53, which was first observed in a rat fibroblast cell line (Clone 6) previously transfected with a temperature sensitive mouse p53 gene (Michalovitz, D., et al., Cell 62:671–680 (1990)). The rat cell line grew well at 37° C. but exhibited a GI arrest when shifted down to 32° C., which was entirely consistent with an observed temperature dependent switch in p53 conformation and activity. However, the p53-MDM2 complex was only observed in abundance at 32° C., at which temperature p53 was predominantly in a functional or "wild-type" form (Barak, Y. et al., EMBO J. 11:2115–2121 (1992) and Momand, J., et al., Cell 69:1237–1245 (1992)). By shifting the rat cell line down to 32° C. and blocking de novo protein synthesis it was shown that only "wild-type" p53 induced expression of the mdm2 gene, thereby accounting for the differential abundance of the complex in terms of p53 transcriptional activity (Barak, Y., et al., EMBO J. 12:461–468 (1993)). The explanation was further developed by the identification of a DNA binding site for wild-type p53 within the first intron of the mdm2 gene (Wu, X., et al., Genes Dev. 7:1126–1132 (1993)). Reporter constructs employing this p53 DNA binding site revealed that they were inactivated when wild-type p53 was co-expressed with MDM2.

This inhibition of the transcriptional activity of p53 may be caused by MDM2 blocking the activation domain of p53 and/or the DNA binding site. Consequently, it was proposed that mdm2 expression is autoregulated, via the inhibitory effect of MDM2 protein on the transcriptional activity of wild-type p53. This p53-mdm2 autoregulatory feedback loop provided a novel insight as to how cell growth might be regulated by p53. Up to a third of human sarcomas are considered to overcome p53-regulated growth control by amplification of the hdm2 gene (the human homologue of mdm2) (Oliner, J. D., et al., Nature 358:80–83 (1992)). Hence, the interaction between p53 and HDM2 represents a key potential therapeutic target. One mechanism by which MDM2 can promote tumorogenesis is by its inhibitory action on p53. The tumor suppressor functions of p53 control a pivotal checkpoint in the control of cell cycling (reviewed in Levine, A. J., Cell 88:323–331 (1997)). p53 is a transcription factor for a number of proteins that cause cell cycle arrest or cell death by apoptosis. The level and transcriptional activity of p53 are increased by damage to cellular DNA. The MDM2 protein inhibits p53 function by binding to an amphipathic N-terminal helix of p53, abrogating the interaction of p53 with other proteins and its transactivation activity. The interaction with MDM2 also targets p53 for ubiquitin dependent protein degradation. MDM2 exhibits p53 independent effects on cell cycling as well, possibly by direct interaction with some of the downstream effectors such as pRB and EF2 (Reviewed in Zhang, R. and Wang, H., Cur. Pharm. Des. 6:393–416 (2000)).

Blocking HDM2 from binding p53 would be therapeutically useful in restoring cell cycle control to cells that overexpress HDM2 as a front line cancer treatment. More generally, inhibition of HDM2 may increase the effectiveness of chemotherapy and radiation in p53 normal cancers by enhancing apoptosis and growth arrest signaling pathways.

A need continues to exist for potent, small molecules that inhibit the interactions between HDM2 and p53.

SUMMARY OF THE INVENTION

A first aspect of the present invention is directed to novel compounds of Formula I.

A second aspect of the present invention is directed to pharmaceutical compositions comprising at least one compound of Formula I, or a salt thereof, and one or more pharmaceutically acceptable excipients.

A third aspect of the present invention is directed to a method of inhibiting the binding of a protein encoded by hdm2 to p53 protein, comprising contacting p53 or one or more proteins encoded by mdm2, with one or more compounds of Formula I.

A fourth aspect of the invention is directed to a method of inducing apoptosis, comprising contacting an animal with a composition comprising a pharmaceutically effective amount of at least one compound of Formula I, or a salt thereof, and one or more pharmaceutically-acceptable excipients.

A fifth aspect of the present invention is directed to a method of treating cancer. The method comprises contacting an animal with (a) a pharmaceutically effective amount of an antineoplastic agent and (b) a pharmaceutically effective amount of at least one compound of Formula I, or a salt thereof, and one or more pharmaceutically-acceptable excipients.

A sixth aspect of the present invention is directed to a method of treating cancer, comprising contacting an animal with a composition comprising (a) a pharmaceutically effective amount of at least one compound of Formula I, or a salt thereof, (b) one or more agents that induce or cause DNA damage, and (c) one or more pharmaceutically-acceptable excipients.

A seventh aspect of the present invention is directed to a method of synthesizing compounds of Formula I.

DETAILED DESCRIPTION OF THE PREFERRED EMBODIMENTS

A novel class of small molecules that bind to HDM2 and/or MDM2 has now been discovered. By interfering with HDM2-p53 or MDM2-p53 interactions, these compounds increase the intracellular concentration of p53. These small molecules, therefore, have therapeutic utility in sensitizing tumor cells for chemotherapy. In tumor types particularly sensitive to an increase in functional p53, compounds of this type will be sufficient to induce apoptosis. Compounds of the present invention are also useful in treating tumor types in which HDM2 or MDM2 is overexpressed.

Compounds of the present invention include compounds of Formula I:

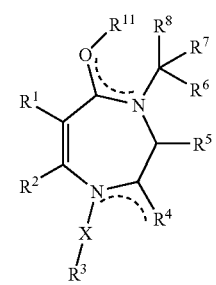

or a solvate, hydrate or pharmaceutically acceptable salt thereof, wherein:

$R^1$ and $R^2$ are independently hydrogen, alkyl, alkenyl, alkynyl, optionally-substituted cycloalkyl, optionally-substituted cycloalkylalkyl, optionally-substituted aryl, optionally-substituted aralkyl, optionally-substituted heteroaryl, optionally-substituted heteroaralkyl, alkoxy, optionally-substituted aryloxy, optionally-substituted heteroaryloxy, cyano, amino, alkanoylamino, nitro, hydroxy, carboxy, or alkoxycarbonyl; or $R^1$ and $R_2$, together with the two carbon atoms to which they are attached, form a 5- to 10-membered non-aromatic or a 6- to 10-membered aromatic carbocyclic ring, or a 5- to 10-membered aromatic or non-aromatic ring wherein 1 or 2 of the ring atoms are heteroatoms, wherein each of the rings is optionally substituted 1–4 times with $R^a$, wherein each occurrence of $R^a$ is independently hydrogen, halo, optionally-substituted alkyl, optionally-substituted alkenyl, optionally-substituted alkynyl, optionally-substituted cycloalkyl, optionally-substituted aryl, optionally-substituted aralkyl, optionally-substituted heteroaryl, optionally-substituted heteroaralkyl, alkoxy, optionally-substituted aryloxy, optionally-substituted heteroaryloxy, cyano, optionally-substituted amino, carbamoyl, alkylaminocarbonyl, dialkylaminocarbonyl, alkanoylamino, nitro, hydroxy, carboxy, alkoxycarbonyl or acyl, optionally-substituted alkyl thiol, optionally-substituted trifluorothio, optionally-substituted hydroxy imine alkyl;

X is a bivalent radical of: an optionally-substituted alkane, a optionally-substituted cycloalkane, an optionally-substituted arene, an optionally-substituted heteroarene, an optionally-substituted arylalkane or an optionally-substituted heteroarylalkane, optionally-substituted amine; and $R^3$ is —$CO_2R^d$, —$CO_2M$, —OH, —$OR^d$, —$NHR^d$, —$NR^dR^d$, —$SO_2R^d$, —$NHCONHR^d$, —$NHCONR^dR^d$, —$CH_2R^d$, optionally-substituted amidino or optionally-substituted guanidino, where $R^d$ is hydrogen, alkyl, optionally-substituted alkoxy, optionally-substituted cycloalkyl or optionally-substituted, saturated or partially unsaturated heterocycle, and M is a cation or H;

or $R^3$—X— is hydrogen or an electron pair;

$R^4$ is oxygen, two hydrogen groups, or —$NR^9R^{10}$ where $R^9$ and $R^{10}$ are independently hydrogen, optionally-substituted alkyl, cycloalkyl, optionally-substituted aryl, optionally-substituted heteroaryl, optionally-substituted aralkyl, optionally-substituted heteroaralkyl, carboxyalkyl, alkoxycarbonyl, alkoxycarbonylalkyl, aminocarbonyl, aminocarbonylalkyl, alkylaminocarbonyl or alkylaminocarbonylalkyl, alkoxy;

or $R^3$ and $R^4$, together with the two carbon atoms to which they are attached, form a 5- to 10-membered non-aromatic or a 6- to 10-membered aromatic carbocyclic ring, or a 5- to 10-membered aromatic or non-aromatic ring wherein 1 or 2 of the ring atoms are heteroatoms, wherein each of the rings is optionally substituted 1–4 times with $R^a$, where $R^a$ is defined as above;

$R^5$ is cycloalkyl, aryl, heteroaryl, cycloalkylalkyl, aralkyl, heteroarylalkyl, or a saturated or partially unsaturated heterocycle, each of which is optionally substituted;

$R^6$, $R^7$ and $R^8$ are independently hydrogen, alkyl, cycloalkyl, aryl, heteroaryl, a saturated or partially unsaturated heterocycle, cycloalkylalkyl, aralkyl or heteroarylalkyl, each of which is optionally substituted; or $R^6$ and $R^7$, together with the carbon atom to which they are attached form a 3- to 7-membered carbocyclic ring optionally substituted 1 to 3 times with $R^a$, where $R^a$ is defined as above;

$R^{11}$ is alkyl, cycloalkyl, aryl, heteroaryl, a saturated or partially unsaturated heterocycle, cycloalkylalkyl, aralkyl or heteroarylalkyl, each of which is optionally substituted.

Useful values of $R^1$ and $R^2$ include hydrogen, $C_{1-6}$ alkyl, $C_{2-6}$ alkenyl, $C_{2-6}$ alkynyl, optionally-substituted $C_{3-8}$ cycloalkyl, optionally-substituted $C_{3-8}$ cycloalkyl($C_{1-4}$) alkyl, optionally-substituted phenyl, optionally-substituted naphthyl, optionally-substituted phenyl($C_{1-6}$) alkyl, optionally-substituted naphthyl($C_{1-6}$) alkyl, optionally-substituted heteroaryl having 5 to 7 ring atoms of which 1 or 2 are heteroatoms, optionally-substituted heteroaryl($C_{1-6}$) alkyl in which the heteroaryl portion has 5 to 7 ring atoms of which 1 or 2 are heteroatoms, $C_{1-6}$ alkoxy, optionally-substituted phenoxy, optionally-substituted benzyloxy, optionally-substituted naphthoxy, optionally-substituted heteroaryloxy in which the heteroaryl portion has 5 to 7 ring atoms of which 1 or 2 are heteroatoms, cyano, amino, ($C_{1-6}$ alkanoyl)amino, nitro, hydroxy, carboxy or ($C_{1-6}$ alkoxy)carbonyl. Particularly useful values of $R^1$ and $R^2$ include hydrogen, optionally-substituted phenyl, optionally-substituted benzyl, optionally-substituted cyclopentyl, optionally-substituted cyclohexyl, optionally-substituted $C_{3-8}$ cycloalkyl($C_{1-4}$) alkyl and $C_{1-6}$ alkyl.

Also useful is when $R^1$ and $R^2$, together with the two carbon atoms to which they are attached, form an optionally-substituted 5- to 7-membered ring, aromatic or non-aromatic, wherein 0, 1 or 2 of the ring atoms are heteroatoms. Particularly useful rings formed in this fashion include optionally-substituted benzene and optionally-substituted pyridine.

When $R^1$ and $R^2$, together with the two carbon atoms to which they are attached, form a ring, the ring is optionally substituted one or more times, preferably 1 or 2 times, with $R^a$.

Useful values of $R^a$ include hydrogen, halo, $C_{1-6}$ alkyl, $C_{2-6}$ alkenyl, $C_{2-6}$ alkynyl, $C_{3-8}$ cycloalkyl, optionally-substituted $C_{6-10}$ aryl, optionally-substituted ($C_{6-10}$ aryl)$C_{1-6}$ alkyl, optionally-substituted thio, optionally-substituted 5- to 7-membered heteroaryl, optionally-substituted heteroaryl ($C_{1-6}$) alkyl in which the heteroaryl portion has 5 to 7 ring atoms of which 1 or 2 are heteroatoms, $C_{1-6}$ alkoxy, optionally-substituted ($C_{6-10}$ aryl)oxy, optionally-substituted heteroaryloxy in which the heteroaryl portion has 5 to 7 ring atoms of which 1 or 2 are heteroatoms, cyano, amino, carbamoyl, ($C_{1-6}$ alkyl)aminocarbonyl, di-($C_{1-6}$ alkyl)aminocarbonyl, ($C_{1-6}$ alkanoyl)amino, nitro, hydroxy, carboxy, ($C_{1-6}$ alkoxy)carbonyl and $C_{1-6}$ acyl.

Particularly useful values of X include a bivalent radical of: a $C_{1-6}$ alkane, an optionally-substituted $C_{6-10}$ arene, an optionally-substituted 5- to 7-membered heteroarene wherein 1 or 2 ring atoms are heteroatoms, an optionally-substituted ($C_{6-10}$ aryl)$C_{1-6}$ alkane, and an optionally-substituted heteroaryl($C_{1-6}$) alkane in which the heteroaryl portion contains 5 to 7 ring atoms and wherein 1 or 2 of the ring atoms are heteroatoms. Preferred values of X include a bivalent radical of: a $C_{1-6}$ alkane, optionally-substituted benzene, optionally-substituted furan, optionally-substituted thiophene, optionally-substituted pyrrole and optionally-substituted pyridine. More preferred X include a bivalent radical of: methane, ethane, n-propane, n-butane, n-pentane, n-hexane, benzene and furan. When X is a bivalent radical of an alkane: preferably the alkane has at least 3 carbon atoms; preferably the alkane is unbranched; and preferably X is an α,ω-bivalent radical.

Particularly useful values of $R^3$ include —$CO_2R^d$ and —$CO_2M$, where $R^d$ is hydrogen, $C_{1-6}$ alkyl or optionally-substituted $C_{3-8}$ cycloalkyl, and M is a cation. Preferred values of $R^3$ include —$CO_2R^d$ and —$CO_2M$, where $R^d$ is hydrogen or $C_{1-6}$ alkyl, and M is a cation. More preferred $R^3$ includes —$CO_2R^d$, where $R^d$ is hydrogen or $C_{1-4}$ alkyl. Most preferred is —COOH.

Particularly useful values of $R^5$ include $C_{3-8}$ cycloalkyl, $C_{6-10}$ aryl, 5- to 7-membered heteroaryl wherein 1 or 2 of the ring atoms are heteroatoms, ($C_{3-8}$ cycloalkyl)alkyl, ($C_{6-10}$ aryl)alkyl, (heteroaryl)alkyl in which the heteroaryl portion contains 5 to 7 ring atoms and wherein 1 or 2 of the ring atoms are heteroatoms, and 5- to 7-membered saturated or partially unsaturated heterocycle wherein 1 or 2 of the ring atoms are heteroatoms, in which each of the preceding groups is optionally substituted. A preferred value of $R^5$ is optionally-substituted phenyl. When $R^5$ is phenyl it is substituted preferably once in the 4-position or twice in the 3- and 4-positions, and preferably by halo, trifluoromethyl, trifluoromethoxy, nitro and/or amino. More preferred $R^5$ include 4-chlorophenyl, 4-trifluoromethylphenyl, 4-trifluoromethoxyphenyl, 4-chloro-3-nitrophenyl, 3-amino-4-chlorophenyl and 3-bromophenyl.

Particularly useful values of $R^6$ include $C_{3-8}$ cycloalkyl, $C_{6-10}$ aryl, 5- to 7-membered heteroaryl wherein 1 or 2 of the ring atoms are heteroatoms, ($C_{3-8}$ cycloalkyl)alkyl, ($C_{6-10}$ aryl)alkyl, (heteroaryl)alkyl in which the heteroaryl portion contains 5 to 7 ring atoms and wherein 1 or 2 of the ring atoms are heteroatoms, and 5- to 7-membered saturated or partially unsaturated heterocycle wherein 1 or 2 of the ring atoms are heteroatoms, in which each of the preceding groups is optionally substituted. Preferred values of $R^6$ include optionally-substituted phenyl, optionally-substituted benzyl, optionally-substituted pyridyl and optionally-substituted naphthyl. More preferred is optionally-substituted phenyl. When $R^6$ is substituted phenyl or substituted benzyl it is substituted preferably once in the p-position or twice in the m- and p-positions, or twice in the o- and p-position, and preferably by halo, nitro and/or amino. More preferred $R^6$ include phenyl, 4-chlorophenyl, 3,4-dichlorophenyl, 2-amino-4-chlorophenyl, 2-amino-4-chloro-5-fluorophenyl, 3-amino-4-chlorophenyl and 4-chloro-3-nitrophenyl. Preferred $R^6$ also include p-chlorobenzyl and 4-methyl-1-naphthyl.

Particularly useful values of $R^7$ include hydrogen, $C_{1-6}$ alkyl, $C_{3-8}$ cycloalkyl and ($C_{3-8}$ cycloalkyl)alkyl. Preferred values of $R^7$ include hydrogen, $C_{1-6}$ alkyl and $C_{3-6}$ cycloalkyl. More preferred $R^7$ include hydrogen, methyl and cyclopropyl.

Particularly useful values of $R^8$ include hydrogen and $C_{1-6}$ alkyl. Preferred values of $R^8$ include hydrogen, methyl and ethyl. More preferred is hydrogen.

Particularly useful values of $R^9$ include hydrogen, $C_{1-6}$ alkyl, $C_{3-6}$ cycloalkyl, hydroxy($C_{1-6}$) alkyl, amino($C_{1-6}$) alkyl, carboxy($C_{1-6}$) alkyl, ($C_{1-6}$ alkoxy)carbonyl, ($C_{1-6}$ alkoxy)carbonyl($C_{1-6}$) alkyl, carbamoyl, carbamoyl($C_{1-6}$) alkyl, ($C_{1-6}$ alkylamino)carbonyl and ($C_{1-6}$ alkylamino)carbonyl($C_{1-6}$) alkyl. Preferred values of $R^9$ include hydrogen, $C_{1-6}$ alkyl, hydroxy($C_{1-6}$) alkyl, amino($C_{1-6}$) alkyl and carbamoyl($C_{1-6}$) alkyl. More preferred values of $R^9$ include hydrogen, methyl, 2-hydroxyethyl, 3-hydroxypropyl, 2-aminoethyl, carbamoylmethyl and carbamoylethyl.

Particularly useful values of $R^{10}$ include hydrogen and $C_{1-6}$ alkyl. Preferred values of $R^{10}$ include hydrogen, methyl and ethyl. More preferred is hydrogen.

In one preferred embodiment, compounds of the present invention are compounds of Formula II:

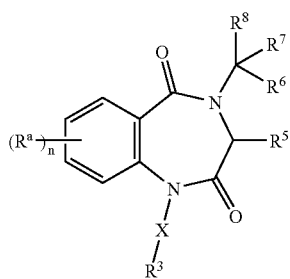

or a solvate, hydrate or pharmaceutically acceptable salt thereof, wherein $R^a$, $R^3$, X, $R^5$, $R^6$, $R^7$ and $R^8$ are defined as for compounds of Formula I, and n is 0, 1, 2, 3 or 4.

In this embodiment, particularly useful and preferred values of $R^3$, X, $R^5$, $R^6$, $R^7$ and $R^8$ are as described for compounds of Formula I.

In this embodiment, particularly useful values of $R^a$ include halo, $C_{1-6}$ alkyl, $C_{2-6}$ alkenyl, $C_{2-6}$ alkynyl, cyano, $C_{3-8}$ cycloalkyl, hydroxy, $C_{1-6}$ alkoxy, carboxy, ($C_{1-6}$ alkoxy)carbonyl, $C_{1-6}$ acyl, carbamoyl, ($C_{1-6}$ alkyl)aminocarbonyl, amino and nitro. Preferred values of $R^a$ include halo, $C_{2-6}$ alkynyl, carboxy, ($C_{1-6}$ alkoxy)carbonyl, $C_{1-6}$ acyl and carbamoyl. More preferred values of $R^a$ include iodo, bromo, chloro, ethynyl, acetyl, methoxycarbonyl, carboxy and carbamoyl.

In this embodiment, particularly useful values of n include 0, 1 and 2. Preferred values of n include 1 and 2. More preferred is 1. When n is 1, $R^a$ occurs preferably at the 7- or the 8-position, more preferably at the 7-position. When n is 2, $R^a$ occurs preferably at the 7- and 8-positions.

A preferred group of compounds are compounds of Formula II, wherein:

each instance of $R^a$ is independently halo, $C_{1-6}$ alkyl, $C_{2-6}$ alkenyl, $C_{2-6}$ alkynyl, cyano, $C_{3-8}$ cycloalkyl, hydroxy, $C_{1-6}$ alkoxy, carboxy, ($C_{1-6}$ alkoxy)carbonyl, $C_{1-6}$ acyl, carbamoyl, ($C_{1-6}$ alkyl)aminocarbonyl, amino or nitro, alkylthio;

n is 0, 1 or 2; when n is 1, $R^a$ occurs at the 7- or 8-position; when n is 2, $R^a$ occurs at the 7- and 8-positions;

X is a bivalent radical of: a $C_{1-6}$ alkane, an optionally-substituted $C_{6-10}$ arene, an optionally-substituted 5- to 7-membered heteroarene wherein 1 or 2 ring atoms are heteroatoms, an optionally-substituted ($C_{6-10}$ aryl)$C_{1-6}$ alkane, or an optionally-substituted heteroaryl($C_{1-6}$) alkane in which the heteroaryl portion contains 5 to 7 ring atoms and wherein 1 or 2 of the ring atoms are heteroatoms;

$R^3$ is $—CO_2R^d$ or $—CO_2M$, where $R^d$ is hydrogen, $C_{1-6}$ alkyl or optionally-substituted $C_{3-8}$ cycloalkyl, and M is a cation;

$R^5$ is $C_{3-8}$ cycloalkyl, $C_{6-10}$ aryl, 5- to 7-membered heteroaryl wherein 1 or 2 of the ring atoms are heteroatoms, ($C_{3-8}$ cycloalkyl)alkyl, ($C_{6-10}$ aryl)alkyl, (heteroaryl)alkyl in which the heteroaryl portion contains 5 to 7 ring atoms and wherein 1 or 2 of the ring atoms are heteroatoms, or 5- to 7-membered saturated or partially unsaturated heterocycle wherein 1 or 2 of the ring atoms are heteroatoms, in which each of the preceding groups is optionally substituted;

$R^6$ is $C_{3-8}$ cycloalkyl, $C_{6-10}$ aryl, 5- to 7-membered heteroaryl wherein 1 or 2 of the ring atoms are heteroatoms, ($C_{3-8}$ cycloalkyl)alkyl, ($C_{6-10}$ aryl)alkyl, (heteroaryl)alkyl in which the heteroaryl portion contains 5 to 7 ring atoms and wherein 1 or 2 of the ring atoms are heteroatoms, or 5- to 7-membered saturated or partially unsaturated heterocycle wherein 1 or 2 of the ring atoms are heteroatoms, in which each of the preceding groups is optionally substituted;

$R^7$ is hydrogen, $C_{1-6}$ alkyl, $C_{3-8}$ cycloalkyl or ($C_{3-8}$ cycloalkyl)alkyl; and $R^8$ is hydrogen or $C_{1-6}$ alkyl.

A more preferred group of compounds are compounds of Formula II, wherein:

each instance of $R^a$ is independently halo, $C_{2-6}$ alkynyl, carboxy, ($C_{1-6}$ alkoxy)carbonyl, $C_{1-6}$ acyl or carbamoyl;

n is 1 or 2; when n is 1, $R^a$ occurs at the 7-position; when n is 2, $R^a$ occurs at the 7- and 8-positions;

X is a bivalent radical of a $C_{1-6}$ alkane, optionally-substituted benzene, optionally-substituted furan, optionally-substituted thiophene, optionally-substituted pyrrole or optionally-substituted pyridine;

$R_3$ is $—CO_2R^d$ or $—CO_2M$, where $R^d$ is hydrogen or $C_{1-6}$ alkyl, and M is a cation;

$R^5$ is optionally-substituted phenyl;

$R_6$ is optionally-substituted phenyl, optionally-substituted benzyl, optionally-substituted pyridyl or optionally-substituted naphthyl;

$R^7$ is hydrogen, $C_{1-6}$ alkyl or $C_{3-6}$ cycloalkyl; and $R^8$ is hydrogen.

In one preferred embodiment, compounds of the present invention are compounds of Formula III:

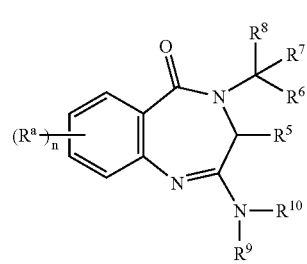

or a solvate, hydrate or pharmaceutically acceptable salt thereof, wherein $R^a$, $R^5$, $R^6$, $R^7$, $R^8$, $R^9$ and $R^{10}$ are defined as for compounds of Formula I, and n is 0, 1, 2, 3 or 4.

Those skilled in the art will recognize that compounds of Formula I when $R^4$ is $—NR^9R^{10}$ are amidines which exist in an equilibrium between tautomeric forms when at least one of $R^9$ and $R^{10}$ is hydrogen. While Formula III illustrates only one form, the invention is intended to encompass both tautomers.

In this embodiment, particularly useful and preferred values of $R^5$, $R^6$, $R^7$, $R^8$, $R^9$ and $R^{10}$ are as described for compounds of Formula I.

In this embodiment, particularly useful values of $R^a$ include halo, $C_{1-6}$ alkyl, $C_{2-6}$ alkenyl, $C_{2-6}$ alkynyl, cyano, $C_{3-8}$ cycloalkyl, hydroxy, $C_{1-6}$ alkoxy, carboxy, ($C_{1-6}$ alkoxy)carbonyl, $C_{1-6}$ acyl, carbamoyl, ($C_{1-6}$ alkyl)aminocarbonyl, amino, alkylthio, and nitro. Preferred values of $R^a$ include halo, $C_{2-6}$ alkynyl, carboxy, ($C_{1-6}$ alkoxy)carbonyl, $C_{1-6}$ acyl and carbamoyl. More preferred values of $R^a$ include iodo, chloro, ethynyl, acetyl, methoxycarbonyl, carboxy and carbamoyl.

In this embodiment, particularly useful values of n include 0, 1 and 2. Preferred values of n include 1 and 2. More preferred is 1. When n is 1, $R^a$ occurs preferably at the 7- or the 8-position, more preferably at the 7-position. When n is 2, $R^a$ occurs preferably at the 7- and 8-positions.

A preferred group of compounds are compounds of Formula III, wherein:

each instance of $R^a$ is independently halo, $C_{1-6}$ alkyl, $C_{2-6}$ alkenyl, $C_{2-6}$ alkynyl, cyano, $C_{3-8}$ cycloalkyl, hydroxy, $C_{1-6}$ alkoxy, carboxy, ($C_{1-6}$ alkoxy)carbonyl, $C_{1-6}$ acyl, carbamoyl, ($C_{1-6}$ alkyl)aminocarbonyl, amino, alkylthio, or nitro;

n is 0, 1 or 2; when n is 1, $R^a$ occurs at the 7- or 8-position; when n is 2, $R^a$ occurs at the 7- and 8-positions;

$R^5$ is $C_{3-8}$ cycloalkyl, $C_{6-10}$ aryl, 5- to 7-membered heteroaryl wherein 1 or 2 of the ring atoms are heteroatoms, ($C_{3-8}$ cycloalkyl)alkyl, ($C_{6-10}$ aryl)alkyl, (heteroaryl)alkyl in which the heteroaryl portion contains 5 to 7 ring atoms and wherein 1 or 2 of the ring atoms are heteroatoms, or 5- to 7-membered saturated or partially unsaturated heterocycle wherein 1 or 2 of the ring atoms are heteroatoms, in which each of the preceding groups is optionally substituted;

$R^6$ is $C_{3-8}$ cycloalkyl, $C_{6-10}$ aryl, 5- to 7-membered heteroaryl wherein 1 or 2 of the ring atoms are heteroatoms, ($C_{3-8}$ cycloalkyl)alkyl, ($C_{6-10}$ aryl)alkyl, (heteroaryl)alkyl in which the heteroaryl portion contains 5 to 7 ring atoms and wherein 1 or 2 of the ring atoms are heteroatoms, or 5- to 7-membered saturated or partially unsaturated heterocycle wherein 1 or 2 of the ring atoms are heteroatoms, in which each of the preceding groups is optionally substituted;

$R^7$ is hydrogen, $C_{1-6}$ alkyl, $C_{3-8}$ cycloalkyl or ($C_{3-8}$ cycloalkyl)alkyl;

$R^8$ is hydrogen or $C_{1-6}$ alkyl;

$R^9$ is hydrogen, $C_{1-6}$ alkyl, $C_{3-6}$ cycloalkyl, hydroxy($C_{1-6}$) alkyl, amino($C_{1-6}$) alkyl, carboxy($C_{1-6}$) alkyl, ($C_{1-6}$ alkoxy)carbonyl, ($C_{1-6}$ alkoxy)carbonyl($C_{1-6}$) alkyl, carbamoyl, carbamoyl($C_{1-6}$) alkyl, ($C_{1-6}$ alkylamino)carbonyl or ($C_{1-6}$ alkylamino)carbonyl($C_{1-6}$) alkyl; and $R^{10}$ is hydrogen or $C_{1-6}$ alkyl.

A more preferred group of compounds are compounds of Formula III, wherein:

each instance of $R^a$ is independently halo, $C_{2-6}$ alkynyl, carboxy, ($C_{1-6}$ alkoxy)carbonyl, $C_{1-6}$ acyl or carbamoyl;

n is 1 or 2; when n is 1, $R^a$ occurs at the 7-position; when n is 2, $R^a$ occurs at the 7- and 8-positions;

$R^5$ is optionally-substituted phenyl;

$R_6$ is optionally-substituted phenyl, optionally-substituted pyridyl, optionally-substituted benzyl or optionally-substituted naphthyl;

$R^7$ is hydrogen, $C_{1-6}$ alkyl or $C_{3-6}$ cycloalkyl;

$R^8$ is hydrogen;

$R^9$ is hydrogen, $C_{1-6}$ alkyl, hydroxy($C_{1-6}$) alkyl, amino ($C_{1-6}$) alkyl or carbamoyl($C_{1-6}$) alkyl; and $R^{10}$ is hydrogen.

A second aspect of the present invention is directed to pharmaceutical compositions comprising a) at least one compound of Formula I or a pharmaceutically acceptable salt thereof; and b) one or more pharmaceutically-acceptable excipients.

Preferably, the pharmaceutical composition is sterile.

A third aspect of the present invention is directed to a method of inhibiting the binding of a protein encoded by mdm2 to p53 protein, comprising contacting p53 or one or more proteins encoded by mdm2 with one or more compounds of Formula I, wherein $R^1$–$R^8$ and X are defined as above.

A fourth aspect of the invention is directed to a method of inducing apoptosis, comprising contacting an animal with a composition comprising a pharmaceutically effective amount of at least one compound of Formula I, or a salt thereof, wherein $R^1$–$R^8$ and X are defined as above, and optionally one or more pharmaceutically-acceptable excipients.

A fifth aspect of the present invention is directed to a method of treating cancer, comprising contacting an animal with (a) a pharmaceutically effective amount of an antineoplastic agent, and (b) a pharmaceutically effective amount of at least one compound of Formula I, or a salt thereof, wherein $R^1$–$R^{11}$ and X are defined as above, and optionally one or more pharmaceutically-acceptable excipients, in combination with (a), (b), or (a) and (b).

A sixth aspect of the present invention is directed to a method of treating cancer, comprising contacting an animal with a composition comprising (a) a pharmaceutically effective amount of at least one compound of Formula I, or a salt thereof, wherein $R^1$–$R^{11}$ and X are defined as above, (b) one or more agents that induce or cause DNA damage, and optionally (c) one or more pharmaceutically-acceptable excipients.

A seventh aspect of the present invention is directed to a method of making compounds of Formula I.

Compounds within the scope of the invention are described in the Examples. Examples of preferred compounds include: 5-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-yl}-pentanoic acid; 5-{(3S)-3-(4-Chlorophenyl)-4-[(R)-1-(4-chlorophenyl)-ethyl]-7-ethynyl-2,5-dioxo-2,3,4,5-tetrahydro-benzo[e][1,4]diazepin-1-yl}-pentanoic acid; 5-[4-[(R)-1-(4-Chlorophenyl)-ethyl]-7-iodo-2,5-dioxo-(3S)-3-(4-trifluoromethyl-phenyl)-2,3,4,5-tetrahydro-benzo[e][1,4]diazepin-1-yl]-pentanoic acid; 5-[4-[(R)-1-(4-Chlorophenyl)-ethyl]-7-iodo-2,5-dioxo-(3S)-3-(4-trifluoromethoxy-phenyl)-2,3,4,5-tetrahydro-benzo[e][1,4]diazepin-1-yl]-pentanoic acid; 6-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-yl}-hexanoic acid; 7-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-yl}-heptanoic acid; 4-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-ylmethyl}-benzoic acid; 4-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-yl}-butyric acid; 3-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-yl}-propionic acid; 5-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-ylmethyl}-furan-2-carboxylic acid; 5-{(3S)-8-Chloro-3-(4-chloro-phenyl)-4-[(R)-1-(4-chlorophenyl)-ethyl]-7-iodo-2,5-dioxo-2,3,4,5-tetrahydro-benzo[e][1,4]diazepin-1-yl}-pentanoic acid; 5-{3-(4-Chlorophenyl)-4-[(4-chlorophenyl)-cyclopropylmethyl]-7-iodo-2,5-dioxo-2,3,4,5-tetrahydro-benzo[e][1,4]diazepin-1-yl}-pentanoic acid; 5-{3-(4-Chlorophenyl)-4-[1-(3,4-dichlorophenyl)-ethyl]-7-iodo-2,5-dioxo-2,3,4,5-tetrahydro-benzo[e][1,4]diazepin-1-yl}-pentanoic acid; 5-[4-[1(3Amino-4-chlorophenyl)-ethyl]-3-(4-chlorophenyl)-7-iodo-2,5-dioxo-2,3,4,5-tetrahydro-benzo[e][1,4]diazepin-1-yl]-pentanoic acid; 5-[4-[1-(4-Chloro-3-nitro-phenyl)-ethyl]-3-(4-chlorophenyl)-7-iodo-2,5-dioxo-2,3,4,5-tetrahydro-benzo[e][1,4]diazepin-1-yl]-pentanoic acid; 5-{3-(4-Chlorophenyl)-7-iodo-4-[1-(4-methyl-naphthalen-1-yl)-ethyl]-2,5-dioxo-2,3,4,5-tetrahydro-benzo[e][1,4]diazepin-1-yl}-pentanoic acid; 5-[4-(4-Chlorobenzyl)-3-(4-chlorophenyl)-7-iodo-2,5-dioxo-2,3,4,5-tetrahydro-benzo[e][1,4]diazepin-1-yl]-pentanoic acid; 5-{3-(4-Chlorophenyl)-4-[2-(4-chlorophenyl)-1-methyl-ethyl]-7-iodo-2,5-dioxo-2,3,4,5-tetrahydro-benzo[e][1,4]diazepin-1-yl}-pentanoic acid; 5-{(3S)-3-(3-Bromo-phenyl)-4-[(R)-1-(4-chloro-phenyl)-ethyl]-7-iodo-2,5-dioxo-2,3,4,5-tetrahydro-benzo[e][1,4]diazepin-1-yl}-pentanoic acid; [4-Benzyl-3-(4-chlorophenyl)-7-iodo-2,5-dioxo-2,3,4,5-tetrahydro-benzo[e][1,4]diazepin-1-yl]-acetic acid; 5-{(3S)-3-(4-Chloro-3-nitro-phenyl)-4-[(R)-1-(4-chlorophenyl)-ethyl]-7-iodo-2,5-dioxo-2,3,4,5-tetrahydro-benzo[e][1,4]diazepin-1-yl}-pentanoic acid; 5-{(3S)-7-Acetyl-3-(4-chlorophenyl)-4-[(R)-1-(4-chlorophenyl)-ethyl]-2,5-dioxo-2,3,4,5-tetrahydro-benzo[e][1,4]diazepin-1-yl}-pentanoic acid; 5-{(3S)-3-(3-Amino-4-chloro-phenyl)-4-[(R)-1-(4-chloro-phenyl)-ethyl]-7-iodo-2,5-dioxo-2,3,4,5-tetrahydro-benzo[e][1,4]diazepin-1-yl}-pentanoic acid; (3S)-2-Amino-3-(4-chlorophenyl)-4-[(R)-1-(4-chlorophenyl)-ethyl]-7-iodo-3,4-dihydro-benzo[e][1,4]diazepin-5-one; 2-{(3S)-3-(4-Chlorophenyl)-4-[(R)-1-(4-chlorophenyl)-ethyl]-7-iodo-5-oxo-4,5-dihydro-3H-benzo[e][1,4]diazepin-2-ylamino}-acetamide; (3S)-3-(4-Chloro-phenyl)-4-[(R)-1-(4-chloro-phenyl)-ethyl]-2-(2-hydroxy-ethylamino)-7-iodo-3,4-dihydro-benzo[e][1,4]diazepin-5-one; (3S)-3-(4-Chloro-phenyl)-4-[(R)-1-(4-chloro-phenyl)-ethyl]-2-(3-hydroxy-propylamino)-7-iodo-3,4-dihydro-benzo[e][1,4]diazepin-5-one; N-(2-{(3S)-3-(4-Chloro-phenyl)-4-[(R)-1-(4-chloro-phenyl)-ethyl]-7-iodo-5-oxo-4,5-dihydro-3H-benzo[e][1,4]diazepin-2-ylamino}-ethyl)-acetamide; (3S)-3-(4-Chloro-phenyl)-4-[(R)-1-(4-chloro-phenyl)-ethyl]-7-iodo-2-methylamino-3,4-dihydro-benzo[e][1,4]diazepin-5-one; 2-(2-Amino-ethylamino)-(3S)-3-(4-chloro-phenyl)-4-[(R)-1-(4-chloro-phenyl)-ethyl]-7-iodo-3,4-dihydro-benzo[e][1,4]diazepin-5-one; 2-[N-(3-amino-3-oxopropyl)amino]-(3S)-3-(4-chlorophenyl)-4-[(R)-1-(4-chlorophenyl)ethyl]-7-iodo-3,4-dihydro-1,4-benzodiazepin-5-one; 5-[(3S)-3-(4-chlorophenyl)-4-[(R)-1-(4-chlorophenyl)ethyl]-7-methoxycarbonyl-2,5-dioxo-3,4-dihydro-1H-1,4-benzodiazepin-1-yl]valeric acid tert-butyl ester; (3S)-1-(4-tert-Butoxycarbonyl-butyl)-3-(4-chloro-phenyl)-4-[(R)-1-(4-chloro-phenyl)-ethyl]-2,5-dioxo-2,3,4,5-tetrahydro-1H-benzo[e][1,4]diazepine-7-carboxylic acid; 7-aminocarbonyl-5-[(3S)-3-(4-chlorophenyl)-4-[(R)-1-(4-chlorophenyl)ethyl]-2,5-dioxo-3,4-dihydro-1H-1,4-benzodiazepin-1-yl]valeric acid; 5-[4-(4-Chloro-2-methyl-benzyl)-3-(R,S)-(4-chloro-phenyl)-7-iodo-2,5-dioxo-2,3,4,5-tetrahydro-benzo[e][1,4]diazepin-1-yl]-valeric acid; Sodium; 5-{(3R)-3-(4-chloro-phenyl)-4-[(R)-1-(4-chloro-phenyl)-ethyl]-7-iodo-2,5-dioxo-2,3,4,5-tetrahydro-benzo[e][1,4]diazepin-1-yl}-valerate; 5-[(3S)-3-(4-Chlorophenyl)-4-[(R)-1-(4-chlorophenyl)-ethyl]-7-[(R,S)-1-hydroxyethyl)-2,5-dioxoo-2,3,4,5-tetrahydro-benzo[e][1,4]diazepin-1-yl]-valeric acid; 5-[(R,S)-3-(4-Chloro-phenyl)-4-[(R)-1-(4-chloro-phenyl)-ethyl]-7-(1-(R,S)-hydroxyethyl)-2,5-dioxo-2,3,4,5-tetrahydro-benzo[e][1,4]diazepin-1-yl]-valeric acid; 5-[(3S)-4-[(R)-1-(4-Chlorophenyl)ethyl]-7-iodo-2,5-dioxo-3-(4-trifluoromethyl-phenyl)-2,3,4,5-tetrahydro-benzo[e][1,4]diazepin-1-yl]-valeric acid; Sodium; 5-{(S)-3-(4-chloro-phenyl)-4-[(R)-1-(4-chloro-phenyl)-ethyl]-7-ethynyl-2,5-dioxo-2,3,4,5-tetrahydro-benzo[e][1,4]diazepin-1-yl}-valerate; 5-{(3R,S)-3-(4-Chlorophenyl)-4-[(R,S)-1-(4-chlorophenyl)-2-hydroxyethyl)-7-iodo-2,5-dioxo-2,3,4,5-tetrahydro-benzo[e][1,4]diazepin-1-yl}-valeric acid; Sodium; 5-{(3S)-3-(4-chlorophenyl)-4-[(R)-1-(4-chlorophenyl)ethyl]-7-iodo-2,5-dioxoo-2,3,4,5-tetrahydro-benzo[e][1,4]diazepin-1-yl}-valerate; 5-[(3R,S)-4-(4-Chloro-2-methyl-benzyl)-3-(4-chloro-phenyl)-7-iodo-2,5-dioxo-2,3,4,5-tetrahydro-benzo[e][1,4]diazepin-1-yl]-valeric acid; Sodium; 5-{(3R)-3-(4-chlorophenyl)-4-[(R)-1-(4-chlorophenyl)ethyl]-7-iodo-2,5-dioxo-2,3,4,5-tetrahydro-benzo[e][1,4]diazepin-1-yl}-valerate; 5-[(3S)-3-(4-Chlorophenyl)-4-[(R)-1-chlorophenyl)-ethyl]-7-(1-(R,S)-hydroxyethyl)-2,5-dioxo-2,3,4,5-tetrahydro-benzo[e][1,4]diazepin-1-yl]-valeric acid; 5-[(3R,S)-3-(4-Chlorophenyl)-4-[(R)-1-(4-chlorophenyl)ethyl]-7-[(R,S)-1-hydroxy-ethyl]-2,5-dioxoo-2,3,4,5-tetrahydro-benzo[e][1,4]diazepin-1-yl]-valeric acid; 5-[(3S)-4-[(R)-1-(4-Chlorophenyl)-ethyl]-7-iodo-2,5-dioxo-3-(4-trifluoromethyl-phenyl)-2,3,4,5-tetrahydro-benzo[e][1,4]diazepin-1-yl]-valeric acid; Sodium; 5-{(3S)-3-(4-chlorophenyl)-4-[(R)-1-4-chlorophenyl)-ethyl]-7-ethynyl-2,5-dioxo-2,3,4,5-tetrahydro-benzo[e][1,4]diazepin-1-yl}-valerate; 5-{3-(4-Chlorophenyl)-4-[1-(4-chlorophenyl)-2-hydroxy-ethyl]-7-iodo-2,5-dioxo-2,3,4,5-tetrahydro-benzo[e][1,4]diazepin-1-yl}-valeric acid; Sodium; 5-{(3S)-3-(4-chlorophenyl)-4-[(R)-1-(4-chlorophenyl)-ethyl]-7-iodo-2,5-dioxo-2,3,4,5-tetrahydro-benzo[e][1,4]diazepin-1-yl}-valerate; 5-[(3S)-3-(4-Chlorophenyl)-4-[(R)-1-(4-chlorophenyl)ethyl]-7-(methylthio)-2,5-dioxo-1,4-benzodiazepin-1-yl]valeric acid; 5-[(3R)-3-(4-Chlorophenyl)-4-[(R)-1-(4-chlorophenyl)ethyl]-7-(methylthio)-2,5-dioxo-1,4-benzodiazepin-1-yl]valeric acid; 5-[(3S)-3-(4-Chlorophenyl)-4-[(R)-1-(4-chlorophenyl)ethyl]-7-(trifluoromethylthio)-2,5-dioxo-1,4-benzodiazepin-1-yl]valeric acid; 5-[(3S)-3-(2-Allyloxy-4-chlorophenyl)-4-[(R)-1-(4-chlorophenyl)ethyl]-7-iodo-2,5-dioxo-1,4-benzodiazepin-1-yl]valeric acid; 5-[(3S)-3-(4-chloro-2-hydroxyphenyl)-4-[(R)-1-(4-chlorophenyl)ethyl]-7-iodo-2,5-dioxo-1,4-benzodiazepin-1-yl]valeric acid; 5-[(3S)-3-(4-Chlorophenyl)-4-[(R)-1-(4chlorophenyl)ethyl]-2,5-dioxo-7-phenyl-1,4-diazepin-1-yl]valeric acid sodium salt; 5-[(3S)-7-(2-Bromophenyl)-3-(4-chlorophenyl)-4-[(R)-1-(4-chlorophenyl)ethyl]-2,5-dioxo-1,4-diazepin-1-yl]valeric acid sodium salt; 5-[(3S)-3-(4-Chlorophenyl)-4-[(R)-1-(4-chlorophenyl)ethyl]-7-(2,5-dimethylphenyl)-2,5-dioxo-1,4-diazepin-1-yl]valeric acid sodium salt; 5-[(3S)-3-(4-Chlorophenyl)-4-[(R)-1-(4-chlorophenyl)ethyl]-7-(2-methylphenyl)-2,5-dioxo-1,4-benzodiazepine-1-yl]valeric acid sodium salt; 5-[4-[1-(2-Amino-4-chlorophenyl)ethyl]-3-(4-chlorophenyl)-7-iodo-2,5-dioxo-1,4-benzodiazepin-1-yl]valeric acid sodium salt; 5-[4-[(2-Amino-4-chlorobenzyl)-7-bromo-3-(4-chlorophenyl)-2,5-dioxo-1,4-benzodiazepin-1-yl]valeric acid sodium salt; 4-(4-Chlorobenzyl)-3-(4-chloro-phenyl)-7-iodo-3,4-dihydro-1H-benzo[e][1,4]diazepine-2,5-dione; 4-(R)-[1-(2-Amino-4-chloro-5-fluoro-phenyl)-ethyl]-3-(S)-(4-chloro-phenyl)-7-iodo-1-(2-morpholin-4-yl-ethyl)-3,4-dihydro-1H-benzo[e][1,4]diazepine-2,5-dione; 4-(R,S)-[1-(2-Amino-4-chloro-5-hydroxy-phenyl)-ethyl]-3-(S,R)-(4-chloro-phenyl)-7-iodo-1-(2-morpholin-4-yl-ethyl)-3,4-dihydro-1H-benzo[e][1,4]diazepine-2,5-dione; 3-(S)-(4-Chloro-2-hydroxy-phenyl)-4-(R)-[1-(4-chloro-phenyl)-ethyl]-7-iodo-3,4-dihydro-1H- benzo[e][1,4]diazepine-2,5-dione; 4-[1-(2-Amino-4-chloro-phenyl)-ethyl]-3-(4-chloro-phenyl)-7-iodo-1-[3-(4-methyl-piperazin-1-yl)-propyl]-3,4-dihydro-1H-benzo[e][1,4]diazepine-2,5-dione; 4-(2-Amino-4-chloro-benzyl)-3-(4-chloro-phenyl)-1-(4-dimethylamino-butyl)-7-iodo-3,4-dihydro-1H-benzo[e][1,4]diazepine-2,5-dione; 4-(2-Amino-4-chloro-benzyl)-3-(4-chloro-phenyl)-7-iodo-1-(4-morpholin-4-yl-butyl)-3,4-dihydro-1H-benzo[e][1,4]diazepine-2,5-dione; 4-(2-Amino-4-chloro-benzyl)-3-(4-chloro-phenyl)-7-iodo-1-[4-(4-methyl-piperazin-1-yl)-butyl]-3,4-dihydro-1H-benzo[e][1,4]diazepine-2,5-dione; 4-(2-Amino-4-chloro-benzyl)-3-(4-chloro-phenyl)-1-(3-dimethylamino-propyl)-7-iodo-3,4-dihydro-1H-benzo[e][1,4]diazepine-2,5-dione; 4-(2-Amino-4-chloro-benzyl)-3-(4-chloro-phenyl)-7-iodo-1-(3-morpholin-4-yl-propyl)-3,4-dihydro-1H-benzo[e][1,4]diazepine-2,5-dione; 4-(4-Chloro-2-hydroxybenzyl)-3-(4-chlorophenyl)-7-iodo-1-[2-(2-methoxy-ethoxy)ethyl]-3,4-dihydro-1H-benzo[e][1,4]diazepine-2,5-dione; 4-[(S)-1-(2-Amino-4-chlorophenyl)ethyl]-(3R)-3-(4-chlorophenyl)-7-iodo-1-(2-morpholin-4-ylethyl)-3,4-dihydro-1H-benzo[e][1,4]diazepine-2,5-dione; 4-(2-Amino-4-chlorobenzyl)-3-(4-chlorophenyl)-7-iodo-1-[3-(4-methyl-piperazin-1-yl)propyl]-3,4-dihydro-1H-benzo[e][1,4]diazepine-2,5-dione; 5-(2-Allyloxy-4-chlorobenzyloxy)-3-(4-chlorophenyl)-7-iodo-1-[2-(2-methoxyethoxy)ethyl]-1,3-dihydrobenzo[e][1,4]diazepin-2-one; 4-(2-Amino-4-chlorobenzyl)-3-(4-chlorophenyl)-7-iodo-3,4-dihydro-1H-benzo[e][1,4]diazepine-2,5-dione; 4-[1-(3-Amino-4-chlorophenyl)ethyl]-3-(4-chlorophenyl)-7-iodo-3,4-dihydro-1H-benzo[e][1,4]diazepine-2,5-dione; 4-Benzyl-7-bromo-3-(4-chlorophenyl)-1-methyl-1,4-benzodiazepine-2,5-dione; 7-Bromo-3-(4-chlorophenyl)-1-methyl-4-(1-phenethyl)-1,4-benzodiazepine-2,5-dione; 1,3-Dihydro-4-[1-(2-amino-4-chlorophenyl)ethyl]-3-(4-chlorophenyl)-7-iodo-1,4-benzodiazepine-2,5-dione; 3-(4-Chlorophenyl)-4-[1-(4-chloro-2-nitrophenyl)ethyl]-7-iodo-1-[2-(4-morpholino)ethyl]-1,4-benzodiazepine-2,5-dione; 5-[(3S)-3-(4-Chlorophenyl)-4-[(R)-1-(4-chlorophenyl)ethyl]-2,5-dioxo-7-(propyn-1-yl)-1,4-benzodiazepin-1-yl]valeric acid sodium salt; 4-[1-(2-Amino-4-chlorophenyl)ethyl]-3-(4-chlorophenyl)-7-iodo-1-[2-(2-methoxyethoxy)ethyl]-1,4-benzodiazepine-2,5-dione; 4-[(R)-1-(2-amino-4-chlorophenyl)ethyl]-(3S)-3-(4-chlorophenyl)-7-iodo-1-[2-(2-methoxyethoxy)ethyl]-1,4-benzodiazepine-2,5-dione; (3R)-4-[(S)-1-(2-amino-4-chlorophenyl)ethyl]-3-(4-chlorophenyl)-7-iodo-1-[2-(2-methoxyethoxy)ethyl]-1,4-benzodiazepine-2,5-dione; 4-[1-(2-Amino-4-chlorophenyl)ethyl]-3-(4-chlorophenyl)-7-iodo-1-[2-(4-morpholino)ethyl]-1,4-benzodiazepine-2,5-dione; (3S)-4-[(R)-1-(2-Amino-4-chlorophenyl)ethyl]-3-(4-chlorophenyl)-7-iodo-1-[2-(4-morpholino)ethyl]-1,4-benzodiazepine-2,5-dione; (3R)-4-[(S)-1-(2-amino-4-chlorophenyl)ethyl]-3-(4-chlorophenyl)-7-iodo-1-[2-(4-morpholino)ethyl]-1,4-benzodiazepine-2,5-dione; 3-(4-Chlorophenyl)-4-[1-(2,6-dichloro-3-pyridyl)ethyl]-7-iodo-1,4-benzodiazepine-2,5-dione; 1,3-Dihydro-4-[1-(2-amino-4-chlorophenyl)ethyl]-3-(4-chlorophenyl)-7-iodo-1-methyl-1,4-benzodiazepine-2,5-dione; 1,3-Dihydro-4-[1-(2-acetylamino-4-chlorophenyl)ethyl]-3-(4-chlorophenyl)-7-iodo-1,4-benzodiazepine-2,5-dione; 1,3-Dihydro-4-[1-(2-azido-3-pyridyl)ethyl]-3-(4-chlorophenyl)-7-iodo-1,4-benzodiazepine-2,5-dione; 4-[1-(2-Amino-4-chlorophenyl)ethyl]-3-(4-chlorophenyl)-1-[2-(2-methoxyethoxy)ethyl]-7-(propyn-1-yl)-1,4-benzodiazepine-2,5-dione hydrochloride; (3S)-4-[(R)-1-(2-Amino-4-chlorophenyl)ethyl]-3-(4-chlorophenyl)-1-[2-(2-methoxyethoxy)ethyl]-7-(propyn-1-yl)-1,4-benzodiazepine-2,5-dione hydrochloride; 4-[1-(2-Amino-4chlorophenyl)ethyl]-3-(4chlorophenyl)-1-[2-(4-morpholino)ethyl]-7-(propyn-1-yl)-1,4-benzodiazepine-2,5-dione hydrochloride; (3S)-4-[(R)-1-(2-Amino-4-chlorophenyl)ethyl]-3-(4-chlorophenyl)-1-[2-(4-morpholino)ethyl]-7-(propyn-1-yl)-1,4-benzodiazepine-2,5-dione hydrochloride; 4-[1-(2-Amino-4-chlorophenyl)ethyl]-3-(4-chlorophenyl)-7-iodo-2,3-dihydro-1H-1,4-benzodiazepin-5-one; 4-[1-(2-amino-6-chloro-3-pyridyl)methyl]-3-(4-chlorophenyl)-7-iodo-1-[2-(2-methoxyethoxy)ethyl]-1,4-benzodiazepine-2,5-dione hydrochloride; 4-[1-(3-Amino-4-chlorophenyl)cyclopropyl]-3-(4-chlorophenyl)-1-[2-(4-morpholino)ethyl]-7-iodo-1,4-benzodiazepine-2,5-dione methanesulfonate; (3S)-4-[1-(2-Amino-4-chlorophenyl)ethyl]-3-(4-chlorophenyl)-7-iodo-1-[(R)-2-(1-piperazinyl)-2-oxoethyl]-1,4-benzodiazepine-2,5-dione hydrochloride; 4-(4-Chloro-2-methyl-benzyl)-3-(4-chloro-phenyl)-7-iodo-1-(2-morpholin-4-yl-ethyl)-3,4-dihydro-1H-benzo[e][1,4]diazepine-2,5-dione; 3-(S)-(4-Chloro-phenyl)-4-[1-(R)-(4-chloro-phenyl)-ethyl]-7-iodo-1-(2-morpholin-4-yl-2-oxo-ethyl)-3,4-dihydro-1H-benzo[e][1,4]diazepine-2,5-dione; 3-(S)-(4-Chloro-phenyl)-4-[1-(R)-(4-chloro-phenyl)-ethyl]-7-iodo-1-(2-morpholin-4yl-ethyl)-3,4-dihydro-1H-benzo[e][1,4]diazepine-2,5-dione; 3-(R)-(4-Chloro-phenyl)-4-[1-(R)-(4-chloro-phenyl)-ethyl]-7-iodo-1-(2-morpholin-4-yl-ethyl)-3,4-dihydro-1H-benzo[e][1,4]diazepine-2,5-dione; 3-(S)-(4-Chloro-phenyl)-4-[1-(R)-(4-chloro-phenyl)-ethyl]-7-iodo-1-[2-(2-methoxy-ethoxy)-ethyl]-3,4-dihydro-1H-benzo[e][1,4]diazepine-2,5-dione; 3-(S)-(4-Chloro-phenyl)-4-[1-(R)-(4-chloro-phenyl)-ethyl]-7-(1-hydroxyimino-ethyl)-3,4-dihydro-1H-benzo[e][1,4]diazepine-2,5-dione; 7-Iodo-4-naphthalen-1-ylmethyl-3-(4-trifluoromethoxy-phenyl)-3,4-dihydro-1H-benzo[e][1,4]diazepine-2,5-dione; 4-Benzo[1,3]dioxol-5-ylmethyl-3-(4-chloro-phenyl)-7-iodo-3,4-dihydro-1H-benzo[e][1,4]diazepine-2,5-dione; 4-Benzo[1,3]dioxol-5-ylmethyl-7-iodo-3-(4-trifluoromethoxy-phenyl)-3,4-dihydro-1H-benzo[e][1,4]diazepine-2,5-dione; 7-Iodo-4-(2-pyridin-2-yl-ethyl)-3-(4-trifluoromethoxy-phenyl)-3,4-dihydro-1H-benzo[e][1,4]diazepine-2,5-dione; 4-Benzyl-3-(4-chloro-phenyl)-7-iodo-3,4-dihydro-1H-benzo[e][1,4]diazepine-2,5-dione; 3-(4-Chloro-phenyl)-7-iodo-4-phenethyl-3,4-dihydro-1H-benzo[e][1,4]diazepine-2,5-dione; 4-Benzyl-7-iodo-3-(4-trifluoromethoxy-phenyl)-3,4-dihydro-1H-benzo[e][1,4]diazepine-2,5-dione; 7-Iodo-4-phenethyl-3-(4-trifluoromethoxy-phenyl)-3,4-dihydro-1H-benzo[e][1,4]diazepine-2,5-dione.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabeled compound of the invention, administering it parenterally in a detectable dose to an animal such as rat, mouse, guinea pig, monkey, or to man, allowing sufficient time for metabolism to occur and isolating its conversion products from the urine, blood or other biological samples.

Some of the compounds disclosed herein may contain one or more asymmetric centers and thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached, or a sulfur atom to which three different groups are attached, where the sulfur atom and its attached groups form a sulfoxide, sulfinic ester, sulfonium salt or sulfite.

The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

The compounds of Formula I may also be solvated, especially hydrated. Hydration may occur during manufacturing of the compounds or compositions comprising the compounds, or the hydration may occur over time due to the hygroscopic nature of the compounds.

Certain compounds within the scope of Formula I are derivatives referred to as "prodrugs." The expression "prodrug" denotes a derivative of a known direct acting drug, which derivative has enhanced delivery characteristics and therapeutic value as compared to the drug, and is transformed into the active drug by an enzymatic or chemical process. Prodrugs are derivatives of the compounds of the invention which have metabolically cleavable groups and become by solvolysis or under physiological conditions the compounds of the invention which are pharmaceutically active in vivo. For example, ester derivatives of compounds of this invention are often active in vivo, but not in vitro. Other derivatives of the compounds of this invention have activity in both their acid and acid derivative forms, but the acid derivative form often offers advantages of solubility, tissue compatibility, or delayed release in the mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with an amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Useful prodrugs are those where $R^b$ is alkyl, alkenyl, alkynyl, or arylalkyl.

When any variable occurs more than one time in any constituent or in Formula I, its definition on each occurrence is independent of its definition at every other occurrence. Also, combinations of substituents and/or variables are permissible only if such combinations result in stable compounds.

Definitions

The term "alkyl" as employed herein by itself or as part of another group refers to both straight and branched chain radicals of up to 10 carbons, unless the chain length is otherwise limited, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, or decyl.

The term "alkenyl" is used herein to mean a straight or branched chain radical of 2–10 carbon atoms, unless the chain length is otherwise limited, wherein there is at least one double bond between two of the carbon atoms in the chain, including, but not limited to, ethenyl, 1-propenyl, 2-propenyl, 2-methyl-1-propenyl, 1-butenyl, 2-butenyl, and the like. Preferably, the alkenyl chain is 2 to 8 carbon atoms in length, most preferably from 2 to 4 carbon atoms in length.

The term "alkynyl" is used herein to mean a straight or branched chain radical of 2–10 carbon atoms, unless the chain length is otherwise limited, wherein there is at least one triple bond between two of the carbon atoms in the chain, including, but not limited to, ethynyl, 1-propynyl, 2-propynyl, and the like. Preferably, the alkynyl chain is 2 to 8 carbon atoms in length, most preferably from 2 to 4 carbon atoms in length.

In all instances herein where there is an alkenyl or alkynyl moiety as a substituent group, the unsaturated linkage, i.e., the vinyl or ethenyl linkage, is preferably not directly attached to a nitrogen, oxygen or sulfur moiety.

The term "alkoxy" or "alkyloxy" refers to any of the above alkyl groups linked to an oxygen atom. Typical examples are methoxy, ethoxy, isopropyloxy, sec-butyloxy, and t-butyloxy.

The term "aryl" as employed herein by itself or as part of another group refers to monocyclic or bicyclic aromatic groups containing from 6 to 12 carbons in the ring portion, preferably 6–10 carbons in the ring portion. Typical examples include phenyl, biphenyl, naphthyl or tetrahydronaphthyl.

The term "aralkyl" or "arylalkyl" as employed herein by itself or as part of another group refers to $C_{1-6}$ alkyl groups as discussed above having an aryl substituent, such as benzyl, phenylethyl or 2-naphthylmethyl.

The term "heteroaryl" as employed herein refers to groups having 5 to 14 ring atoms; 6, 10 or 14 pi electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups).

The phrase "saturated or partially unsaturated heterocycle" as employed herein, by itself or as part of another group, refers to a saturated or partially unsaturated ring system having 5 to 14 ring atoms selected from carbon atoms and 1, 2, 3, or 4 oxygen, nitrogen, or sulfur heteroatoms. Typical saturated examples include pyrrolidinyl, imidazolidinyl, pyrazolidinyl, tetrahydrofuranyl, tetrahydropyranyl, piperidyl, piperazinyl, quinuclidinyl, morpholinyl, and dioxacyclohexyl. Typical partially unsaturated examples include pyrrolinyl, imidazolinyl, pyrazolinyl, dihydropyridinyl, tetrahydropyridinyl, and dihydropyranyl. Either of these systems can be optionally fused to a benzene ring.

The terms "heteroarylalkyl" or "heteroaralkyl" as employed herein both refer to a heteroaryl group attached to an alkyl group. Typical examples include 2-(3-pyridyl)ethyl, 3-(2-furyl)-n-propyl, 3-(3-thienyl)-n-propyl, and 4-(1-isoquinolinyl)-n-butyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "cycloalkylalkyl" or "cycloalkyl(alkyl)" as employed herein, by itself or as part of another group, refers to a cycloalkyl group attached to an alkyl group. Typical examples are 2-cyclopentylethyl, cyclohexylmethyl, cyclopentylmethyl, 3-cyclohexyl-n-propyl, and 5-cyclobutyl-n-pentyl.

The term "cycloalkenyl" as employed herein, by itself or as part of another group, refers to cycloalkenyl groups containing 3 to 9 carbon atoms and 1 to 3 carbon-carbon double bonds. Typical examples include cyclopropenyl, cyclobutenyl, cyclopentenyl, cyclohexenyl, cyclohexadienyl, cycloheptenyl, cycloheptadienyl, cyclooctenyl, cyclooctadienyl, cyclooctatrienyl, cyclononenyl, and cyclononadienyl.

The term "halogen" or "halo" as employed herein by itself or as part of another group refers to chlorine, bromine, fluorine or iodine.

The term "monoalkylamine" or "monoalkylamino" as employed herein by itself or as part of another group refers to the group $NH_2$ wherein one hydrogen has been replaced by an alkyl group, as defined above.

The term "dialkylamine" or "dialkylamino" as employed herein by itself or as part of another group refers to the group $NH_2$ wherein both hydrogens have been replaced by alkyl groups, as defined above.

The term "hydroxyalkyl" as employed herein refers to any of the above alkyl groups wherein one or more hydrogens thereof are substituted by one or more hydroxyl moieties.

The term "haloalkyl" as employed herein refers to any of the above alkyl groups wherein one or more hydrogens thereof are substituted by one or more halo moieties. Typical examples include fluoromethyl, difluoromethyl, trifluoromethyl, trichloroethyl, trifluoroethyl, fluoropropyl, and bromobutyl.

The term "carboxyalkyl" as employed herein refers to any of the above alkyl groups wherein one or more hydrogens thereof are substituted by one or more carboxylic acid moieties.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound form a saturated or unsaturated 5-, 6-, or 7-membered ring.

The phrase "optionally-substituted" when not explicitly defined refers to a group or groups being optionally substituted with one or more substituents independently selected from the group consisting of hydroxy, nitro, trifluoromethyl, halogen, $C_{1-6}$ alkyl, $C_{1-6}$ haloalkyl, $C_{1-6}$ alkoxy, $C_{1-6}$ alkylenedioxy, $C_{1-6}$ aminoalkyl, $C_{1-6}$ hydroxyalkyl, $C_{2-4}$ alkenyl, $C_{2-4}$ alkynyl, $C_{6-10}$ aryl, phenoxy, benzyloxy, 5-10 membered heteroaryl, $C_{1-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, $C_{2-6}$ alkoxycarbonylalkyl, carboxy, $C_{2-6}$ hydroxyalkoxy, $(C_{1-6})$ alkoxy($C_{2-6}$)alkoxy, mono($C_{1-4}$)alkylamino($C_{2-6}$)alkoxy, di($C_{1-4}$)alkylamino($C_{2-6}$)alkoxy $C_{2-10}$ mono(carboxyalkyl) amino, bis($C_{2-10}$ carboxyalkyl)amino, $C_{2-6}$ carboxyalkoxy, $C_{2-6}$ carboxyalkyl, carboxyalkylamino, guanidinoalkyl, hydroxyguanidinoalkyl, cyano, trifluoromethoxy, or perfluoroethoxy.

Preferred optional substituents include one or more substituents independently selected from the group consisting of nitro, hydroxy, carboxy, $C_{1-4}$ alkoxy, $C_{1-4}$ alkyl, halo, $C_{1-4}$ haloalkyl, $C_{1-4}$ alkylthio, thio, amino, mono($C_{1-4}$)alkylamino, and di($C_{1-4}$)alkylamino.

"mdm2" is used herein to mean the murine double minute 2 gene, and homologous genes found in other animals.

"MDM2" is used herein to mean a protein obtained as a result of expression of the mdm2 oncogene. Within the meaning of this term, it will be understood that MDM2 encompasses all proteins encoded by mdm2, mutants thereof, alternative splice proteins thereof, and phosphorylated proteins thereof. Additionally, as used herein, it will be understood that the term "MDM2" includes MDM2 homologues of other animals (e.g., HDM2).

"hdm2" is used herein to mean the human gene which is homologous to the mouse mdm2.

"HDM2" is used herein to mean a protein obtained as a result of expression of the hdm2 oncogene. Within the meaning of this term, it will be understood that HDM2 encompasses all proteins encoded by the hdm2, mutants thereof, alternative splice proteins thereof, and phosphorylated proteins thereof.

The phrase "antineoplastic agent" is used herein to mean any agent that is used to treat or prevent cancer or other conditions comprising uncontrolled proliferation and growth of cells. Antineoplastic agents include anticancer agents.

The phrase "contacting one or more proteins" is used herein to mean placing a compound of the present invention in a solution with one or more proteins of interest. A compound of Formula I and one or more proteins of interest may be in solution together in an aqueous solution, non-aqueous solution, or combination of an aqueous solution and non-aqueous solution. Other proteins may be present in solution along with the compound of Formula I and the protein of interest. Other inorganic or organic molecules may be present in the solution. Such inorganic and organic molecules include, but are not limited to, NaCl, HEPES, and octyl glucoside. The solution may be within an animal cell or outside of an animal cell.

The phrase "inhibiting the binding" is used herein to mean preventing or reducing the direct or indirect association of one or more molecules, peptides, proteins, enzymes, or receptors; or preventing or reducing the normal activity of one or more molecules, peptides, proteins, enzymes, or receptors.

The phrase "inducing apoptosis" is used herein to mean causing directly or indirectly a cell of animal origin to undergo apoptosis, a process of controlled, or programmed, cellular death.

The phrase "HDM2 inhibitor" is used herein to describe an agent which inhibits the function of HDM2 in the assay described in Example 35.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, palmoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; and aralkyl halides like benzyl and phenethyl bromides and others. Preferred acids for forming acid addition salts include HCl, acetic acid, trifluoroacetic acid and fumaric acid.

Compositions and Methods of Use

Compositions of the present invention include pharmaceutical compositions comprising a compound of Formula I, wherein $R^1$–$R^{11}$ and X are defined above, and one or more pharmaceutically acceptable excipients. Preferred compositions of the present invention are pharmaceutical compositions comprising a compound selected from a preferred group of compounds of Formula I as defined above, and one or more pharmaceutically acceptable excipients.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by subcutaneous, intravenous, intramuscular, intraperitoneal, buccal, or ocular routes, rectally, parenterally, intrasystemically, intravaginally, topically (as by powders, ointments, drops or transdermal patch), or as an oral or nasal spray. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragée cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropyl methylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragée cores are provided with suitable coatings that, if desired, are resistant to gastric juices. For this purpose, concentrated saccharide solutions can be used, which can contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are anumonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition are preferably such that the active ingredients do not dissolve therein to any substantial extent. The pressurized composition may also contain a surface-active agent. The surface-active agent may be a liquid or solid non-ionic surface-active agent or may be a solid anionic surface-active agent. It is preferred to use the solid anionic surface-active agent in the form of a sodium salt.

A further form of topical administration is to the eye. The compounds and compositions of the present invention are delivered in a pharmaceutically acceptable ophthalmic vehicle, such that the compounds are maintained in contact with the ocular surface for a sufficient time period to allow the compounds to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:33 (1976)).

Compounds of the present invention may be used alone or in combination with one or more additional antineoplastic agents. When a compound of the present invention is used along with one or more additional antineoplastic agents, the compound of the present invention may be formulated with the other antineoplastic agent or agents so that a pharmaceutical composition comprising a compound of Formula I and one or more additional antineoplastic agents is administered to an animal. Alternatively, the compound of Formula I can be administered as a separate pharmaceutical composition from the composition comprising the one or more additional antineoplastic agents. Antineoplastic agents that may be used in combination with the compounds of the present invention include compounds selected from the following compounds and classes of antineoplastic agents:

1. fluoropyrimidines, such as 5-FU (5-fluorouracil), Fluorodeoxyuridine, Ftorafur, 5'-deoxyfluorouridine, UFT, and S-1 Capecitabine;

2. pyrimidine nucleosides, such as Deoxycytidine, Cytosine Arabinoside, Cytarabine, Azacitidine, 5-Azacytosine, Gencitabine, and 5-Azacytosine-Arabinoside;

3. purines, such as 6-Mercaptopurine, Thioguanine, Azathioprine, Allopurinol, Cladribine, Fludarabine, Pentostatin, and 2-Chloroadenosine;

4. platinum analogues, such as Cisplatin, Carboplatin, Oxaliplatin, Tetraplatin, Platinum-DACH, Ormaplatin, and CI-973, JM-216;

5. anthracyclines/anthracenediones, such as Doxorubicin, Daunorubicin, Epirubicin, Idarubicin, and Mitoxantrone;

6. epipodophyllotoxins, such as Etoposide, and Teniposide;

7. camptothecins, such as Irinotecan, Topotecan, 9-Amino Camptothecin, 10,11-Methylenedioxy Camptothecin, 9-Nitro Camptothecin, and TAS 103;

8. hormones and hormonal analogues, such as diethylstilbestrol, Tamoxifen, Toremefine, Tolmudex, Thymitaq, flutamide, fluoxymesterone, bicalutamide, Finasteride, estradiol, Trioxifene, dexamethasone, leuproelin acetate, estramustine, Droloxifene, medroxyprogesterone, megesterol acetate, aminoglutethimide, testolactone, testosterone, diethylstilbestrol, and hydroxyprogesterone;

9. enzymes, proteins and antibodies, such as Asparaginase, Interleukins, Interferons, Leuprolide, and Pegaspargase;

10. vinca alkaloids, such as Vincristine, Vinblastine, Vinorelbine, and Vindesine;

11. taxanes, such as Paclitaxel, Taxotere and Docetaxel.

Antineoplastic agents that may be used in combination with compounds of the invention also include compounds selected from the following Mechanism-Based Classes:

1. Antihormonals-See classification for Hormones and Hormonal Analogs above, Anastrozole, Goserelin, and Aminoglutethimide;

2. Antifolates, such as methotrexate, leucovorin, aminopterin, trimetrexate, Trimethoprim, pyritrexim, pyrimethamine, Edatrexate, and MDAM;

3. Antimicrotubule Agents, such as Taxanes, Vinca Alkaloids, and Vinorelbine;

4. Alkylating Agents (Classical and Non-Classical), such as Nitrogen Mustards (Mechlorethamine, Chlorambucil, Melphalan, Uracil Mustard), Oxazaphosphorines (Ifosfamide, Cyclophosphamide, Perfosfamide, Trophosphamide), Alkylsulfonates (Busulfan), Nitrosoureas (Carmustine, Lomustine, Streptozocin), Thiotepa, and Dacarbazine;

5. Antimetabolites, such as Purines, pyrimidines and nucleoside analogs, listed above;

6. Antibiotics, such as Anthracyclines/Anthracenediones, Bleomycin, Dactinomycin, Mitomycin, Plicamycin, Pentostatin, and Streptozocin;

7. Topoisomerase Inhibitors, such as Camptothecins (Topo I), Epipodophyllotoxins, AMSA, VP-16 and Ellipticines (Topo II);

8. Antivirals, such as AZT, acyclovir, penciclovir, famcyclovir, didehydrodideoxythymidine, dideoxycytidine, -SddC, ganciclovir, dideoxyinosine, and viral-specific protease inhibitors;

9. Miscellaneous Cytotoxic Agents, such as Hydroxyurea, Mitotane, Fusion Toxins, PZA, Bryostatin, Retinoids, Butyric Acid and derivatives, Pentosan, Fumagillin, Mitoxantrone, Bone Marrow Growth Factors, and Procarbazine.

Compounds of the present invention are useful for the treatment of uncontrolled proliferation of cells and/or cancer. The compounds of the present invention may produce beneficial cytostatic and/or cytotoxic effects. The cytostatic effects include the inhibition of further cell growth and/or cell division. The cytotoxic effects include the induction of cell death by mechanisms that include apoptosis and cellular necrosis. Specifically, the compounds of the present invention are useful in treating the following cancers: breast cancer, ovarian cancer, cervical carcinoma, endometrial carcinoma, choriocarcinoma, soft tissue sarcomas, osteosarcomas, rhabdomyosarcomas, leiomyomas, leiomyosarcomas, head and neck cancers, lung and bronchogenic carcinomas, brain tumors, neuroblastomas, esophogeal cancer, colorectal adenocarcinomas, bladder cancer, urothelial cancers, leukemia, lymphoma, malignant melanomas, oral squamous carcinoma, hepatoblastoma, glioblastoma, astrocytoma, medulloblastoma, Ewing's sarcoma, lipoma, liposarcoma, malignant fibroblast histoma, malignant Schwannoma, testicular cancers, thyroid cancers, Wilms' tumor, pancreatic cancers, colorectal adenocarcinoma, tongue carcinoma, gastric carcinoma, and nasopharyngeal cancers. Preferably, the present invention is used to treat the cancers selected from the group consisting of breast cancer, choriocarcinoma, soft tissue sarcomas, osteosarcomas, rhabdomyosarcomas, lipoma and liposarcoma. The cancers and diseases listed above are merely meant to be illustrative and are by no means meant to be a limiting or exhaustive list.

Additionally, the compounds and compositions described herein are useful to treat any undesired or detrimental condition that results from the HDM2 protein or the MDM2 protein inhibiting the function of p53 or other cellular proteins that induce apoptosis, induce cellular death, or regulate the cellular cycle.

The compounds of the present invention are also useful at inhibiting the interaction between p53 and HDMX and/or MDMX. MDMX, also known as MDM4, is a cellular protein involved in the regulation of the cell cycle. For example, see Riemenschneider et al., Cancer Res. 59(24): 6091–6(1999).

Inhibitors of the interaction of HDM2 and/or MDM2 and p53 are also useful for treating cancer, inhibiting cell growth/replication, and inducing cellular apoptosis and necrosis, when administered along with agents that cause or induce DNA damage (see Chen et al. Proc. Natl. Acad. Sci. USA 95:195–200 (1998)). Compounds of the present invention may be used to treat cancer, inhibit cell growth/replication, and induce cellular apoptosis and necrosis, by administering a compound of the present invention along with agents that cause or induce DNA damage. Agents that induce DNA damage include radiation and chemical agents. The radiation can be administered either internally or externally. Chemical agents include any compounds or elements that cause or induce damage to DNA.

The compounds of the present invention may be administered in an effective amount within the dosage range of about 0.01 mg/kg to about 300 mg/kg, preferably between 1.0 mg/kg to 100 mg/kg body weight. Compounds of the present invention may be administered in a single daily dose, or the total daily dosage may be administered in divided doses of two, three or four times daily.

Preparation of Compounds

The compounds of the present invention can be prepared utilizing a modification of Ugi condensation reaction, according to the synthetic pathway shown in Scheme 1 and as detailed in Keating and Armstrong, J. Am. Chem. Soc., 118:2574–2583 (1996). Appropriately substituted or unsubstituted amino carboxylic acids 1, amines 3, and aldehydes 2 can be used to prepare the compounds of the present invention, wherein $R^1$, $R^2$, $R^5$, $R^6$, $R^7$, $R^8$, $R^9$ and $R^{10}$ are defined above. When $R^3X$ is selected as a group other than hydrogen or an electron pair, $R^3X$ can be introduced by using $R^3X$-halogen in the presence of a base, such as NaH, and a solvent, such as THF and/or catalyst such as tetrabutylammonium iodide. When $R^3X$ is hydrogen, compound 7 can be converted to amidine 8 through the use of phosphorous oxychloride and the appropriately substituted amine.

Scheme1:
Conventional Diazepine Synthesis

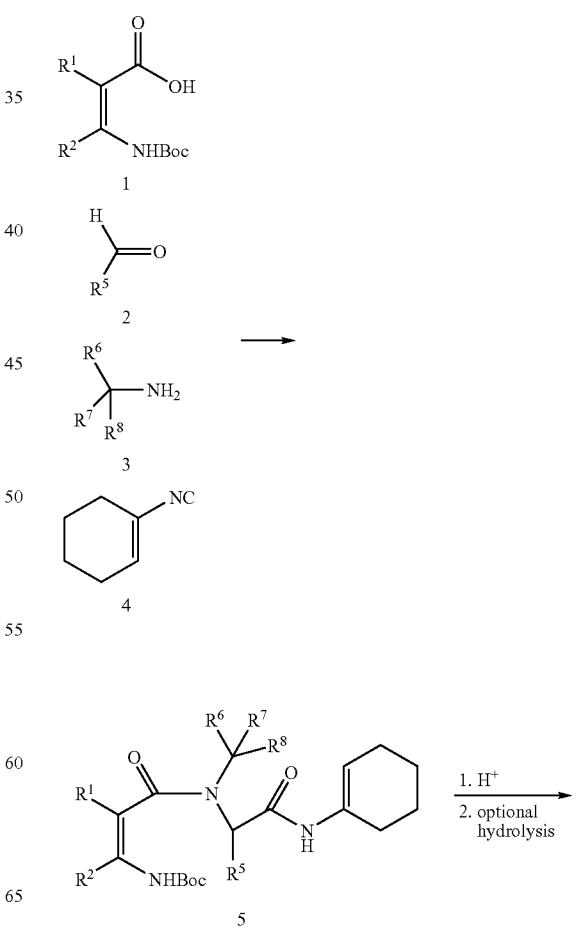

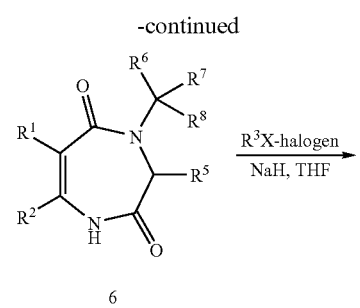

6

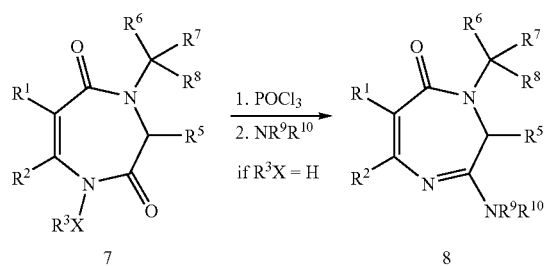

Alternatively, the compounds of the present invention can be prepared utilizing isatoic anhydride chemistry. Optionally-substituted furan-2,5-dione (9) is treated with trimethylsilyl azide to afford isatoic anhydride 10. Compound 10 is then treated with optionally-substituted amino ester in a solvent such as pyridine and heated to 125° C. in a sealed tube for 1.5 h, followed by the treatment with a base such as tBuOK, to afford compound 11. Compound 11 is then treated with a base such as sodium hydride followed by an appropriately substituted alkyl halide. The product formed is then treated with lithium bis(trimethylsilyl)amide at 0° C. in a solvent such as anhydrous DMF. After 10 min., an appropriately substituted alkyl halide is added to afford the final diazepine structure 12. Alternatively, compound 10 is treated with a base, such as NaH, in a solvent, such as DMF, followed by addition of an appropriately substituted alkyl halide. The product 13 formed is then treated with an optionally substituted amino ester in a solvent such as pyridine and heated to 125° C. in a sealed tube for 1.5 h, followed by the treatment with a base such as tBuOK, to afford compound 12 and 14.

Scheme 2:
Alternative Diazepine Synthesis #1

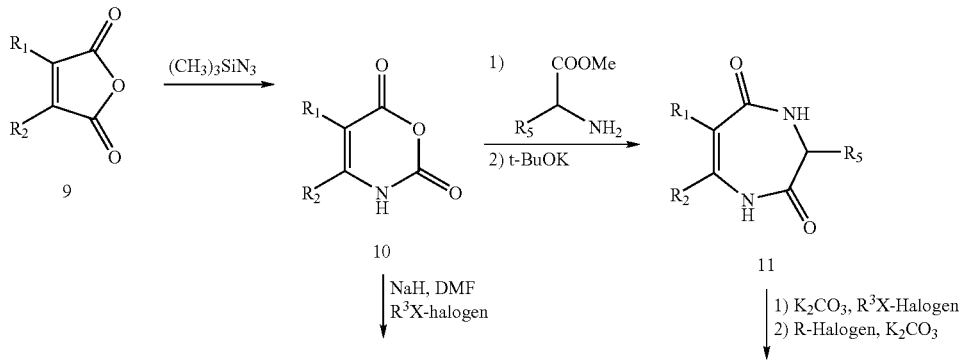

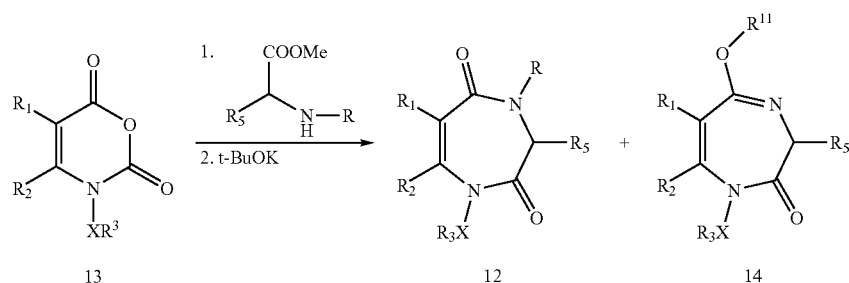

Alternatively, the compounds of the present invention can be prepared starting with an optionally substituted α-haloester. Compound 15, is treated with an optionally substituted amine, in the presence of a base, such as K₂CO₃, in a solvent such as acetonitrile to give compound 16. This can be treated with an optionally substituted α,β-unsaturated acid chloride in the presence of a base, such as diisopropylethylamine, in a solvent such as dichloromethane to give compound 17. This is treated with sodium hydroxide in methanol, followed by coupling with an optionally substituted amine in the presence of coupling reagents such as PyBrOP and HOBt, in a solvent, such as DMF, and a base, such as diisopropylethylamine, to give compound 18. This is subsequently treatment with silver triflate in acetonitrile, followed by addition of benzeneselenyl bromide and DMF. Then, hydrogen peroxide is added in the presence of a solvent, such as THF to give compound 19. If R³X is hydrogen, the solubilizing group can be introduced using R³X-halogen in the presence of a base, such as NaH, and a solvent, such as DMF.

Scheme 3:
Alternative Diazepine Synthesis #2

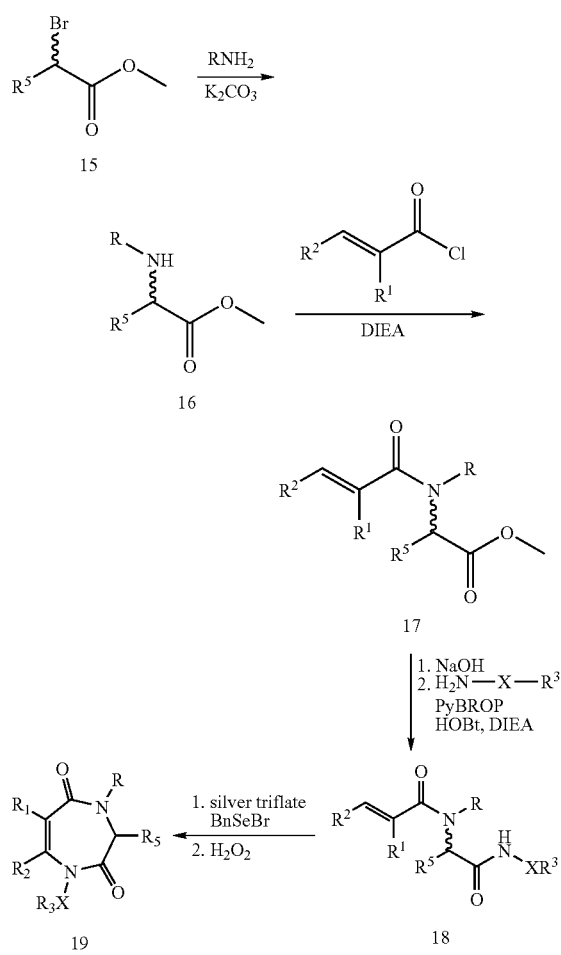

The following examples illustrate, but do not limit, the compounds, methods and compositions of the present invention. Other suitable modifications and adaptations of the variety of conditions and parameters normally encountered in clinical therapy and which are obvious to those skilled in the art are within the spirit and scope of the invention.

EXAMPLES

The compounds in the examples below were synthesized by the following general procedures.

General Procedure for the Conventional Synthesis of Diazepine Compounds

A solution of the aldehyde (0.20 mmol) and amine (0.20 mmol) in methanol (2.0 mL) were stirred at ambient temperature for 30 min. To this solution was added a solution of cyclohexene-1-isonitrile (0.21 mmol) in hexanes, followed by the aryl or heteroaryl amino acid (0.20 mmol). The solution was then stirred for 3 days at ambient temperature. Acetyl chloride (0.2 mL) was added slowly. The solution was then shaken for an additional 3 h and concentrated in vacuo. The residue was purified using pre-packed silica cartridges (methylene chloride to 10% ethyl acetate in methylene chloride). The residue was purified using pre-packed silica cartridges (8% ethyl acetate in methylene chloride to 10% methanol in methylene chloride) to give the title compounds.

General Procedure for the Alkylation of Diazepines at Position 1

Alkylating agent (1.5 equiv) was added to oven dried 2-dram vial equipped with a stir bar under nitrogen. The diazepine to be alkylated (1.0 equiv) was added, and the resulting mixture was dissolved in a solvent, such as DMF. Potassium carbonate (2.0 equiv.) was added, followed by addition of tetrebutylammonium iodide (catalytic). The reaction mixture was tightly capped and heated to 80° C. overnight. The reaction was filtered, concentrated down, and loaded onto a 1000 μm TLC plate. After elution twice with 10% EtOAc/hexanes, the lower band was isolated to give the 1-alkylated compounds.

General Procedure for the Synthesis of Amidines

A solution of 1,4-benzodiazepine-2,5-dione (0.181 mmol), 4-(N,N-dimethylamino)pyridine (122 mg, 1.0 mmol), and phosphorus oxychloride (350 μL, 1.4 mmol) in dichloroethane (4 mL) was stirred at 135° C. in a sealed tube for 2 h. After the solution was cooled to room temperature, the excess of phosphorus oxychloride was removed under vacuum. Then, the residue was dissolved in dry CH₂Cl₂ (6 mL), and amine (2–10 equiv) was added dropwise with stirring at 0° C. under argon. After 10 min, the reaction mixture was allowed to warm to room temperature. Then, the solvent was evaporated and the residue was chromatographed on silica (EtOAc/hexanes, 1:1) to give the title compounds as a colorless solid.

General Procedure for the Alternative Diazepine Synthesis #1

A solution of isatoic anhydride (1 mmol) and amino acid ester (1.3 mmol) in pyridine (3 mL) was stirred at 125° C. in a sealed tube for 1.5 h. After cooling to room temperature, the solvent was removed under vacuum. Chromatography on silica (EtOAc/hexanes, 1:1) afforded the appropriately substituted N-(2-aminobenzoyl)-2-(aryl)glycine methyl ester, which was dissolved in THF (10 mL). Then, potassium tert-butoxide (1M in THF, 1.1 mL) was slowly added, at −78° C. under argon atmosphere. The reaction mixture was allowed to warm up to room temperature. After 14 h., the reaction was quenched with acetic acid (150 μL), then the solvent was evaporated to dryness and the residue was diluted with ethyl acetate, washed with water, dried (Na2SO4), and concentrated to dryness under reduced pressure. Chromatography on silica (AcOEt/Hexane, 1:1) afforded the diazepine compound as colorless prisms. Alternatively, isatoic anhydride (10) was treated with a base such as NaH, in a solvent such as DMF at 0° C. to room temperature, followed by addition of a substituted halogen derivative to give (13). This was treated with an amino ester (1.5 equiv) at 80–120° C., followed by addition of t-BuOK at −20° C. to room temperature to give the title compound.

General procedure for the alternative diazepine synthesis #2

A solution of α-haloester (10 mmol), an optionally-substituted amine (10 mmol), $K_2CO_3$ (20 mmol) and TBAI (1.35 mmol) were stirred in acetonitrile at 45° C. for 12 hours. The crude mixture was extracted from water with ethyl acetate, followed by chromatography on silica (EtOAc:Hexane 5:95). The product (3.0 mmol) was treated with DIEA (11.5 mmol) in DCM (30 mL), followed by addition of an optionally-substituted α,β-unsaturated amine (3.25 mmol) at 0° C. The crude reaction was extracted from water with EtOAc, followed by chromatography on silica (Hexane: EtOAc 8:1) to give the corresponding product. This product (1.0 mmol) was saponified with NaOH (15.0 mmol) in THF and methanol at room temperature, followed by extraction from 1N HCl with EtOAc. The acid (0.88 mmol) was then treated with ammonium chloride (1.76 mmol), PyBrOP (1.32 mmol), HOBt (1.32 mmol) and DIEA (3.52 mmol) in DMF (3 mL) at room temperature and stirred for 2 hours. The crude mixture was extracted from water with EtOAc and purified by chromatography on silica (AcOEt: Hexane 1:3). The resulting amide (3.3 mmol) was stirred with silver triflate (6.6 mmol) in acetonitrile (120 mL) at room temperature. Benzeneselenyl bromide (6.53 mmol) was added in DMF (5.2 mL) and stirred for 2 hours. The crude residue was extracted from water with EtOAc and purified by chromatography (AcOEt:hexane 1:3). The corresponding product (0.49 mmol) was treated with hydrogen peroxide (500 μL, 30% in water) in THF at room temperature and stirred for 20 minutes. The crude mixture was extracted from 1N sodium hydrogencarbonate with EtOAc, followed by chromatography on silca (AcOEt:hexanes: DCM 1:2:2) to give the title compound.

General Procedure for the Dialkylation of Diazepines

A base, such as potassium carbonate (0.88 mmol) was added, at 20° C. to a stirred solution of diazepine (11) (0.82 mmol) in anhydrous DMF (4 mL). After 10 min., optionally-substituted alkyl halide (0.96 mmol) was added and stirring was continued for 1–12 h. at 25–70° C. Then, the reaction was diluted with ice-cold water (30 mL), and the residue filtered, washed with water, then dried in vacuo. Next, a base, such as $K_2CO_3$ (1.1 equiv) was added at 0° C. to this product in anhydrous solvent, such as DMF (2 mL). After 10 min., optionally-substituted alkyl halide (0.32 mmol) was added and stirring was continued for 5–24 h. at 25–80° C. Then, the reaction was quenched with acetic acid (50 μL). The crude material was purified by column chromatography on silica (EtOAc/hexane, 1.1). Recrystallization from ethanol/ether yielded the compound 12 as colorless crystals.

Example 1

5-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-yl}-pentanoic acid

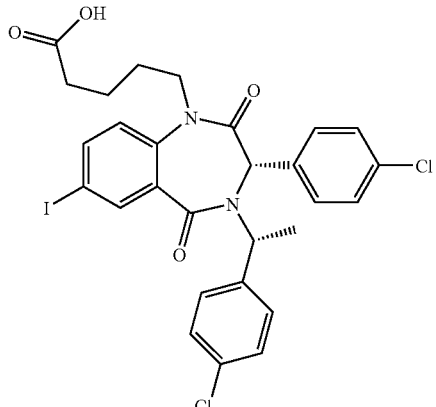

a) 5-{(3S)-3-(4-Chlorophenyl)-4-[(R)-1-(4-chlorophenyl)-ethyl]-7-2,5-dioxo-2,3,4,5-tetrahydro-benzo[e][1,4]diazepin-1-yl}-pentanoic acid tert-butyl ester The title compound was synthesized following the general procedure for the conventional synthesis of diazepine compounds followed by the general procedure for the alkylation of diazepines at position 1: Mass spectrum (LCMS, ESI pos.): Calcd for $C_{32}H_{33}Cl_2IN_2O_4$: 706.09; found 707.1 (M+H).

b) 5-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-yl}-pentanoic acid 5-{(3S)-3-(4-Chloro-phenyl)-4-[(R)-1-(4-chloro-phenyl)-ethyl]-7-iodo-2,5-dioxo-2,3,4,5-tetrahydro-benzo[e][1,4]diazepin-1-yl}-pentanoic acid tert-butyl ester (1.0 g, 1.4 mmol) was dissolved in a solution of 20% TFA [10 mL] in dichloromethane at room temperature for 2 hours. The reaction was concentrated and the product was purified by chromatography (hexane: EtOAc 1:1) to give the title compound (0.88 g, 96%). $^1$H NMR (400 MHz, DMSO-d$_6$) δ 7.75 (d, J=2.3 Hz. 1H), 7.62–7.56 (m, 3H), 7.39 (d, J=8.6 Hz, 2H), 7.00 (d, J=8.6 Hz, 2H), 6.92 (d, J=8.6 Hz, 1H), 6.58–6.56 (m, 2H), 6.21–6.14 (m, 1H), 5.27 (s, 1H), 4.24–4.15 (m, 1H), 3.69–3.61 (m, 1H), 1.80 (t, J=7.2 Hz, 2H), 1.63 (d, J=7.2 Hz, 3H), 1.56–1.21 (m, 4H). Mass spectrum (LCMS, ESI pos.): Calcd for $C_{28}H_{25}Cl_2IN_2O_4$: 650.02; found 650.8(M+H).

Example 2

5-{(3S)-3-(4-Chlorophenyl)-4-[(R)-1-(4-chlorophenyl)-ethyl]-7-ethynyl-2,5-dioxo-2,3,4,5-tetrahydro-benzo[e][1,4]diazepin-1-yl}-pentanoic acid

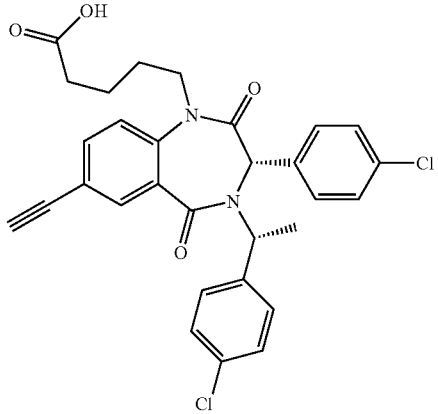

¹H NMR (400 MHZ, DMSO-D₆) δ 7.60 (D, J=8.6 HZ, 2H), 7.53 (D, J=2.1 HZ, 1H), 7.42–7.33 (M, 3H), 7.12 (D, J=8.6 HZ, 1H), 6.99 (D, J=8.4 HZ, 2H), 6.57 (D, J=7.7 HZ, 2H), 6.23–6.15 (M, 1H), 5.29 (S, 1H), 4.31–4.22 (M, 2H), 3.78–3.68 (M, 1H), 2.20–2.12 (M, 2H), 1.63 (D, J=7.0 HZ, 3H), 1.41–1.38 (M, 2H), 1.27–1.22 (M, 2H). MASS SPECTRUM (LCMS, ESI POS.): CALCD FOR C₃₀H₂₆CL₂N₂O₄: 548.13; FOUND 548.9 (M+H).

Example 3

5-[4-[(R)-1-(4-Chlorophenyl)-ethyl]-7-iodo-2,5-dioxo-(3S)-3-(4-trifluoromethyl-phenyl)-2,3,4,5-tetrahydro-benzo[e][1,4]diazepin-1-yl]-pentanoic acid

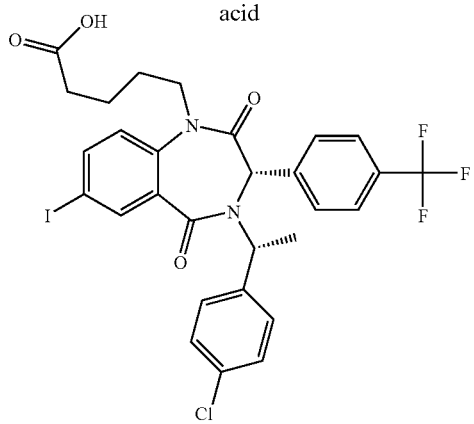

¹H NMR (400 MHz, CDCl₃) δ 7.94 (d, J=2.1 Hz, 1H), 7.50 (d, J=8.4 Hz, 2H), 7.44 (dd, J=8.6 Hz, 2.1 Hz, 1H), 7.33 (d, J=8.6 Hz, 2H), 7.18 (d, J=8.4 Hz, 2H), 6.68 (d, J=8.4 Hz, 2H), 6.57 (d, J=8.6 Hz, 2H), 6.46–6.39 (m, 1H), 5.39 (s, 1H), 4.39–4.31 (m, 1H), 3.70–3.62 (m, 1H), 2.37 (t, J=7.0 Hz, 2H), 1.75 (d, J=7.2 Hz, 3H), 1.67–1.58 (m, 4H). Mass spectrum (LCMS, ESI pos.): Calcd for C₂₉H₂₅ClF₃IN₂O₄: 684.05; found 684.8 (M+H).

Example 4

5-[4-[(R)-1-(4-Chlorophenyl)-ethyl]-7-iodo-2,5-dioxo-(3S)-3-(4-trifluoromethoxy-phenyl)-2,3,4,5-tetrahydro-benzo[e][1,4]diazepin-1-yl]-pentanoic acid

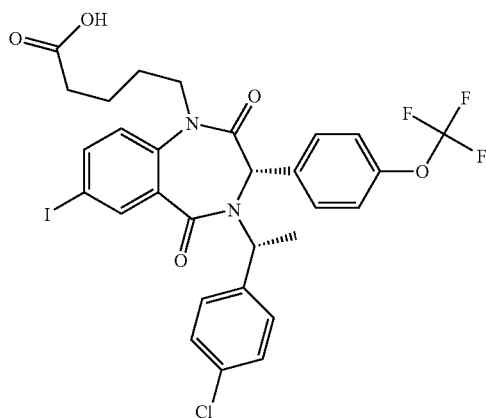

¹H NMR (400 MHz, CDCl₃) δ 7.89 (d, J=2.1 Hz, 1H), 7.48 (d, J=8.4 Hz, 2H), 7.43 (dd, J=8.6 Hz, 2.1 Hz, 1H), 7.32 (d, J=8.6 Hz, 2H), 6.75 (d, J=8.4 Hz, 2H), 6.59–6.53 (m, 3H), 6.42–6.35 (m, 1H), 5.36 (s, 1H), 4.41–4.31 (m, 1H), 3.67–3.57 (m, 1H), 2.37 (t, J=7.0 Hz, 2H), 1.73 (d, J=7.2 Hz, 3H), 1.67–1.52 (m, 4H). Mass spectrum (LCMS, ESI pos.): Calcd for C₂₉H₂₅ClF₃IN₂O₅: 700.04; found 700.86 (M+H).

Example 5

6-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-yl}-hexanoic acid

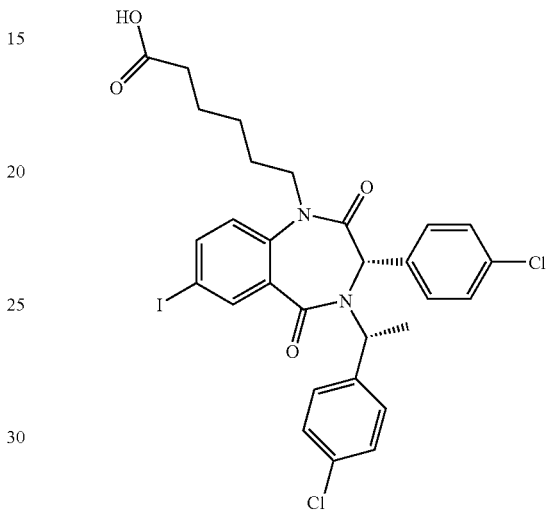

¹H NMR (400 MHz, DMSO-d₆) δ 7.78–7.74 (m, 1H), 7.62–7.55 (m, 2H), 7.42–7.39 (m, 3H), 7.02–6.99 (m, 2H), 6.93 (d, J=8.6 Hz, 2H), 6.58 (d, 7.7 Hz, 2H), 6.28–6.14 (m, 1H), 5.28 (s, 1H), 4.29–4.19 (m, 1H), 3.71–3.62 (m, 1H), 2.15–2.07 (m, 2H), 1.65–1.58 (m, 3H), 1.50–0.96 (m, 6H). Mass spectrum (LCMS, ESI pos.): Calcd for C₂₉H₂₇Cl₂IN₂O₄: 664.04; found 664.8 (M+H).

Example 6

7-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-yl}-heptanoic acid

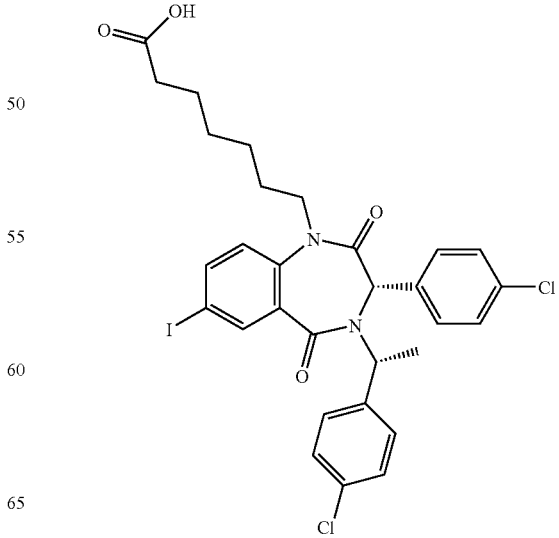

¹H NMR (400 MHz, DMSO-d₆) δ 7.77–7.75 (m, 1H), 7.63–7.55 (m, 2H), 7.45–7.37 (m, 3H), 7.03–6.98 (m, 2H), 6.93–6.83 (m, 1H), 6.58 (d, J=8.6 Hz, 2H), 6.28–6.13 (m, 1H), 5.28 (s, 1H), 4.30–4.23 (m, 1H), 3.69–3.62 (m, 1H), 2.14 (t, J=7.44 Hz, 2H), 1.64–1.59 (m, 3H), 1.54–0.97 (m, 8H). Mass spectrum (LCMS, ESI pos.): Calcd for C₃₀H₂₉Cl₂IN₂O₄: 678.05; found 678.9 (M+H).

Example 7

4-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-ylmethyl}-benzoic acid

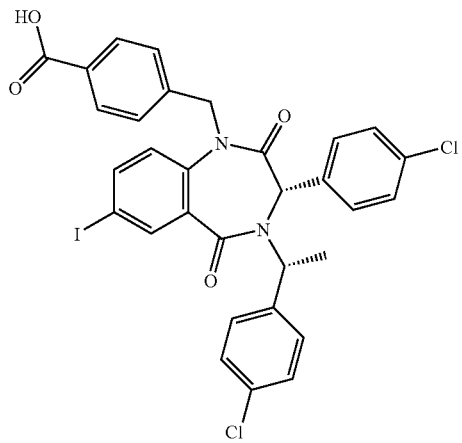

¹H NMR (400 MHz, DMSO-d₆) δ 8.12–7.91 (m, 3H), 7.47–7.37 (m, 3H), 7.33–7.24 (m, 3H), 7.18–7.02 (m, 1H), 6.97–6.85 (m, 2H), 6.61–6.50 (m, 3H), 6.45–6.33 (m, 1H), 5.37 (s, 1H), 5.35 (d, J=15.6 Hz, 1H), 4.99 (d, J=15.8 Hz, 1H), 1.64 (d, J=7.2 Hz, 3H). Mass spectrum (LCMS, ESI pos.): Calcd for C₃₁H₂₃Cl₂IN₂O₄: 684.01; found 684.7 (M+H).

Example 8

4-{(3S)-3-(4-Chlorophenyl)-4[(R)-1-(4-chlorophenyl)-ethyl]-7-iodo-2,5-dioxo-2,3,4,5-tetrahydro-benzo[e][1,4]diazepin-1-yl}-butyric acid

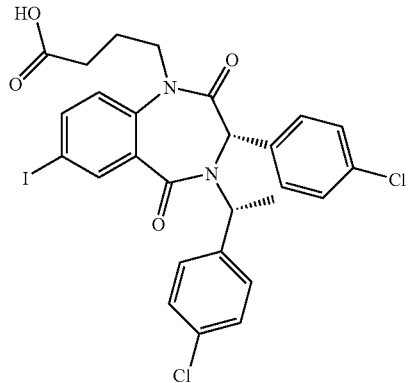

¹H NMR (400 MHz, DMSO-d₆) δ 7.76, (d, J=2.1 Hz, 1H), 7.61–7.58 (m, 2H), 7.41–7.39 (m, 2H), 7.00 (d, J=8.8 Hz, 2H), 6.94–6.86 (m, 1H), 6.60–6.50 (m, 2H), 6.29–6.14 (m, 1H), 5.29 (s, 1H), 4.30–4.20 (m, 1H), 3.75–3.66 (m, 1H), 2.13 (t, J=7.2 Hz, 2H), 1.85–1.70 (m, 1H), 1.65 (d, J=7.21, 3H), 1.64–1.54 (m, 2H). Mass spectrum (LCMS, ESI pos.): Calcd for C₂₇H₂₃Cl₂IN₂O₄: 636.01; found 636.8 (M+H).

Example 9

3-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-yl}-propionic acid

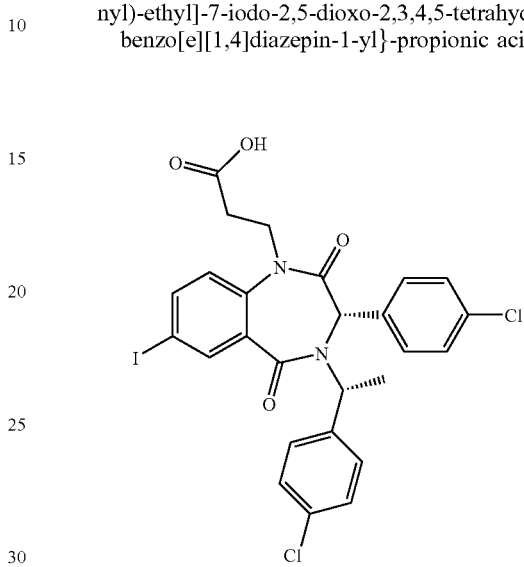

¹H NMR (400 MHz, DMSO-d₆) δ 7.73 (d, J=2.1 Hz, 1H), 7.64–7.35 (m, 5H), 7.21–6.96 (m, 2H), 6.97–6.49 (m, 3H), 6.28–6.14 (m, 1H), 5.25 (s, 1H), 4.51–4.31 (m, 1H), 3.94–3.80 (m, 1H), 2.44–2.29 (m, 1H), 1.91 (s, 1H), 1.68–1.57 (m, 3H). Mass spectrum (LCMS, ESI pos.): Calcd for C₂₆H₂₁Cl₂IN₂O₄: 621.99; found 622.8 (M+H).

Example 10

5-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-ylmethyl}-furan-2-carboxylic acid

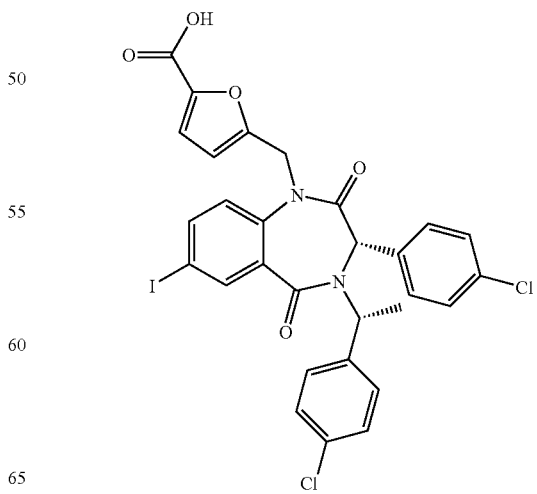

¹H NMR (400 MHz, CDCl₃) δ 8.04–7.85 (m, 1H), 7.58 (d, J=8.4 Hz, 1H), 7.70–7.44 (m, 2H), 7.39–7.30 (m, 3H), 7.10 (d, J=7.7 Hz, 1H), 6.91 (d, J=8.1 Hz, 2H), 6.74 (d, J=8.6 Hz, 1H), 6.54 (d, J=3.2 Hz, 1H), 6.47 (d, J=8.1 Hz, 2H), 5.55 (s, 1H), 5.27–4.90 (m, 2H), 1.82–1.66 (m, 3H). Mass spectrum (LCMS, ESI pos.): Calcd for $C_{29}H_{21}Cl_2IN_2O_5$: 673.99; found 674.8 (M+H).

Example 11

5-{(3S)-8-Chloro-3-(4-chloro-phenyl)-4-[(R)-1-(4-chlorophenyl)-ethyl]-7-iodo-2,5-dioxo-2,3,4,5-tetrahydro-benzo[e][1,4]diazepin-1-yl}-pentanoic acid

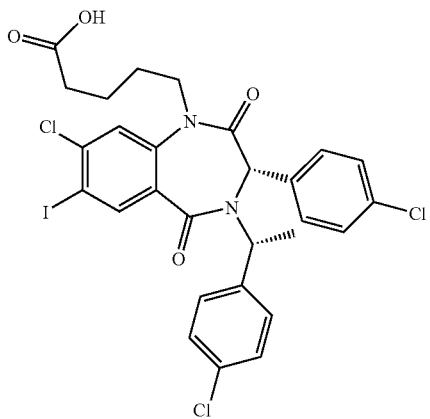

¹H NMR (400 MHz, CDCl₃) δ 8.08 (s, 1H), 7.46 (d, J=8.4 Hz, 2H), 7.30 (d, J=8.4 Hz, 2H), 6.95–6.88 (m, 3H), 6.45 (d, J=7.7 Hz, 2H), 6.40–6.34 (m, 1H), 5.33 (s, 1H), 4.39–4.27 (m, 1H), 3.69–3.59 (m, 1H), 2.45–2.34 (m, 2H), 1.70 (d, J=7.2 Hz, 3H), 1.67–1.52 (m, 4H). Mass spectrum (LCMS, ESI pos.): Calcd for $C_{28}H_{24}Cl_3IN_2O_4$: 683.98; found 684.8 (M+H).

Example 12

5-{3-(4-Chlorophenyl)-4-[(4-chlorophenyl)-cyclopropyl-methyl]-7-iodo-2,5-dioxo-2,3,4,5-tetrahydro-benzo[e][1,4]diazepin-1-yl}-pentanoic acid

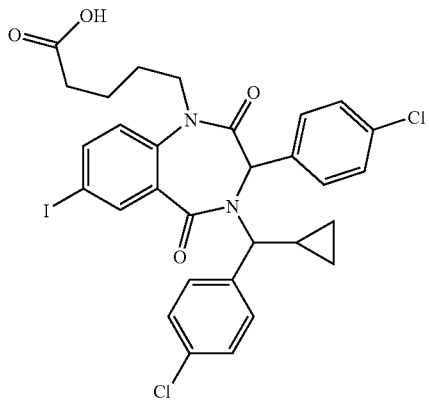

¹H NMR (400 MHz, DMSO-d₆) δ 7.74 (d, J=2.1 Hz, 1H), 7.66 (d, J=8.4 Hz, 2H), 7.59 (dd, J=8.6 Hz, 2.1 Hz, 1H), 7.40 (d, J=8.6 Hz, 2H), 7.01 (d, J=8.8 Hz, 2H), 6.92 (d, J=8.8 Hz, 1H), 6.59 (dd, J=8.6 Hz, 0.93 Hz, 2H), 5.51 (s, 1H), 5.16 (d, J=10.7 Hz, 1H), 4.38–4.29 (m, 1H), 3.71–3.62 (m, 1H), 2.19–2.11 (m, 2H), 1.91–1.81 (m, 1H), 1.54–1.21 (m, 4H), 0.81–0.71 (m, 1H), 0.62–0.52 (m, 1H), 0.48–0.34 (m, 2H). Mass spectrum (LCMS, ESI pos.): Calcd for $C_{30}H_{27}Cl_2IN_2O_4$: 676.04; found 677.0 (M+H).

Example 13

5-{3-(4-Chlorophenyl)-4-[1-(3,4-dichlorophenyl)-ethyl]-7-iodo-2,5-dioxo-2,3,4,5-tetrahydro-benzo[e][1,4]diazepin-1-yl}-pentanoic acid

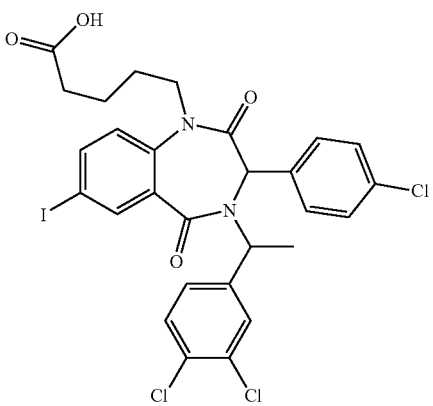

¹H NMR (400 MHz, DMSO-d₆) δ 7.85–7.76 (m, 2H), 7.63–7.55 (m, 3.0H), 7.02 (d, J=8.6 Hz, 2H), 6.90 (d, J=8.6 Hz, 1H), 6.63 (d, J=8.6 Hz, 2H), 6.13–6.06 (m, 1H), 5.38 (s, 1H), 4.31 (m, 1H), 3.72–3.64 (m, 1H), 2.18–2.11 (m, 2H), 1.65 (d, J=6.9 Hz, 3H), 1.55–1.43 (m, 1H), 1.48–1.28 (m, 3H). Mass spectrum (LCMS, ESI pos.): Calcd for $C_{28}H_{24}Cl_3IN_2O_4$: 683.98; found 684.8 (M+H).

Example 14

5-[4-[1-(3-Amino-4-chlorophenyl)-ethyl]-3-(4-chlorophenyl)-7-iodo-2,5-dioxo-2,3,4,5-tetrahydro-benzo[e][1,4]diazepin-1-yl]-pentanoic acid

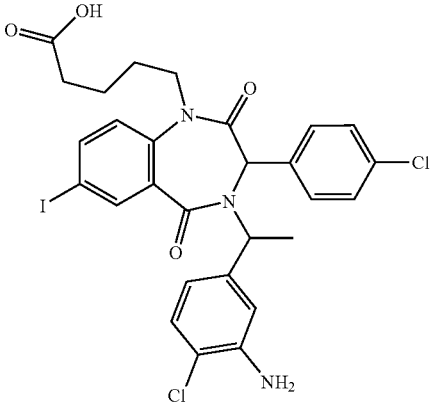

¹H NMR (400 MHz, DMSO-d₆) δ 7.74 (d, J=2.1 Hz, 1H), 7.59 (dd, J=8.6 Hz, 2.1 Hz, 1H), 7.12 (d, J=8.1 Hz, 1H), 7.03–6.98 (m, 3H), 6.92 (d, J=8.6 Hz, 2H), 6.70 (dd, J=8.6 Hz, 2.1 Hz, 2H), 6.63 (d, J=8.6 Hz, 2H), 6.13–6.04 (m, 1H), 5.41 (s, 2H), 5.19 (s, 1H), 4.33–4.22 (m, 1H), 3.73–3.63 (m, 1H), 2.19–2.12 (m, 2H), 1.57–1.45 (m, 3H), 1.44–1.31 (m, 3H). Mass spectrum (LCMS, ESI pos.): Calcd for $C_{28}H_{26}Cl_2IN_3O_4$: 665.03; found 665.8 (M+H).

Example 15

5-[4-[1-(4-Chloro-3-nitro-phenyl)-ethyl]-3-(4-chlorophenyl)-7-iodo-2,5-dioxo-2,3,4,5-tetrahydro-benzo[e][1,4]diazepin-1-yl]-pentanoic acid

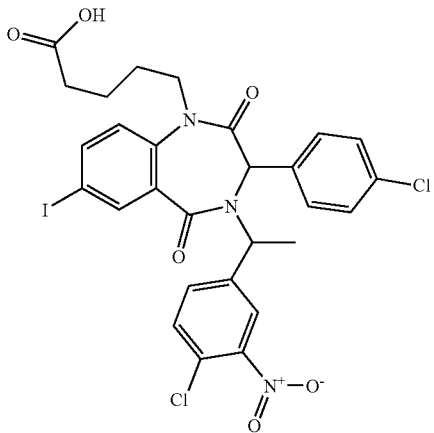

$^1$H NMR (400 MHz, DMSO-d$_6$) δ 8.24 (d, J=2.1 Hz, 1H), 7.90 (dd, J=8.6 Hz, 2.3 Hz, 1H), 7.78 (d, J=2.1 Hz, 1H), 7.73 (d, J=8.4 Hz, 1H), 7.58 (dd, J=8.6 Hz, 2.1 Hz, 1H), 7.01 (d, J=8.6 Hz, 2H), 6.90 (d, J=8.8 Hz, 1H), 6.66–6.63 (m, 2H), 6.20–6.13 (m, 1H), 5.43 (s, 1H), 4.29–4.20 (m, 1H), 3.72–3.63 (m, 1H), 2.19–2.11 (m, 2H), 1.69 (d, J=7.2 Hz, 3H), 1.53–1.44 (m, 1H), 1.41–1.32 (m, 3H). Mass spectrum (LCMS, ESI pos.): Calcd for $C_{28}H_{24}Cl_2IN_3O_6$: 695.01; found 695.8 (M+H).

Example 16

5-{3-(4-Chlorophenyl)-7-iodo-4-[1-(4-methyl-naphthalen-1-yl)-ethyl]-2,5-dioxo-2,3,4,5-tetrahydro-benzo[e][1,4]diazepin-1-yl}-pentanoic acid

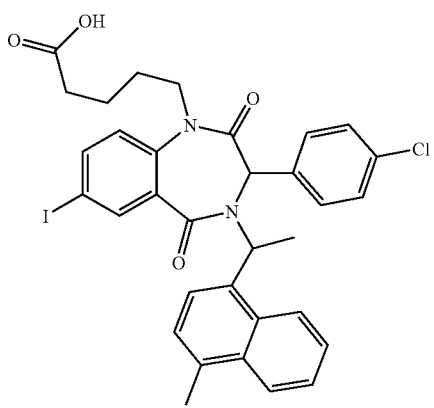

$^1$H NMR (400 MHz, DMSO-d$_6$) δ 8.39 (d, J=8.8 Hz, 1H), 8.06 (d, J=8.4 Hz, 1H), 7.87–7.76 (m, 2H), 7.70–7.55 (m, 3H), 7.35 (d, J=8.1 Hz, 1H), 6.90 (d, J=8.6 Hz, 2H), 6.64 (d, J=8.6 Hz, 2H), 6.18–6.13 (m, 2H), 5.18 (s, 1H), 4.37–4.27 (m, 1H), 3.73–3.64 (m, 1H), 2.58 (s, 3H), 2.23–2.15 (m, 2H), 1.75 (d, J=7.0 Hz, 3H), 1.54–1.30 (m, 4H). Mass spectrum (LCMS, ESI pos.): Calcd for $C_{33}H_{30}ClIN_2O_4$: 680.09; found 680.8 (M+H).

Example 17

5-[4-(4-Chlorobenzyl)-3-(4-chlorophenyl)-7-iodo-2,5-dioxo-2,3,4,5-tetrahydro-benzo[e][1,4]diazepin-1-yl]-pentanoic acid

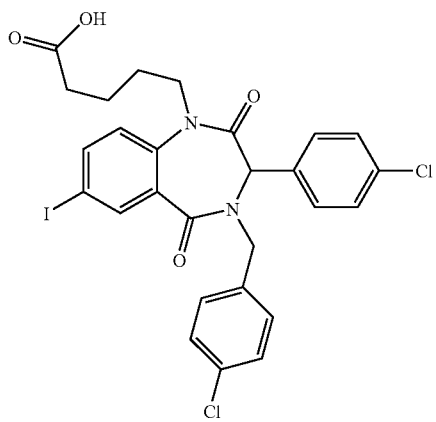

$^1$H NMR (400 MHz, DMSO-d$_6$) δ 12.05-(bs, 1H), 7.71 (d, J=2.1 Hz, 1H), 7.62 (dd, J=8.8 Hz, 2.3 Hz, 1H), 7.43 (m, 4H), 7.17 (d, J=8.6 Hz, 2H), 6.95 (d, J=8.8 Hz, 1H), 6.83 (d, J=7.7 Hz, 2H), 5.70 (s, 1H), 5.27 (d, J=14.6 Hz, 1H), 4.69 (d, J=14.4 Hz, 1H), 4.21–4.13 (m, 1H), 3.67–3.58 (m, 1H), 2.11 (t, J=7.0 Hz, 2H), 1.32–1.22 (m, 2H), 0.88–0.83 (m, 2H). Mass spectrum (LCMS, ESI pos.): Calcd for $C_{27}H_{23}Cl_2IN_2O_4$: 636.01; found 637.0 (M+H).

Example 18

5-{3-(4-Chlorophenyl)-4-[2-(4-chlorophenyl)-1-methyl-ethyl]-7-iodo-2,5-dioxo-2,3,4,5-tetrahydro-benzo[e][1,4]diazepin-1-yl}-pentanoic acid

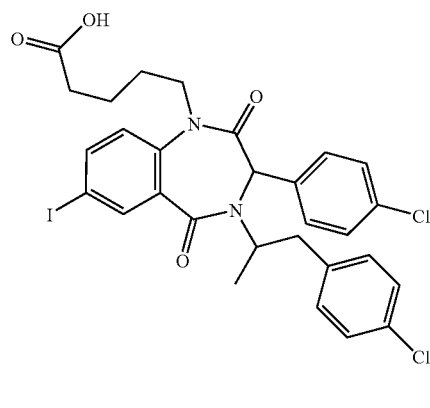

$^1$H NMR (400 MHz, DMSO-d$_6$) δ 7.71–7.65 (m, 1H), 7.60–7.53 (m, 1H), 7.39–7.24 (m, 4H), 7.17–7.04 (m, 2H), 6.92–6.71 (m, 3H), 5.74 (s, 1H), 5.34–5.14 (m, 1H), 4.25–3.99 (m, 1H), 3.70–3.59 (m, 1H), 3.12 (m, 1H), 2.98–2.86 (m, 1H), 2.18–2.09 (m, 2H), 1.52–1.13 (m, 7H). Mass spectrum (LCMS, ESI pos.): Calcd for $C_{29}H_{27}Cl_2IN_2O_4$: 664.04; found 664.9 (M+H).

Example 19

5-{(3S)-3-(3-Bromo-phenyl)-4-[(R)-1-(4-chlorophenyl)-ethyl]-7-iodo-2,5-dioxo-2,3,4,5-tetrahydro-benzo[e][1,4]diazepin-1-yl}-pentanoic acid

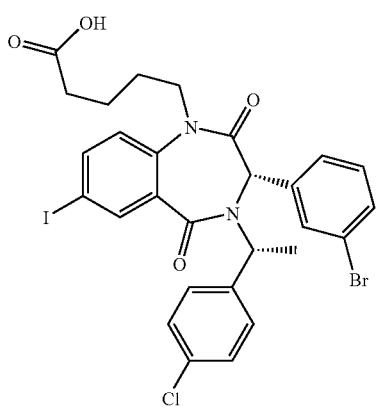

$^1$H NMR (400 MHz, DMSO-$d_6$) δ 7.95 (d, J=2.1 Hz, 1H), 7.51–7.44 (m, 3H), 7.37–7.29 (m, 2H), 7.08–7.03 (m, 1H), 6.81–6.71 (m, 1H), 6.65–6.61 (m, 1H), 6.59 (d, J=8.8 Hz, 1H), 6.48–6.42 (m, 1H), 6.43–6.35 (m, 1H), 5.33 (s, 1H), 4.41–4.32 (m, 1H), 3.67–3.57 (m, 1H), 2.40–2.34 (m, 2H), 1.72 (d, J=7.2 Hz, 3H), 1.67–1.54 (m, 4H). Mass spectrum (LCMS, ESI pos.): Calcd for $C_{28}H_{25}BrClIN_2O_4$: 695.78; found 696.8 (M+H).

Example 20

[4-Benzyl-3-(4-chlorophenyl)-7-iodo-2,5-dioxo-2,3,4,5-tetrahydro-benzo[e][1,4]diazepin-1-yl]-acetic acid

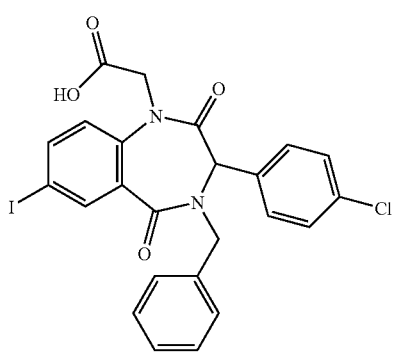

$^1$H NMR (400 MHz, CD$_3$OD) δ 7.80 (d, J=2.1 Hz, 1H), 7.58–7.47 (m, 3H), 7.42–7.28 (m, 3H), 6.99 (s, 4H), 6.89 (d, J=8.8 Hz, 1H), 5.51 (s, 1H), 5.49 (s, 1H), 5.18 (d, J=14.4 Hz, 1H), 4.57 (d, J=17.0 Hz, 1H), 4.13 (d, J=17.2 Hz, 1H). Mass spectrum (LCMS, ESI pos.): Calcd for $C_{24}H_{18}ClIN_2O_4$: 560.00; found 561.1 (M+H).

Example 21

5-{(3S)-3-(4-Chloro-3-nitro-phenyl)-4-[(R)-1-(4-chlorophenyl)-ethyl]-7-iodo-2,5-dioxo-2,3,4,5-tetrahydro-benzo[e][1,4]diazepin-1-yl}-pentanoic acid

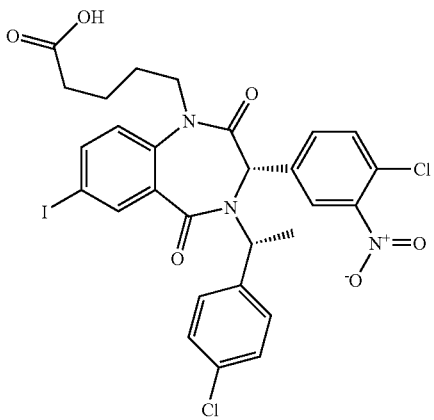

$^1$H NMR (400 MHz, CDCl$_3$) δ 8.06–7.96 (m, 1H), 7.55–7.44 (m, 3H), 7.39–7.28 (m, 3H), 7.13–7.04 (m, 2H), 6.70–6.54 (m, 1H), 6.46–6.36 (m, 1H), 5.30 (s, 1H), 4.40–4.07 (m, 1H), 3.70–3.38 (m, 1H), 2.45–2.24 (m, 2H), 1.98–1.77 (m, 1H), 1.72 (d, J=7.0 Hz, 3H), 1.64–1.54 (m, 3H). Mass spectrum (LCMS, ESI pos.): Calcd for $C_{28}H_{24}Cl_2IN_3O_6$: 695.01; found 695.7 (M+H).

Example 22

5-{(3S)-7-Acetyl-3-(4chlorophenyl)-4-[(R)-1-(4-chlorophenyl)-ethyl]-2,5-dioxo-2,3,4,5-tetrahydro-benzo[e][1,4]diazepin-1-yl}-pentanoic acid

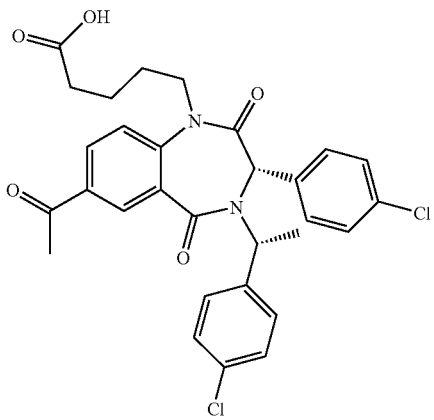

$^1$H NMR (400 MHz, DMSO-$d_6$) δ 8.05 (d, J=2.3 Hz, 1H), 7.79 (dd, J=8.6 Hz, 2.3 Hz, 1H), 7.62 (d, J=8.6 Hz, 2H), 7.41 (m, 2H), 7.25 (d, J=8.8 Hz, 1H), 6.96 (d, J=8.6 Hz, 2H), 6.59 (d, J=8.6 Hz, 2H), 6.21 (m, 1H), 5.35 (s, 1H), 4.36–4.26 (m, 1H), 3.84–3.74 (m, 1H), 2.21–2.13 (m, 2H), 1.66 (d, J=7.2 Hz, 3H), 1.46–1.33 (m, 3H), 1.30–1.20 (m, 4H). Mass spectrum (LCMS, ESI pos.): Calcd for $C_{30}H_{28}Cl_2N_2O_5$: 566.14; found 566.9 (M+H).

Example 23

5-{(3S)-3-(3-Amino-4-chloro-phenyl)-4-[(R)-1-(4-chloro-phenyl)-ethyl]-7-iodo-2,5-dioxo-2,3,4,5-tetrahydro-benzo[e][1,4]diazepin-1-yl}-pentanoic acid

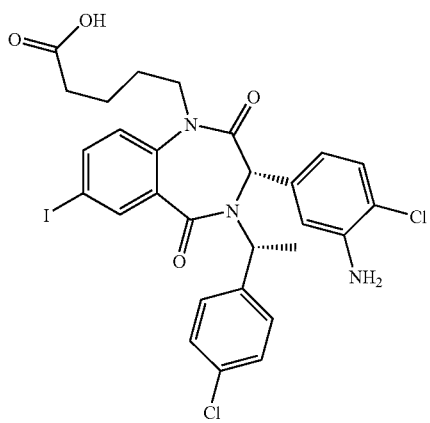

¹H NMR (400 MHz, CDCl₃) δ 8.13–7.84 (m, 1H), 7.61–7.27 (m, 4H), 7.01–6.81 (m, 1H), 6.76–6.64 (m, 1H), 6.66–5.63 (m, 5H), 5.38–5.10 (m, 2H), 4.41–3.89 (m, 2H), 3.62–3.27 (m, 3H), 1.79–1.32 (m, 6H). Mass spectrum (LCMS, ESI pos.): Calcd for $C_{28}H_{26}Cl_2IN_3O_4$: 665.03; found 665.8 (M+H).

Example 24

(3S)-2-Amino-3-(4-chlorophenyl)-4-[(R)-1-(4-chlorophenyl)-ethyl]-7-iodo-3,4-dihydro-benzo[e][1,4]diazepin-5-one

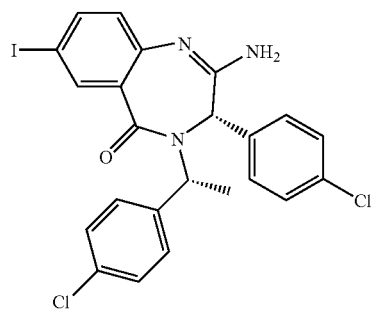

¹H NMR (400 MHZ, CDCl₃) δ 1.76 (D, J=5.5 HZ, 3H, CH₃), 5.10 (BR S, 1H, CH), 6.46 (Q, J=5.5 HZ, 1H, CH), 6.53 (D, J=6.3 HZ, 1H, ARH), 6.58 (D, J=6.0 HZ, 2H, ARH), 6.91 (D, J=6.6 HZ, 2H, ARH), 7.33 (D, J=6.6 HZ, 2H, ARH), 7.41 (DD, J=6.3 HZ, J=1.5 HZ, 1H, ARH), 7.53 (D, J=6.6 HZ, 2H, ARH), 8.03 (D, J=1.5 HZ, 1H, ARH). MASS SPECTRUM (LCMS, ESI POS.): CALCD FOR $C_{23}H_{18}Cl_2IN_3O$: 548.99; FOUND 551.0 (M+H).

Example 25

2-{(3S)-3-(4-Chlorophenyl)-4-[(R)-1-(4-chlorophenyl)-ethyl]-7-iodo-5-oxo-4,5-dihydro-3H-benzo[e][1,4]diazepin-2-ylamino}-acetamide

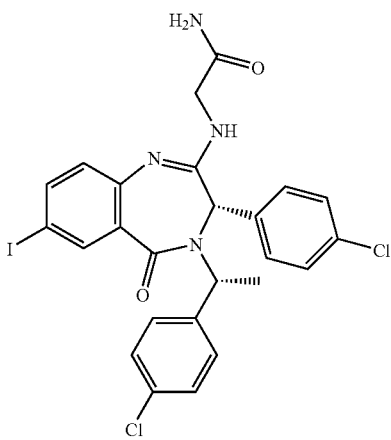

¹H NMR (400 MHz, CDCl₃) δ 1.76 (d, J=5.4 Hz, 3H, CH₃), 4.26–4.40 (m, 2H, CH₂), 5.09 (br s, 1H, CH), 5.68 (br s, 1H, NH), 6.30 (br s, 1H, NH), 6.44 (q, J=5.4 Hz, 1H, CH), 6.53–6.58 (m, 3H, ArH), 6.87 (d, J=6.3 Hz, 2H, CH₂), 7.31–7.40 (m, 3H, ArH), 7.53 (d, J=6.3 Hz, 2H, ArH), 8.00 (d, J=1.5 Hz, 1H, ArH). Mass spectrum (LCMS, ESI pos.): Calcd for $C_{25}H_{21}Cl_2IN_4O_2$: 606.01; found 607.0 (M+H).

Example 26

(3S)-3-(4-Chloro-phenyl)-4-[(R)-1-(4-chloro-phenyl)-ethyl]-2-(2-hydroxy-ethylamino)-7-iodo-3,4-dihydro-benzo[e][1,4]diazepin-5-one

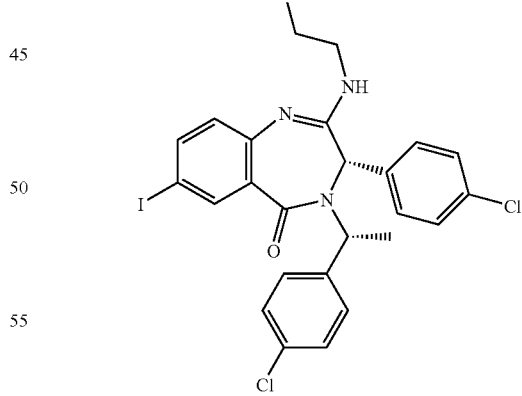

¹H NMR (400 MHz, CDCl₃) δ 1.71 (d, J=5.4 Hz, 3H, CH₃), 3.76–3.79 (m, 2H, CH₂), 3.95–3.98 (m, 2H, CH₂), 4.96 (s, 1H, CH), 6.43 (q, J=5.4 Hz, 1H, CH), 6.54–6.56 (m, 3H, ArH), 6.89 (d, J=6.6 Hz, 2H, ArH), 7.31 (d, J=6.3 Hz, 2H, ArH), 7.38 (dd, J=6.3 Hz, J=1.5 Hz, 1H, ArH), 7.50 (d, J=6.3 Hz, 2H, ArH), 7.98 (d, J=1.5 Hz, 1H, ArH). Mass spectrum (LCMS, ESI pos.): Calcd for $C_{25}H_{22}Cl_2IN_3O_2$: 593.01; found 594.0 (M+H).

Example 27

(3S)-3-(4-Chloro-phenyl)-4-[(R)-1-(4-chloro-phenyl)-ethyl]-2-(3-hydroxy-propylamino)-7-iodo-3,4-dihydro-benzo[e][1,4]diazepin-5-one

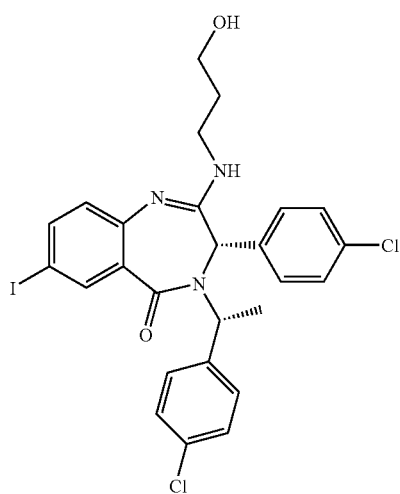

$^1$H NMR (400 MHz, CDCl$_3$) δ 1.72 (d, J=5.1 Hz, 3H, CH$_3$), 1.91–1.95 (m, 2H, CH$_2$), 3.78–3.86 (m, 4H, 2 CH$_2$), 4.89 (s, 1H, CH), 6.45 (q, J=5.1 Hz, 1H, CH), 6.54 (d, J=6.0 Hz, 2H, ArH), 6.58 (d, J=6.6 Hz, 1H, ArH), 6.91 (d, J=6.3 Hz, 2H, ArH), 7.32 (d, J=6.0 Hz, 2H, ArH), 7.37–7.39 (m, 1H, ArH), 7.49 (d, J=6.3 Hz, 2H, ArH), 7.98 (d, J=1.5 Hz, 1H, ArH). Mass spectrum (LCMS, ESI pos.): Calcd for C$_{26}$H$_{24}$Cl$_2$IN$_3$O$_2$: 607.03; found 608.0 (M+H).

Example 28

N-(2-{(3S)-3-(4-Chloro-phenyl)-4-[(R)-1-(4-chloro-phenyl)-ethyl]-7-iodo-5-oxo-4,5-dihydro-3H-benzo[e][1,4]diazepin-2-ylamino}-ethyl)-acetamide

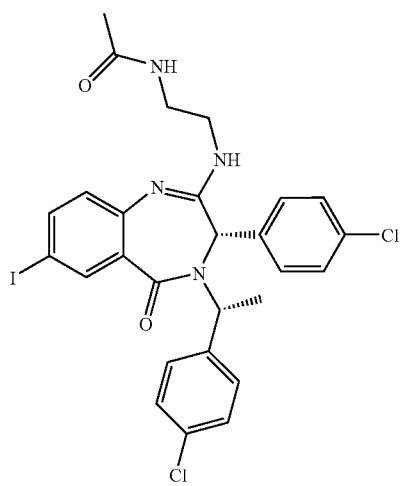

$^1$H NMR (400 MHz, CDCl$_3$) δ 1.72 (d, J=5.1 Hz, 3H, CH$_3$), 2.24 (s, 3H, CH$_3$), 3.47–3.90 (m, 4H, 2 CH$_2$), 6.08 (s, 1H, CH), 6.54-(q, J=5.1 Hz, 1H, CH), 6.91 (d, J=6.0 Hz, 2H, CH$_3$), 7.15–7.18 (m, 3H, ArH), 7.37 (d, J=6.0 Hz, 2H, CH$_2$), 7.53–7.55 (m, 3H, ArH), 8.13 (d, J=1.5 Hz, 1H, ArH). Mass spectrum (LCMS, ESI pos.): Calcd for C$_{27}$H$_{25}$Cl$_2$N$_4$O$_2$: 634.04; found 635.1 (M+H).

Example 29

(3S)-3-(4-Chloro-phenyl)-4-[(R)-1-(4-chloro-phenyl)-ethyl]-7-iodo-2-methylamino-3,4-dihydro-benzo[e][1,4]diazepin-5-one

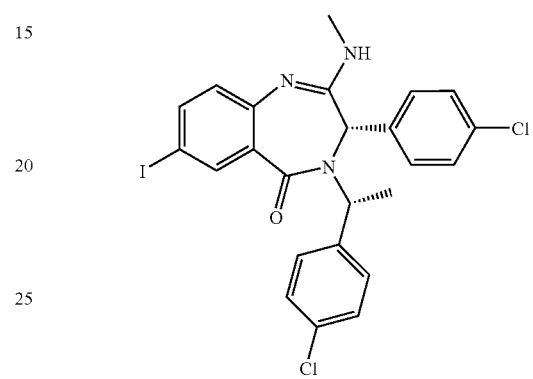

$^1$H NMR (400 MHz, CDCl$_3$) δ 1.67 (d, J=5.1 Hz, 3H, CH$_3$), 3.17 (s, 3H, CH$_3$), 4.85 (br s, 1H, CH), 6.42 (q, J=5.1 Hz, 1H, CH), 6.53 (d, J=6.3 Hz, 2H, ArH), 6.60 (d, J=6.3 Hz, 1H, ArH), 6.89 (d, J=6.3 Hz, 2H, ArH), 7.31 (d, J=6.3 Hz, 2H, ArH), 7.38 (dd, J=6.3 Hz, J=1.5 Hz, 1H, ArH), 7.47 (d, J=6.3 Hz, 2H, ArH), 7.97 (d, J=1.5 Hz, 1H, ArH). Mass spectrum (LCMS, ESI pos.): Calcd for C$_{24}$H$_{20}$Cl$_2$IN$_3$O: 563.00; found 563.9 (M+H).

Example 30

2-(2-Amino-ethylamino)-(3S)-3-(4-chloro-phenyl)-4-[(R)-1-(4-chloro-phenyl)-ethyl]-7-iodo-3,4-dihydro-benzo[e][1,4]diazepin-5-one

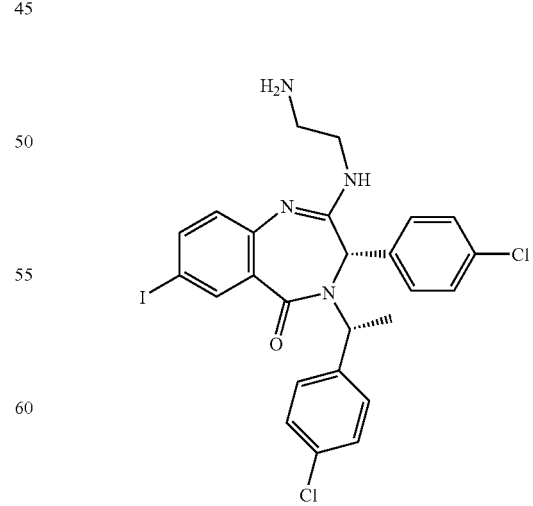

Mass spectrum (LCMS, ESI pos.): Calcd for C$_{25}$H$_{23}$Cl$_2$IN$_4$O: 592.03; found 593.0 (M+H).

Example 31

2-[N-(3-amino-3-oxopropyl)amino]-(3S)-3-(4-chlorophenyl)-4-[(R)-1-(4-chlorophenyl)ethyl]-7-iodo-3,4-dihydro-1,4-benzodiazepin-5-one

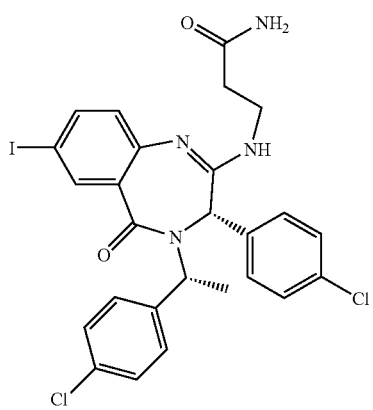

MASS SPECTRUM (LCMS, ESI POS.): CALCD FOR $C_{26}H_{23}CL_2IN_4O_2$: 620.02; FOUND 621.0 (M+H).

Example 32

5-[(3S)-3-(4-chlorophenyl)-4-[(R)-1-(4-chlorophenyl)ethyl]-7-methoxycarbonyl-2,5-dioxo-3,4-dihydro-1H-1,4-benzodiazepin-1-yl]valeric acid tert-butyl ester

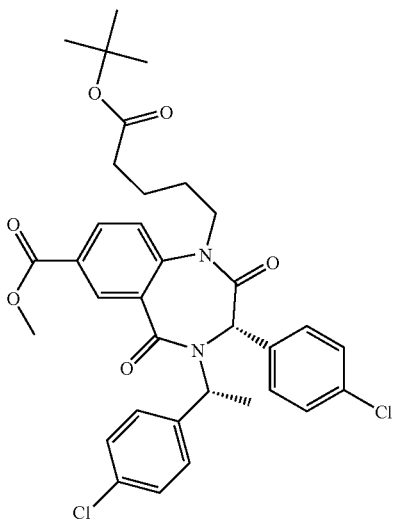

A solution of 5-[(3S)-3-(4-chlorophenyl)-4-[(R)-1-(4-chlorophenyl)ethyl]-7-iodo-2,5-dioxo-3,4-dihydro-1H-1,4-benzodiazepin-1-yl]valeric acid tert-butyl ester (300 mg, 0.42 mmol), dichloro bis-(triphenylphosphine)Pd(II) (21 mg, 0.030 mmol), and triethylamine (200 μL, 1.43 mmol), in DMF (4 mL) and methanol (1.5 mL) was stirred under a carbon monoxide atmosphere at 80° C. for 24 h. After the solution was cooled to room temperature, the solvent was evaporated under reduced pressure. The crude reaction product was purified by column chromatography on silica gel (EtOAc/hexanes, 1:2) to give the title compound (226 mg, 83%): $^1$H NMR (400 MHz, CDCl$_3$) δ 1.45 (s, 9H, 3 CH$_3$), 1.58–1.62 (m, 2H, CH$_2$), 1.75 (d, J=5.4 Hz, 3H, CH$_3$), 2.24 (t, J=10.5 Hz, 2H, CH$_2$), 3.62–3.90 (m, 3H, 3 CH), 3.91 (s, 3H, CH$_3$), 4.23–4.31 (m, 1H, CH), 5.34 (s, 1H, CH), 6.45 (q, J=5.4 Hz, 1H, CH), 6.50 (d, J=6.3 Hz, 2H, ArH), 6.84 (d, J=6.3 Hz, 2H, ArH), 6.94 (d, J=6.6 Hz, 1H, ArH), 7.32 (d, J=6.6 Hz, 2H, ArH), 7.50 (d, J=6.3 Hz, 2H, ArH), 7.84 (dd, J=6.3 Hz, J=1.5 Hz, 1H, ArH), 8.33 (d, J=1.5 Hz, 1H, ArH).

Example 33

(3S)-1-(4-tert-Butoxycarbonyl-butyl)-3-(4-chlorophenyl)-4-[(R)-1-(4-chloro-phenyl)-ethyl]-2,5-dioxo-2,3,4,5-tetrahydro-1H-benzo[e][1,4]diazepine-7-carboxylic acid

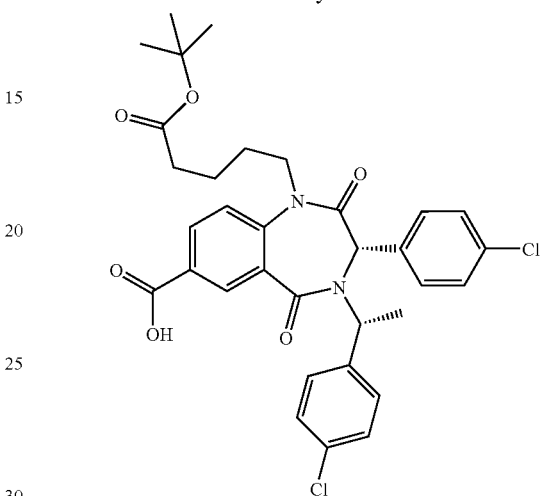

A solution of 5-[(3S)-3-(4-chlorophenyl)-4-[(R)-1-(4-chlorophenyl)ethyl]-7-methoxycarbonyl-2,5-dioxo-3,4-dihydro-1H-1,4-benzodiazepin-1-yl]valeric acid tert-butyl ester (Example 32) (200 mg, 0.31 mmol) and NaOH (1N in water, 380 μL) in THF/MeOH/H$_2$O (2 mL/400 μL/100 μL) was stirred at room temperature for 12 h. The mixture was evaporated to dryness. Then, the residue was dissolved in water (10 mL) and the pH was adjusted to 4 with 1N HCl. The solution was extracted with ether (3×20 mL), then the organic layer was dried (Na$_2$SO4) and concentrated to dryness under reduced pressure. Filtration over silica gel afforded the title compound (150 mg, 77%): Mass spectrum (LCMS, ESI pos.): Calcd for $C_{33}H_{34}Cl_2IN_2O_6$: 624.18; found 568.9 (M+H—t-bu).

Example 34

7-aminocarbonyl-5-[(3S)-3-(4-chlorophenyl)-4-[(R)-1-(4-chlorophenyl)ethyl]-2,5-dioxo-3,4-dihydro-1H-1,4-benzodiazepin-1-yl]valeric acid

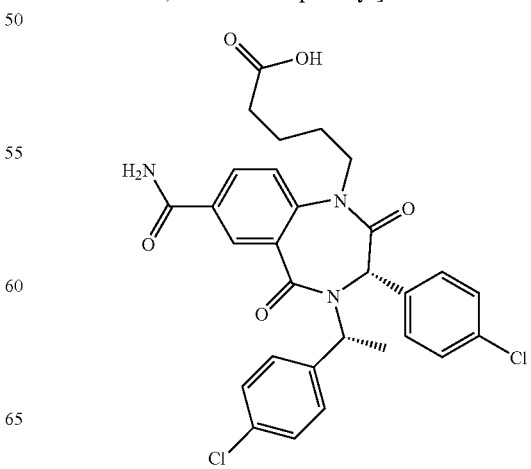

A solution of (3S)-1-(4-tert-Butoxycarbonyl-butyl)-3-(4-chloro-phenyl)-4-[(R)-1-(4-chloro-phenyl)-ethyl]-2,5-dioxo-2,3,4,5-tetrahydro-1H-benzo[e][1,4]-diazepine-7-carboxylic acid (Example 33) (63 mg, 0.10 mmol), O-(7-azabenzotriazol-1-yl)-N,N,N',N'-tetramethyluroniumhexafluorophosphate (57 mg, 0.15 mmol), HOBT (20 mg, 0.15 mmol) N,N-diisopropylethylamine (70 µL, 0.4 mmol), ammonium chloride (11 mg, 0.2 mmol) in DMF (400 µL) was stirred at room temperature for 1 h. under argon atmosphere. After evaporation of the solvent, the residue was diluted with EtOAc (15 mL), washed with water (10 mL), dried (Na2SO4) then concentrated to dryness under reduced pressure. Chromatography on silica (EtOAc/hexanes, 1:1) afforded anoil (58 mg), which was dissolved in dichloromethane (1.5 mL) and TFA (0.5 mL). This solution was stirred at room temperature for 10 h, then evaporated to dryness. The residue was dissolved in ice-cold water (10 mL) and AcONa (100 mg)/AcOH (100 µL) were added. The solution was extracted with ether (3×20 mL), then the organic layer was dried (Na$_2$SO$_4$) and concentrated to dryness under reduced pressure. Purification by column chromatography (EtOAc/CH$_2$Cl$_2$/EtOH, 5:4:1) afforded a colorless oil, which was converted to its sodium salt with NaOH 1N in EtOH. Recrystallization from EtOH/ether yielded title compound (37 mg, 62%) as a white powder: Mass spectrum (LCMS, ESI pos.): Calcd for C$_{29}$H$_{27}$Cl$_2$IN$_3$O$_5$: 567.13; found 568.0 (M+H).

Example 35

5-[4-(4-Chloro-2-methyl-benzyl)-3-(R,S)-(4-chloro-phenyl)-7-iodo-2,5-dioxo-2,3,4,5-tetrahydro-benzo[e][1,4]diazepin-1-yl]-valeric acid

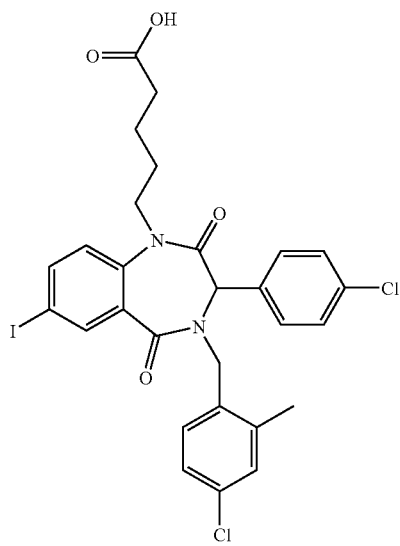

$^1$H NMR (400 MHz, DMSO-d$_6$) δ 7.71 (d, J=2.2 Hz, 1H), 7.64–7.68 (m, 1H), 7.32 (m, 1H), 7.16–7.24 (m, 4H), 7.00 (d, J=7.0 Hz, 1H), 6.88 (d, J=7.6 Hz, 2H), 5.25 (s, 1H), 5.31 (d, J=15.6 Hz, 1H), 4.68 (d, J=15.4 Hz, 1H), 4.20 (m, 2H), 3.70 (m, 2H), 2.32 (s, 4H), 2.16–2.20 (m, 4H). Mass spectrum (LCMS, ESI pos.): Calcd for C$_{28}$H$_{25}$Cl$_2$IN$_2$O$_4$: 650.02; found 650.8 (M+H).

Example 36

Sodium; 5-{(3R)-3-(4chloro-phenyl)-4-[(R)-1-(4chloro-phenyl)-ethyl]-7-iodo-2,5-dioxo-2,3,4,5-tetrahydro-benzo[e][1,4]diazepin-1-yl}-valerate

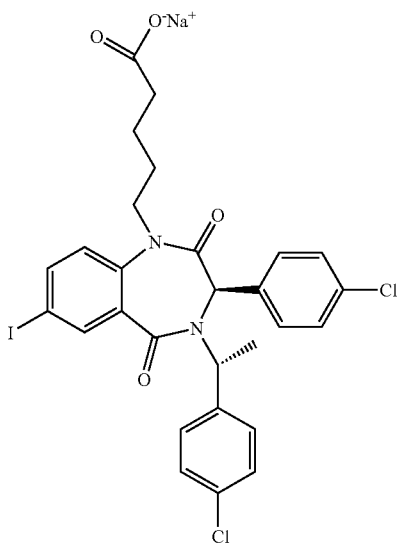

$^1$H NMR (400 MHz, DMSO-d$_6$) δ 7.88 (d, J=2.0 Hz, 1H), 7.56–7.60 (m, 1H), 7.40–7.44 (m, 4H), 7.10–7.14 (m, 2H), 6.90–6.95 (m, 2H), 6.80–6.84 (d, J=8.8 Hz, 1H), 6.36–6.40 (m, 1H), 5.32 (s, 1H), 4.04–4.10 (m, 1H), 3.52–3.60 (m, 1H), 2.03–2.12 (m, 1H), 1.64–1.68 (d, J=7.2 Hz, 4H), 1.40–1.52 (m, 4H). Mass spectrum (LCMS, ESI pos.): Calcd for C$_{28}$H$_{24}$Cl$_2$IN$_2$NaO$_4$: 672. 1; found 673.2 (M+H).

Example 37

5-[(3S)-3-(4-Chlorophenyl)-4-[(R)-1-(4chlorophenyl)-ethyl]-7-[(R,S)-1-hydroxyethyl]-2,5-dioxo-2,3,4,5-tetrahydro-benzo[e][1,4]diazepin-1-yl]-valeric acid

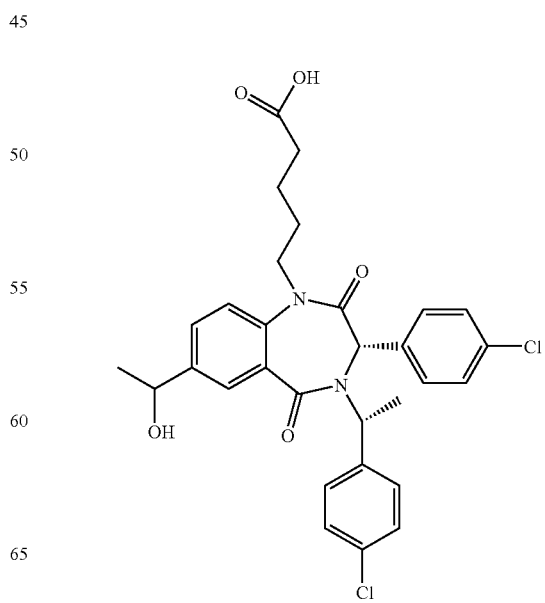

a) 5-[(3R,S)-3-(4-Chloro-phenyl)-4-[(R)-1-(4-chloro-phenyl)-ethyl]-7-[(R,S)-1-hydroxy-ethyl]-2,5-dioxo-2,3,4,5tetrahydro-benzo[e][1,4]diazepin-1-yl]-valeric acid tert-butyl ester A solution of 5-{(3R,S)-7-Acetyl-3-(4-chloro-phenyl)-4-[1-(R)-(4-chloro-phenyl)-ethyl]-2,5-dioxo-2,3,4,5-tetrahydro-benzo[e][1,4]diazepin-1-yl}-valeric acid tert-butyl ester (60 mg, 0.096 mmol) in MeOH (2 mL) was treated with NaBH$_4$ (5.0 mg, 0.13 mmol). The solution was stirred at RT for 18 h. All of the solution was applied to a prep tlc plate (Analtech Silica Gel GF, 20×20 cm, 2000 microns). The desired band was scraped off, extracted with MeOH for 10 min. filtered and concentrated to give the title compound (55 mg, 92%). Mass spectrum (LCMS, ESI pos.): Calcd for C$_{34}$H$_{38}$Cl$_2$N$_2$O$_5$: 624.22; found 625.4 (M+H).

b) 5-[(3S)-3-(4-Chloro-phenyl)-4-[1-(R)-(4-chloro-phenyl)-ethyl]-7-(1-(R,S)-hydroxy-ethyl)-2,5-dioxo-2,3,4,5-tetrahydro-benzo[e][1,4]diazepin-1-yl]-valeric acid The title compound was synthesized from 5-[(3R,S)-3-(4-Chloro-phenyl)-4-[(R)-1-(4-chloro-phenyl)-ethyl]-7-[(R,S)-1 hydroxy-ethyl]-2,5-dioxoo-2,3,4,5-tetrahydro-benzo[e][1,4]-diazepin-1-yl]-valeric acid tert-butyl ester following the procedure for example 1, step b. $^1$H NMR (400 MHz, DMSO-d$_6$) δ 7.56–7.61 (m, 3H), 7.40–7.50 (m, 1H), 7.18–7.38 (m, 3H), 7.00–7.08 (t, J=8.3 Hz, 1H), 6.83–6.87 (m, 2H), 6.50–6.56 (m, 2H), 6.35–6.40 (m, 1H), 5.35 (s, 1H), 4.68–4.72 (m, 1H), 4.30–4.40 (m, 1H), 3.70–3.79 (m, 1H), 2.10–2.18 (m, 2H), 1.72–1.76 (d, J=7.3 Hz, 4H), 1.50–1.70 (m, 4H), 1.21–1.26 (d, J=6.6 Hz, 3H). Mass spectrum (LCMS, ESI pos.): Calcd for C$_{30}$H$_{30}$Cl$_2$N$_2$O$_5$: 568.1; found 569.3 (M+H).

Example 38

5-[(R,S)-3-(4-Chloro-phenyl)-4-[(R)-1-(4-chloro-phenyl)-ethyl]-7-(1-(R,S)-hydroxyehtyl)-2,5-dioxo-2,3,4,5-tetrahydro-benzo[e][1,4]diazepin-1-yl]-valeric acid

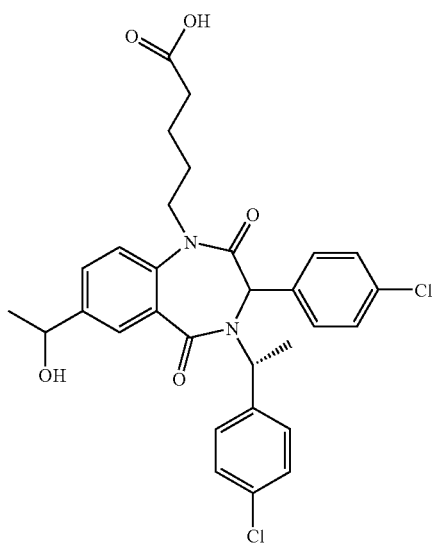

The title compound was prepared following successively the procedures described for example 37: $^1$H NMR (400 MHz, DMSO-d$_6$) δ 7.00–7.61 (m, 9H), 6.84–6.92 (m, 2H), 6.36–6.56 (m, 3H), 5.30–5.36 (m, 1H), 4.08–4.76 (m, 2H), 3.50–3.80 (m, 1H), 2.05–2.20 (m, 2H), 1.72–1.76 (d, J=7.3 Hz, 3H), 1.20–1.70 (m, 7H). Mass spectrum (LCMS, ESI pos.): Calcd for C$_{30}$H$_{30}$Cl$_2$N$_2$O$_5$: 568.1; found 569.2 (M+H).

Example 39

5-[(3S)-4-[(R)-1-(4-Chlorophenyl)ethyl]-7-iodo-2,5-dioxo-3-(4-trifluoromethyl-phenyl)-2,3,4,5-tetrahydro-benzo[e][1,4]diazepin-1-yl]-valeric acid

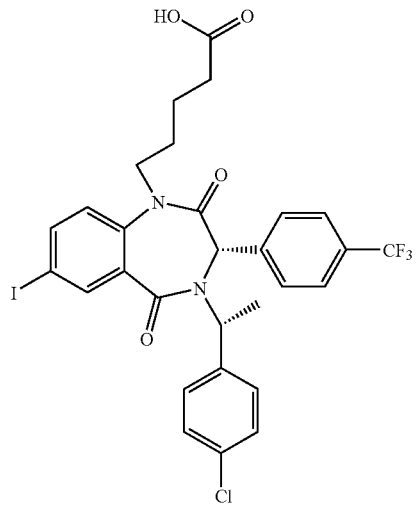

$^1$H NMR (400 MHz, DMSO-d$_6$) δ 7.86–7.91 (d, J=2.0 Hz, 1H), 7.52–7.58 (m, 1H), 7.45–7.51 (m, 4H), 7.12–7.22 (m, 2H), 6.92–7.05 (m, 2H), 6.82–6.94 (d, J=8.8 Hz, 1H), 6.32–6.38 (m, 1H), 5.32 (s, 1H), 4.08–4.11 (m, 1H), 3.52–3.64 (m, 1H), 2.06–2.11 (m, 2H), 1.62–1.70 (d, J=7.2 Hz, 4H), 1.40–1.46 (m, 4H). Mass spectrum (LCMS, ESI pos.): Calcd for C$_{29}$H$_{25}$ClF$_3$IN$_2$O$_4$: 684.05; found 685.1 (M+H).

Example 40

Sodium; 5-{(S)-3-(4-chloro-phenyl)-4-[(R)-1-(4-chloro-phenyl)-ethyl]-7-ethynyl-2,5-dioxo-2,3,4,5-tetrahydro-benzo[e][1,4]diazepin-1-yl}-valerate

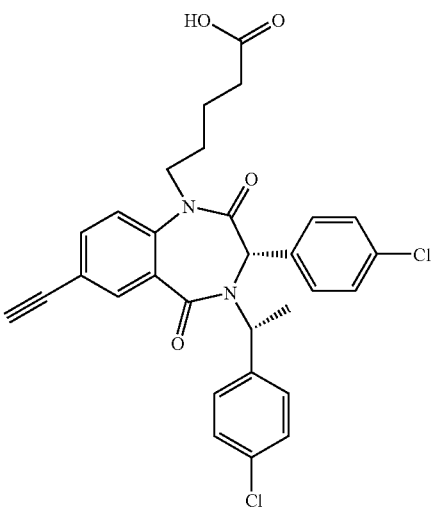

a) 5-{(3R,S)-3-(4-Chlorophenyl)-4-[(R)-1-(4-chlorophenyl)ethyl]-7-ethynyl-2,5-dioxo-2,3,4,5-tetrahydro-benzo[e][1,4]diazepin-1-yl}-valeric acid tert-butyl ester A mixture of 5-{(3R,S)-3-(4-Chloro-phenyl)-4-[(R)-1-(4-chloro-phenyl)-ethyl]-7-iodo-2,5-dioxo-2,3,4,5tetrahydro-benzo[e][1,4]diazepin-1-yl}-valeric acid tert-butyl ester (3.2 g, 4.5 mmol), trimethylsilylacetylide (1.9 mL, 13.5 mmol), CuI (189 mg, 0.99 mmol) and dichlorobis(triphenylphosphine) palladium (II) (318 mg, 0.45 mmol) in triethylamine (200 mL) was heated to 55° C. under an argon atmosphere. After 1 h solution was filtered hot and filtrate was concentrated. A solution of 5-{(3R,S)-3-(4-Chlorophenyl)-4-[(R)-1-(4-chlorophenyl)ethyl]-2,5-dioxo-7-trimethylsilanylethynyl-2,3,4,5-tetrahydro-benzo[e][1,4]diazepin-1-yl}-valeric acid tert-butyl ester (6.7 g, 9.9 mmol) in THF (100 mL) was treated with tetrabutylammonium fluoride (10 mL of 1 M in THF, 10 mmol). After 1 h reaction solution was concentrated. Flash chromatography (silica gel, EtOAc/hexanes 3:7) gave the title compound (5.3g, 89% over two steps).

Sodium; 5-{(3S)-3-(4-chloro-phenyl)-4-[(R)-1-(4-chloro-phenyl)-ethyl]-7-ethynyl-2,5-dioxo-2,3,4,5-tetrahydro-benzo[e][1,4]diazepin-1-yl}-valerate

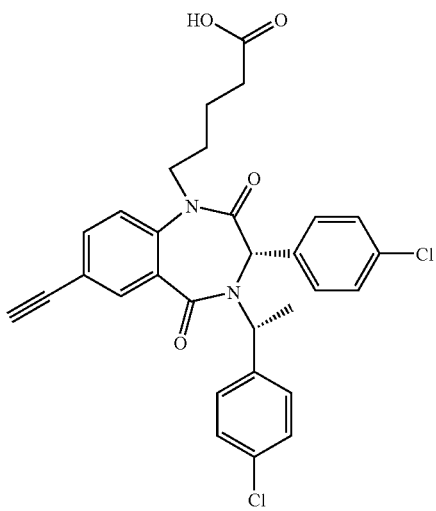

The title compound was synthesized from 5-{(3R,S)-3-(4-Chlorophenyl)-4-[(R)-1-(4-chloro-phenyl-ethyl]-7-ethynyl-2,5-dioxo-2,5-tertahydro-benzo[e][1,4]diazepin-1-yl}-valeric acid tert-butyl ester following the example 1, step b.
$^1$H NMR (400 MHz, DMSO-d$_6$) δ 7.59–7.64 (m, 3H), 7.30–7.40 (m, 3H), 7.08–7.10 (d, J=8.5 Hz, 1H), 6.90–6.93 (d, J=8.5, 2H), 6.53–6.58 (d, J×8.8, 2H), 6.32–6.39 (m, 1H), 5.36 (s, 1H), 4.24–4.32 (m, 1H), 3.76–3.84 (m, 1H), 3.52 (s, 1H), 2.12–2.20 (m, 2H), 1.72–1.76 (d, J=7.1 Hz, 3H), 1.52–1.64 (m, 4H). Mass spectrum (LCMS, ESI pos.): Calcd for $C_{30}H_{25}Cl_2N_2NaO_4$: 570.11; found 571.2 (M+H).

Example 41

5-{(3R,S)-3-(4-Chlorophenyl)-4-[(R,S)-1-(4-chlorophenyl)-2-hydroxyethyl]-7-iodo-2,5-dioxo-2,3,4,5-tetrahydro-benzo[e][1,4]diazepin-1-yl}-valeric acid

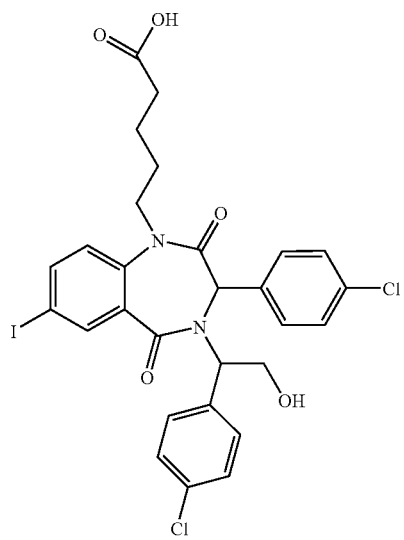

$^1$H NMR (400 MHz, DMSO-d$_6$) δ 7.84–7.87 (d, J=2.1 Hz, 1H), 7.55–7.60 (m, 3H), 7.36–7.40 (m, 2H), 6.88–6.96 (m, 3H), 6.56–6.60 (d, J=7.7, 2H), 6.20–6.28 (m, 1H), 5.40 (s, 1H), 4.12–4.33 (m, 3H), 3.70–3.80 (s, 1H), 2.12–2.20 (m, 2H), 1.50–1.76 (m, 6H). Mass spectrum (LCMS, ESI pos.): Calcd for $C_{28}H_{25}Cl_2IN_2O_5$: 666.02; found 667.2 (M+H).

Example 42

Sodium; 5-{(3S)-3-(4-chlorophenyl)-4-[(R)-1-(4-chlorophenyl)ethyl]-7-iodo-2,5-dioxo-2,3,4,5-tetrahydro-benzo[e][1,4]diazepin-1-yl}-valerate

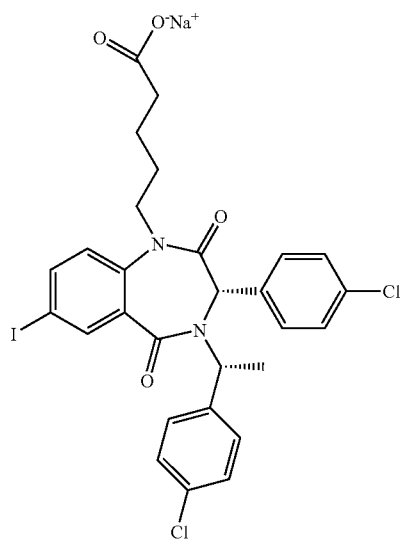

$^1$H NMR (400 MHz, DMSO-d$_6$) δ 7.75–7.77 (d, J=2.1 Hz, 1H), 7.56–7.64 (m, 3H), 7.39–7.44 (m, 2H), 6.98–7.03 (m, 2H), 6.90–6.95 (m, 1H), 6.56–6.60 (d, J=7.7 Hz, 1H), 6.16–6.22 (m, 1H), 5.26 (s, 1H), 4.15–4.24 (m, 1H), 3.60–3.70 (m, 1H), 1.76–1.84 (m, 2H), 1.60–1.68 (d, J=7.1 Hz, 3H), 1.44–1.56 (m, 1H), 1.28–1.37 (m, 4H). Mass spectrum (LCMS, ESI pos.): Calcd for C$_{28}$H$_{24}$Cl$_2$IN$_2$NaO$_4$: 672.01; found 651.2 (M–Na)$^+$.

Example 43

5-[(3R,S)-4-(4-Chloro-2-methyl-benzyl)-3-(4-chloro-phenyl)-7-iodo-2,5-dioxo-2,3,4,5-tetrahydro-benzo[e][1,4]diazepin-1-yl]-valeric acid

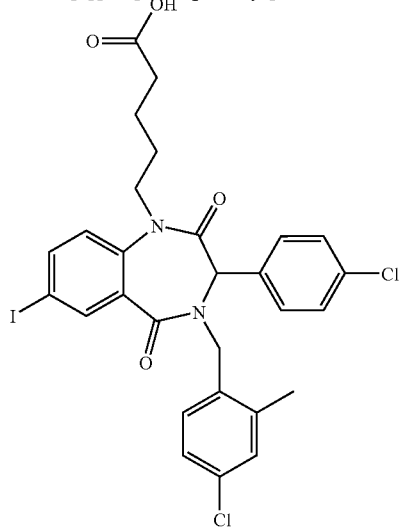

$^1$H NMR (400 MHz, DMSO-d$_6$) δ 7.71 (d, J=2.2 Hz, 1H), 7.64–7.68 (m, 1H), 7.32 (m, 1H), 7.16–7.24 (m, 4H), 7.00 (d, J=7.0 Hz, 1H), 6.88 (d, J=7.6 Hz, 2H), 5.25 (s, 1H), 5.31 (d, J=15.6 Hz, 1H), 4.68 (d, J=15.4 Hz, 1H), 4.20 (m, 2H), 3.70 (m, 2H), 2.32 (s, 4H), 2.16–2.20 (m, 4H). Mass spectrum (LCMS, ESI pos.): Calcd for C$_{28}$H$_{25}$Cl$_2$IN$_2$O$_4$: 650.02; found 650.8 (M+H).

Example 44

Sodium; 5-{(3R)-3-(4-chlorophenyl)-4-[(R)-1-(4-chlorophenyl)ethyl]-7-iodo-2,5-dioxo-2,3,4,5-tetrahydro-benzo[e][1,4]diazepin-1-yl}-valerate

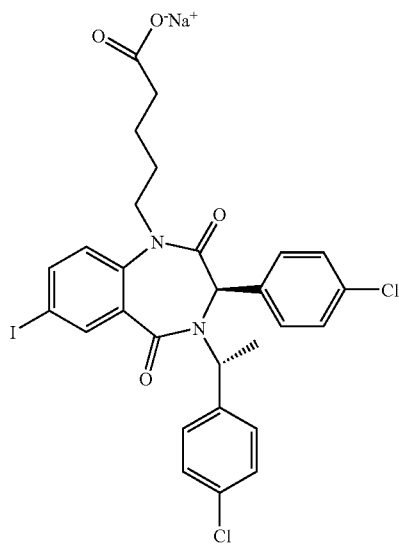

$^1$H NMR (400 MHz, DMSO-d$_6$) δ 7.88 (d, J=2.0 Hz, 1H), 7.56–7.60 (m, 1H), 7.40–7.44 (m, 4H), 7.10–7.14 (m, 2H), 6.90–6.95 (m, 2H), 6.80–6.84 (d, J=8.8 Hz, 1H), 6.36–6.40 (m, 1H), 5.32 (s, 1H), 4.04–4.10 (m, 1H), 3.52–3.60 (m, 1H), 2.03–2.12 (m, 1H), 1.64–1.68 (d, J=7.2 Hz, 4H), 1.40–1.52 (m, 4H). Mass spectrum (LCMS, ESI pos.): Calcd for C$_{28}$H$_{24}$Cl$_2$IN$_2$NaO$_4$: 672. 1; found 673.2 (M+H).

Example 45

5-[(3S)-3-(4-Chlorophenyl)-4-[(R)-1-(4-chlorophenyl)-ethyl]-7-(1-(R,S)-hydroxyethyl)-2,5-dioxo-2,3,4,5-tetrahydro-benzo[e][1,4]diazepin-1-yl]-valeric acid

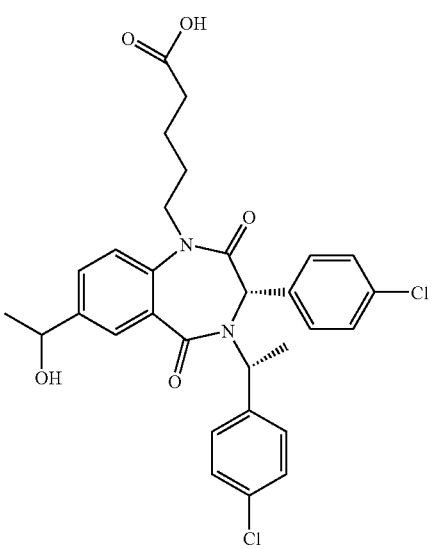

$^1$H NMR (400 MHz, DMSO-d$_6$) δ 7.56–7.61 (m, 3H), 7.40–7.50 (m, 1H), 7.18–7.38 (m, 3H), 7.00–7.08 (t, J=8.3 Hz, 1H), 6.83–6.87 (m, 2H), 6.50–6.56 (m, 2H), 6.35–6.40 (m, 1H), 5.35 (s, 1H), 4.68–4.72 (m, 1H), 4.30–4.40 (m, 1H), 3.70–3.79 (m, 1H), 2.10–2.18 (m, 2H), 1.72–1.76 (d, J=7.3 Hz, 4H), 1.50–1.70 (m, 4H), 1.21–1.26 (d, J=6.6 Hz, 3H). Mass spectrum (LCMS, ESI pos.): Calcd for C$_{30}$H$_{30}$Cl$_2$N$_2$O$_5$: 568.1; found 569.3 (M+H).

Example 46

5-[(3R,S)-3-(4-Chlorophenyl)-4-[(R)-1-(4-chlorophenyl)ethyl]-7-[(R,S)-1-hydroxy-ethyl]-2,5-dioxo-2,3,4,5-tetrahydro-benzo[e][1,4]diazepin-1-yl]-valeric acid

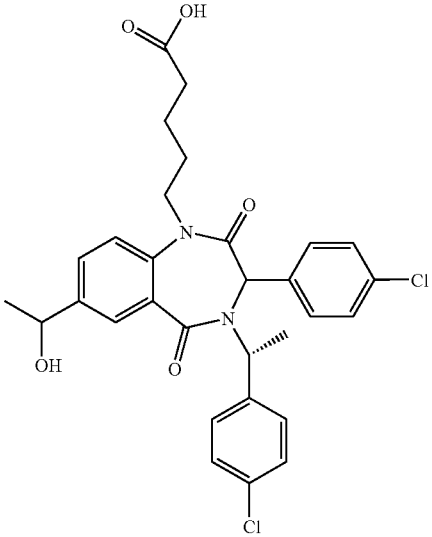

¹H NMR (400 MHz, DMSO-d₆) δ 7.00–7.61 (m, 9H), 6.84–6.92 (m, 2H), 6.36–6.56 (m, 3H), 5.30–5.36 (m, 1H), 4.08–4.76 (m, 2H), 3.50–3.80 (m, 1H), 2.05–2.20 (m, 2H), 1.72–1.76 (d, J=7.3 Hz, 3H), 1.20–1.70 (m, 7H). Mass spectrum (LCMS, ESI pos.): Calcd for $C_{30}H_{30}Cl_2N_2O_5$: 568.1; found 569.2 (M+H).

Example 47

5-[(3S)-4-[(R)-1-(4-Chlorophenyl)-ethyl]-7-iodo-2,5-dioxo-3-(4-triflurormethyl-phenyl)-2,3,4,5-tetrahydro-benzo[e][1,4]diazepin-1-yl]-valeric acid

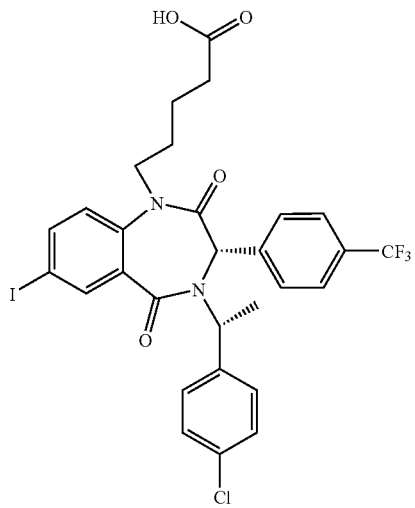

¹H NMR (400 MHz, DMSO-d₆) δ 7.86–7.91 (d, J=2.0 Hz, 1H), 7.52–7.58 (m, 1H), 7.45–7.51 (m, 4H), 7.12–7.22 (m, 2H), 6.92–7.05 (m, 2H), 6.82–6.94 (d, J=8.8 Hz, 1H), 6.32–6.38 (m, 1H), 5.32 (s, 1H), 4.08–4.11 (m, 1H), 3.52–3.64 (m, 1H), 2.06–2.11 (m, 2H), 1.62–1.70 (d, J=7.2 Hz, 4H), 1.40–1.46 (m, 4H). Mass spectrum (LCMS, ESI pos.): Calcd for $C_{29}H_{25}ClF_3IN_2O_4$: 684.05; found 685.1 (M+H).

Example 48

Sodium; 5-{(3S)-3-(4-chlorophenyl)-4-[(R)-1-4-chlorophenyl)-ethyl]-7-ethynyl-2,5-dioxo-2,3,4,5-tetrahydro-benzo[e][1,4]diazepin-1-yl}-valerate

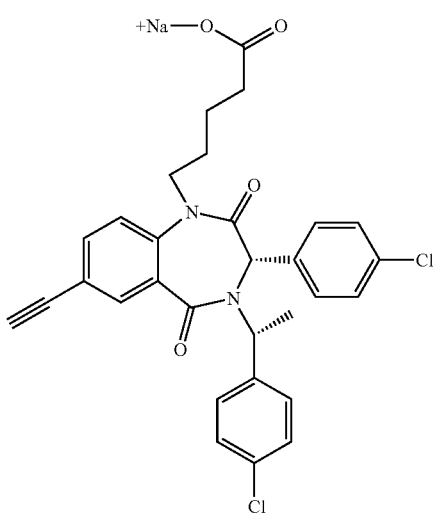

¹H NMR (400 MHz, DMSO-d₆) δ 7.59–7.64 (m, 3H), 7.30–7.40 (m, 3H), 7.09 (d, J=8.5 Hz, 1H), 6.92 (d, J=8.5, 2H), 6.54 (d, J=8.8, 2H), 6.32–6.39 (m, 1H), 5.36 (s, 1H), 4.24–4.32 (m, 1H), 3.76–3.84 (m, 1H), 3.52 (s, 1H), 2.12–2.20 (m, 2H), 1.73 (d, J=7.1 Hz, 3H), 1.52–1.64 (m, 4H). Mass spectrum (LCMS, ESI pos.): Calcd for $C_{30}H_{25}Cl_2N_2NaO_4$: 570.1; found 571.2 (M+H).

Example 49

5-{3-(4-Chlorophenyl)-4-[1-(4-chlorophenyl)-2-hydroxy-ethyl]-7-iodo-2,5-dioxo-2,3,4,5-tetrahydro-benzo[e][1,4]diazepin-1-yl}-valeric acid

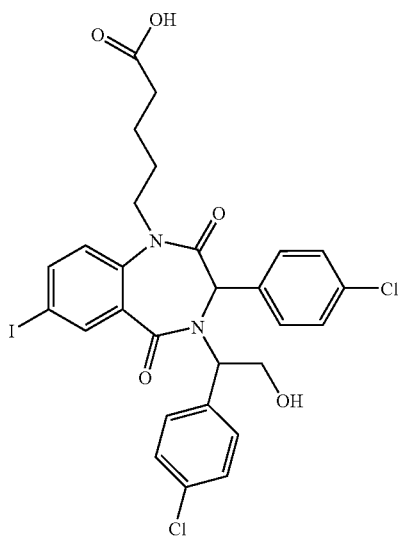

¹H NMR (400 MHz, DMSO-d₆) δ 7.85 (d, J=2.1 Hz, 1H), 7.55–7.60 (m, 3H), 7.36–7.40 (m, 2H), 6.88–6.96 (m, 3H), 6.58 (d, J=7.7, 2H), 6.20–6.28 (m, 1H), 5.40 (s, 1H), 4.12–4.33 (m, 3H), 3.70–3.80 (s, 1H), 2.12–2.20 (m, 2H), 1.50–1.76 (m, 6H). Mass spectrum (LCMS, ESI pos.): Calcd for $C_{28}H_{25}Cl_2IN_2O_5$: 666.02; found 667.2 (M+H).

Example 50

Sodium; 5-{(3S)-3-(4-chlorophenyl)-4-[(R)-1-(4-chlorophenyl)-ethyl]-7-iodo-2,5-dioxo-2,3,4,5-tetrahydro-benzo[e][1,4]diazepin-1-yl}-valerate

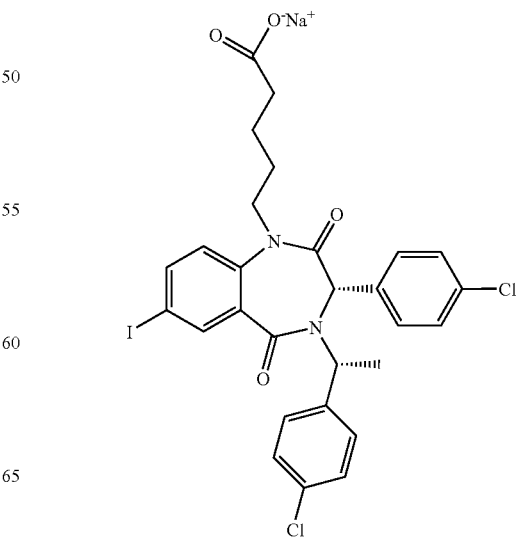

$^1$H NMR (400 MHz, DMSO-d$_6$) δ 7.76 (d, J=2.1 Hz, 1H), 7.56–7.64 (m, 3H), 7.39–7.44 (m, 2H), 6.98–7.03 (m, 2H), 6.90–6.95 (m, 1H), 6.57 (d, J=7.7 Hz, 1H), 6.16–6.22 (m, 1H), 5.26 (s, 1H), 4.15–4.24 (m, 1H), 3.60–3.70 (m, 1H), 1.76–1.84 (m, 2H), 1.64 (d, J=7.1 Hz, 3H), 1.44–1.56 (m, 1H), 1.28–1.37 (m, 4H). Mass spectrum (LCMS, ESI pos.): Calcd for C$_{28}$H$_{24}$Cl$_2$IN$_2$NaO$_4$: 672.01; found 651.2 (M–Na)$^+$.

Example 51

5-[(3S)-3-(4-Chlorophenyl)-4-[(R)-1-(4-chlorophenyl)ethyl]-7-(methylthio)-2,5-dioxo-1,4-benzodiazepin-1-yl]valeric acid

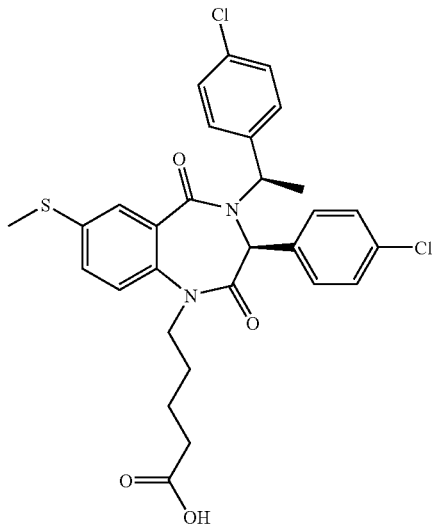

a) (3S)-3-(4-Chlorophenyl)-4-[(R)-1-(4-chlorophenyl)ethyl]-7-(methylthio)-1,3-dihydro-1,4-benzodiazepine-2,5-dione.

(3S)-3-(4-Chlorophenyl)-4-[(R)-1-(4-chlorophenyl)ethyl]-7-iodo-1,3-dihydro-1,4-benzodiazepine-2,5-dione (221 mg, 0.400 mmol), sodium thiomethoxide (38 mg, 0.521 mmol) and tetrakis(triphenylphosphine)palladium (0) (46 mg, 0.04 mmol) were suspended in n-butanol (5mL) under nitrogen atmosphere. The reaction was warmed up to 110° C. for 16 h. Then, the reaction was allowed to cool down to room temperature, partitioned between ethyl acetate and sodium hydroxide (1N), and washed with hydrochloric acid (1N). The organic layer was collected, dried with sodium sulfate, filtered and concentrated under vacuum. The residue was purified by column chromatography (AcOEt/Hexanes, 1:1) to give the title compound (91 mg, 48%) identified as the "lower diastereomer" (in a TLC performed with AcOEt/Hexanes, 1:1): $^1$H NMR (400 MHz, CDCl$_3$) δ 9.16 (s, 1H), 7.50 (d, J=2.3 Hz, 1H), 7.45 (d, J=8.5 Hz, 2H), 7.24 (d, J=8.5 Hz, 2H), 7.00 (dd, J=2.3, J=8.5 Hz, 1H), 6.83 (d, J=8.5 Hz, 2H), 6.61 (d, J=8.5 Hz, 1H), 6.56 (d, J=8.5 Hz, 2H), 6.39 (m, 1H), 5.16 (s, 1H), 2.33 (s, 3H), 1.64 (d, J=7.19 Hz, 3H); together with (3R)-3-(4-chlorophenyl)-4-[(R)-1-(4-chlorophenyl)ethyl]-7 (methylthio)-1,3-dihydro-1,4-benzodiazepine-2,5-dione (45 mg, 24%) identified as the "upper diastereomer" (in a TLC performed with AcOEt/Hexanes, 1:1): $^1$H NMR (400 MHz, CDCl$_3$) δ 8.73 (s, 1H), 7.60 (d, J=2.3 Hz, 1H), 7.24 (d, J=8.5 Hz, 2H), 7.15 (d, J=8.5 Hz, 2H), 7.04 (m, 3H), 6.93 (d, J=8.5 Hz, 2H), 6.45 (d, J=8.5 Hz, 1H), 6.38 (m, 1H), 5.01 (s, 1H), 2.36 (s, 3H), 1.59 (d, J=7.2 Hz, 3H).

b) 5-[(3S)-3-(4-Chlorophenyl)-4-[(R)-1-(4-chlorophenyl)ethyl]-7-(methylthio)-2,5-dioxo-1,4-benzodiazepin-1-yl]valeric acid The title compound was prepared from (3S)-3-(4-Chlorophenyl)-4-[(R)-1-(4-chlorophenyl)ethyl]-7 (methylthio)-1,3-dihydro-1,4-benzodiazepine-2,5-dione following the procedure described for example 1, step b: $^1$H NMR (400 MHz, Cl$_3$CD) δ 10.89 (s, 1H, Acid-OH), 7.38 (d, J=8.5 Hz, 2H), 7.33 (d, J=2.3 Hz, 1H), 7.20 (d, J=8.5 Hz, 2H), 6.97 (dd, J=2.3, J=8.5 Hz, 1H), 6.75 (d, J=8.5 Hz, 2H), 6.67 (d, J=8.5 Hz, 1H), 6.36 (d, J=8.5 Hz, 2H), 6.29 (m, 1H), 5.26 (s, 1H), 4.28 (m, 1H), 3.54 (m, 1H), 2.35 (s, 3H), 2.34 (m, 2H), 1.63 (d, J=7.19 Hz, 3H), 1.46 (m, 4H). Mass spectrum (LCMS, ESI pos.): Calcd for C$_{29}$H$_{28}$Cl$_2$N$_2$O$_4$S: 570.1; found 571.0 (M+H).

Example 52

5-[(3R)-3-(4-Chlorophenyl)-4-[(R)-1-(4-chlorophenyl)ethyl]-7-(methylthio)-2,5-dioxo-1,4-benzodiazepin-1-yl]valeric acid

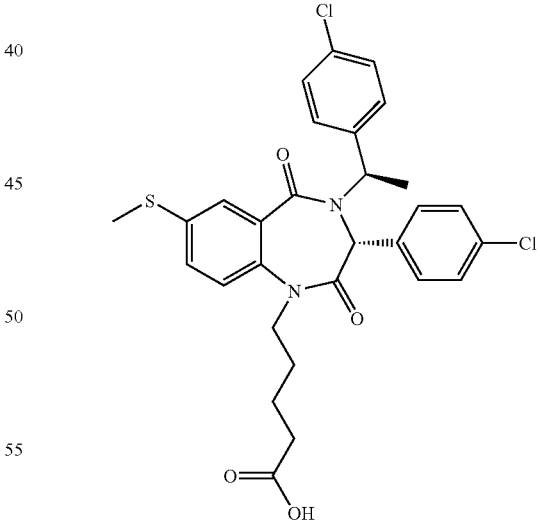

$^1$H NMR (400 MHz, CDCl$_3$) δ 7.42 (d, J=2.3 Hz, 1H), 7.27 (m, 4H), 6.98 (m, 3H), 6.75 (d, J=8.5 Hz, 2H), 6.62 (d, J=8.5 Hz, 1H), 6.37 (m, 1H), 5.22 (s, 1H), 4.05 (m, 1H), 3.37 (m, 1H), 2.35 (s, 3H), 2.19 (m, 2H), 1.58 (d, J=7.2 Hz, 3H), 1.38 (m, 4H). Mass spectrum (LCMS, ESI pos.): Calcd for C$_{29}$H$_{28}$Cl$_2$N$_2$O$_4$S: 570.1; found 571.0 (M+H).

Example 53

5-[(3S)-3-(4-Chlorophenyl)-4-[(R)-1-(4-chlorophenyl)ethyl]-7-(trifluoromethylthio)-2,5-dioxo-1,4-benzodiazepin-1-yl]valeric acid

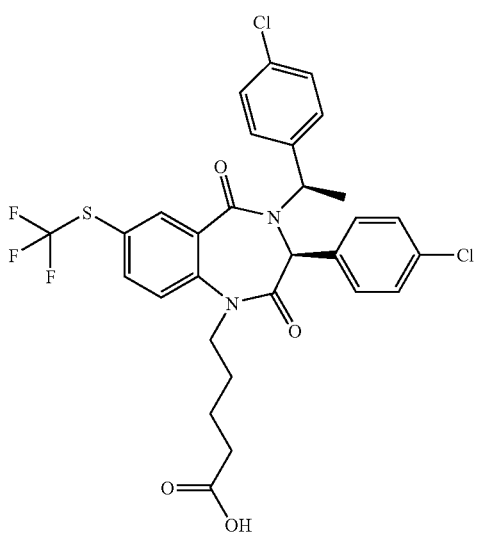

a) (3S)-3-(4-Chlorophenyl)-4-[(R)-1-(4-chlorophenyl)ethyl]-7-(trifluoromethylthio)-1,3-dihydro-1,4-benzodiazepine-2,5-dione (3S)-3-(4-Chlorophenyl)-4-[(R)-1-(4-chlorophenyl)ethyl]-7-iodo-1,3-dihydro-1,4-benzodiazepine-2,5-dione (248 mg, 0.449 mmol), copper trifluoromethanethiol (79.5 mg, 0.483 mmol), copper iodide (4 mg, 0.021 mmol), ethylene glycol (54.5 mg, 0.878 mmol) and potassium carbonate (121 mg, 0.878 mmol), were suspended in isopropanol (5 mL) under nitrogen atmosphere. The reaction was warmed up to 110° C. for 24 h. Then, the reaction was allowed to cool to room temperature and was partitioned between ethyl acetate and sodium hydroxide (1N), washed with hydrochloric acid (1N). The organic layer was collected, dried (Na2SO$_4$), filtered and concentrated under vacuum. Purification by chromatography on silica (AcOEt/Hexanes, 3:7) afforded the title compound (203 mg, 86%) identified as the "lower diastereomer" (in a TLC performed with AcOEt/Hexanes, 1:1): $^1$H NMR (400 MHz, CDCl$_3$) δ 9.31 (s, 1H), 7.98 (d, J=1.0 Hz, 1H), 7.44 (d, J=8.5 Hz, 2H), 7.40 (dd, J=1.0, J=8.5 Hz, 1H), 7.25 (d, J=8.5 Hz, 2H), 6.87 (d, J=8.5 Hz, 2H), 6.55 (d, J=8.5 Hz, 2H), 6.47 (d, J=8.5 Hz, 1H), 6.38 (m, 1H), 5.22 (s, 1H), 1.64 (d, J=7.2 Hz, 3H); together with (3R)-3-(4-chlorophenyl)-4-[(R)-1-(4-chlorophenyl)ethyl]-7-(trifluoromethylthio)-1,3-dihydro-1,4-benzodiazepine-2,5-dione (24 mg, 10%) identified as the "upper diastereomer" (in a TLC performed with AcOEt/Hexanes, 1:1): $^1$H NMR (400 MHz, CDCl$_3$) δ 8.28 (s, 1H), 8.07 (d, J=2.0 Hz, 1H), 7.44 (dd, J=2.0, J=8.5 Hz, 1H), 7.24 (d, J=8.5 Hz, 2H), 7.19 (d, J=8.5 Hz, 2H), 7.07 (d, J=8.5 Hz, 2H), 6.92 (d, J=8.5 Hz, 2H), 6.36 (m, 1H), 6.27 (d, J=8.5 Hz, 1H), 5.01 (s, 1H), 1.58 (d, J=7.2 Hz, 3H).

b) 5-[(3S)-3-(4-Chlorophenyl)-4-[(R)-1-(4-chlorophenyl)ethyl]-7-(trifluoromethylthio)-2,5-dioxo-1,4-benzodiazepin-1-yl]valeric acid.

The title compound was prepared from (3S)-3-(4-chlorophenyl)-4-[(R)-1-(4-chlorophenyl)ethyl]-7-(trifluoromethylthio)-1,3-dihydro-1,4-benzodiazepine-2,5-dione following the general procedure for the alkylation at the 1-position, followed by deprotection following the procedure for example 1 , step b: $^1$H NMR (400 MHz, Cl$_3$CD) δ 10.93 (s, 1H, Acid-OH), 7.83 (s, 1H), 7.38 (m, 3H), 7.20 (d, J=7.9 Hz, 2H), 6.77 (d, J=8.0 Hz, 2H), 6.51 (d, J=8.5 Hz, 1H), 6.35 (d, J=7.9 Hz, 2H), 6.28 (m, 1H), 5.28 (s, 1H), 4.25 (m, 1H), 3.55 (m, 1H), 2.27 (br s, 2H), 1.62 (d, J=6.8 Hz, 3H), 1.49 (m, 4H).

Example 54

5-[(3S)-3-(2-Allyloxy-4-chlorophenyl)-4-[(R)-1-(4-chlorophenyl)ethyl]-7-iodo-2,5-dioxo-1,4-benzodiazepin-1-yl]valeric acid

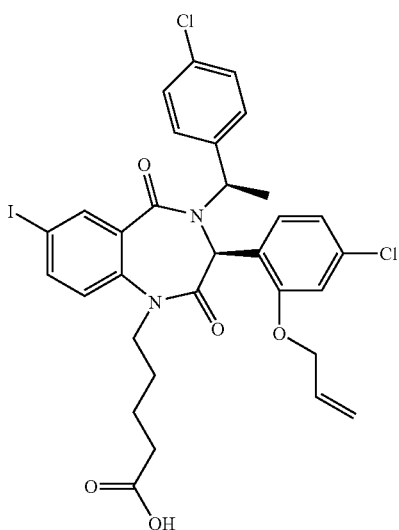

a) 5-Chloro-2-hydroxymethylphenol

4-Chlorosalicilic acid (25 g, 145 mmol) was dissolved in tetrahydrofuran (100 mL) and cooled down to 0° C. under argon atmosphere using an ice-water bath. Carefully, borane methyl sulfide complex (101 mL, 2M in THF) was added drop wise over a period of 30 minutes, and the resulting solution was refluxed for 16 h. The reaction was allowed to reach room temperature and poured into ice water, extracted with ethyl acetate, and washed with hydrochloric acid (1N). The organic layer was collected, dried with sodium sulfate, filtered and concentrated under vacuum. The residue was purified by chromatography on silica to give the title compound (83%): $^1$H NMR (400 MHz, CDCl$_3$) δ 7.66 (br s, 1H), 6.96 (d, J=8.0 Hz, 1H), 6.91 (d, J=0.95 Hz, 1H), 6.85 (dd, J=0.95, 8.0 Hz, 1H), 8.86 (s, 2H).

b) 4-Chloro-2-hydroxybenzaldehyde 2,3-Dichloro-5,6-dicyano-1-4-benzoquinone (DDQ, 9.92 g, 43.7 mmol) was added to a solution of 5-chloro-2-hydroxymethylphenol in dichloromethane (65 mL) and tetrahydrofuran (15 mL). The reaction mixture was stirred at room temperature for 4 h. Then, the solvent was evaporated under vacuum and the crude was purified by chromatography on silica to afford the title compound (72%):
$^1$H NMR (400 MHz, CDCl$_3$) δ 11.17 (s, 1H), 9.86 (s, 1H), 7.49 (d, J=7.3 Hz, 1H), 7.00 (m, 2H).

c) 2-Allyloxy-4-chlorobenzaldehyde

A mixture of 4-chloro-2-hydroxybenzaldehyde (254 mg, 1.62 mmol) and cesium carbonate (793 mg, 2.43 mmol) in THF (3 mL) was heated to reflux for 3 h. After the reaction mixture was cooled at room temperature, the solvent was evaporated and the residue partitioned between ethyl acetate and hydrochloric acid (1N). The organic layer was collected, dried with sodium sulfate, filtered and concentrated under vacuum. The residue was purified by column chromatography (AcOEt/Hexanes, 1:9) to give the title product (97%): $^1$H NMR (400 MHz, Cl$_3$CD) δ 10.46 (s, 1H), 7.80 (d, J=8.3 Hz, 1H), 7.05 (dd, J=0.78, 8.3 Hz, 1H), 6.99 (d, J=0.78 Hz, 1H), 6.09 (m, 1H), 5.45 (m, 2H), 4.67 (m, 2H).

d) (3S)-3-(2-Allyloxy-4-chlorophenyl)-4-[(R)-1-(4-chlorophenyl)ethyl]-7-iodo-1,3-dihydro-1,4-benzodiazepine-2,5-dione The title compound was prepared following the general procedure for the synthesis of diazepines and was identified as the "lower diastereomer" (in a TLC performed with AcOEt/Hexanes, 1:1): $^1$H NMR (400 MHz, CDCl$_3$) δ $^1$H NMR 9.49 (s, 1H), 7.99 (d, J=1.9 Hz, 1H), 7.38 (m, 3H), 7.15 (d, J=8.4 Hz, 2H), 6.40 (m, 3H), 6.32 (m, 1H), 6.24 (d, J=7.8 Hz, 1H), 5.87 (m, 1H), 5.29 (m, 3H), 4.31 (m, 1H), 1.62 (d, J=7.2 Hz, 3H). In this reaction (3R)-3-(2-allyloxy-4-chlorophenyl)-4-[(R)-1-(4-chlorophenyl)ethyl]-7-iodo-1,3-dihydro-1,4-benzodiazepine-2,5-dione was obtained and identified as the "upper diastereomer" (in a TLC performed with AcOEt/Hexanes, 1:1): $^1$H NMR (400 MHz, CDCl$_3$) δ 9.22 (s, 1H), 8.06 (d, J=1.6 Hz, 1H), 7.45 (dd, J=1.6, 8.3 Hz, 1H), 7.22 (d, J=8.3 Hz, 2H), 7.08 (d, J=8.4 Hz, 2H), 6.76 (d, J=8.4 Hz, 1H), 6.65 (dd, J=1.3, J=8.4 Hz, 1H), 6.59 (d, J=1.3 Hz, 1H), 6.28 (m, 2H), 5.83 (m, 1H), 5.24 (m, 1H), 5.05 (s, 1H), 4.35 (m, 2H), 1.50 (d, J=7.1 Hz, 3H).

e) 5-[(3S)-3-(2-Allyloxy-4-chlorophenyl)-4-[(R)-1-(4-chlorophenyl)ethyl]-7-iodo-2,5-dioxo-1,4-benzodiazepin-1-yl] valeric acid The title compound was prepared from (3S)-3-(2-allyloxy-4-chlorophenyl)-4-[(R)-1-(4-chlorophenyl)ethyl]-7-iodo-1,3-dihydro-1,4-benzodiazepine-2,5-dione following the general procedure for the alkylation at the 1-position, followed by deprotection following the procedures described for example 1, step b: $^1$H NMR (400 MHz, CDCl$_3$) δ 8.63 (br s, 1H), 7.94 (d, J=2.1 Hz, 1H), 7.45 (m, 3H), 7.26 (d, J=8.5 Hz, 2H), 6.56 (d, J=8.6 Hz, 1H), 6.48 (d, J=1.9 Hz, 1H), 6.43 (m, 1H), 6.35 (m, 1H), 6.16 (m, 1H), 5.96 (m, 1H), 5.35 (m, 2H), 5.23 (s, 1H), 4.42 (m, 2H), 4.20 (m, 1H), 3.54 (m, 1H), 2.34 (m, 2H), 1.75 (d, J=7.1 Hz, 3H), 1.56 (m, 4H). Mass spectrum (LCMS, ESI pos.): Calcd for C$_{31}$H$_{29}$Cl$_2$IN$_2$O$_5$: 706.05; found 706.7 (M+H).

Example 55

5-[(3S)-3-(4-chloro-2-hydroxyphenyl)-4-[(R)-1-(4-chlorophenyl)ethyl]-7-iodo-2,5-dioxo-1,4-benzodiazepin-1-yl]valeric acid

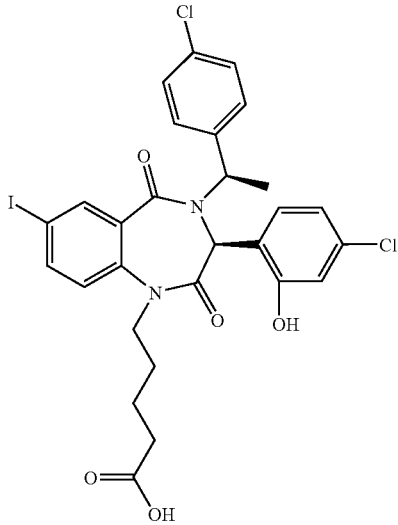

a) 5-[(3S)-3-(4-chloro-2-hydroxyphenyl)-4-[(R)-1-(4-chlorophenyl)ethyl]-7-iodo-2,5-dioxo-1,4-benzodiazepin-1-yl] valeric acid tert-butyl ester 5-[(3S)-3-(2-Allyloxy-4-chlorophenyl)-4-[(R)-1-(4-chlorophenyl)ethyl]-7-iodo-2,5-dioxo-1,4-benzodiazepin-1-yl] valeric acid tert-butyl ester (224 mg, 0.29 mmol) and dichloro bis(triphenylphosphine)palladium (II) (10 mg, 0.015 mmol) were dissolved at room temperature in THF (5 mL). Sodium borohydride (11 mg, 0.29 mmol) was added and the reaction was stirred under argon for 30 minutes. Methanol (10 mL) was added and the reaction was stirred for 15 additional minutes. The solvent was evaporated under vacuum and the residue was purified by column chromatography (AcOEt/Hexanes, 1:2) to give 200 mg of the title compound contaminated with 5-[(3S)-3-(2-Allyloxy-4-chlorophenyl)-4-[(R)-1-(4-chlorophenyl)ethyl]-2,5-dioxo-1,4-benzodiazepin-1-yl]valeric acid tert-butyl ester. This mixture was carried out to the next step without further purification.

b) 5-[(3S)-3-(4-Chloro-2-hydroxyphenyl)-4-[(R)-1-(4-chlorophenyl)ethyl]-7-iodo-2,5-dioxo-1,4-benzodiazepin-1-yl] valeric acid.

The title compound was synthesized from 5-[(3S)-3-(4-chloro-2-hydroxyphenyl)-4-[(R)-1-(4-chlorophenyl)ethyl]-7-iodo-2,5-dioxo-1,4-benzodiazepin-1-yl]valeric acid tert-butyl ester following the procedure for example 1, step b: $^1$H NMR (400 MHz, Cl$_3$CD) δ 7.99 (d, J=2.1 Hz, 1H), 7.42 (m, 3H), 7.22 (d, J=8.5 Hz, 2H), 6.62 (d, J=8.6 Hz, 1H), 6.50 (d, J=1.9 Hz, 1H), 6.34 (m, 2H), 6.09 (m, 1H), 5.26 (s, 1H), 3.87 (m, 1H), 3.74 (m, 1H), 2.39 (m, 2H), 1.75 (m, 7H). Mass spectrum (LCMS, ESI pos.): Calcd for C$_{28}$H$_{25}$Cl$_2$IN$_2$O$_5$: 666.02; found 666.6 (M+H); together with 21 mg 5-[(3S)-3-(4-chloro-2-hydroxyphenyl)-4-[(R)-1-(4-chlorophenyl) ethyl]-2,5-dioxo-1,4-benzodiazepin-1-yl]valeric acid:

$^1$H NMR (400 MHz, Cl$_3$CD) δ 7.67 (m, 1H), 7.41 (d, J=8.4 Hz, 2H), 7.21 (d, J=8.4 Hz, 2H), 7.15 (m, 1H), 7.06 (m, 1H), 6.88 (d, J=8.1 Hz, 1H), 6.54 (d, J=1.9 Hz, 1H), 6.35 (m, 1H), 6.27 (dd, J=1.9, J=8.4 Hz, 1H), 6.10 (d, J=8.4 Hz, 1H), 5.26 (s, 1H), 3.85 (m, 2H), 2.39 (m, 2H), 1.72 (m, 7H). Mass spectrum (LCMS, ESI pos.): Calcd for C$_{28}$H$_{26}$Cl$_2$N$_2$O$_5$: 540.1; found 540.8 (M+H).

Example 56

5-[(3S)-3-(4-Chlorophenyl)-4-[(R)-1-(4-chlorophenyl)ethyl]-2,5-dioxo-7-phenyl-1,4-diazepin-1-yl] valeric acid sodium salt

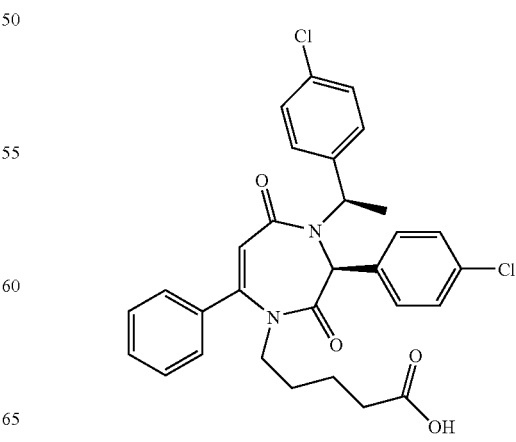

a) α-Bromo-α-(4-chlorophenyl)acetic acid methyl ester

A solution of 4-chlorophenylacetic acid methyl ester (14.6 g, 79.1 mmol), N-bromosuccinimide (14.4 g, 80.7 mmol), and benzoyl peroxide (1.91 g, 7.89 mmol) in carbon tetrachloride (100 mL) was heated at reflux for 3 h. After the mixture was cooled at room temperature, hexanes (500 mL) was added. The reaction mixture was filtered and the solvent was evaporated in vacuo. The crude material was purified by column chromatography on silica (EtOAc/Hexanes, 15:85) to give the title compound as colorless oil (16.9 g, 63%): $^1$H NMR (400 MHz, CDCl$_3$) δ 3.81 (s, 3H, CH$_3$), 5.34 (s, 1H, CH), 7.44 (dd, J=60.4 Hz, J=8.4 Hz, 4H, ArH).

b) α-(4-Chlorophenyl)-α-[(R)-N-[1-(4-chlorophenyl)ethyl]amino]acetic acid methyl ester hydrochloride A mixture of α-bromo-α-(4-chlorophenyl)acetic acid methyl ester (2.63 g, 10 mmol), (R)-1-(4-chlorophenyl)ethylamine (1.55 g, 10 mmol), potassium carbonate (2.76 g, 20 mmol), and tetrabutylammonium iodide (500 mg, 1.35 mmol) in dry acetonitrile (10 mL) was heated at 45° C. for 12 h. After the mixture was cooled at room temperature, the solvent was evaporated in vacuo. Then, the residue was partitioned between ice-cold water (50 mL) and ethyl acetate (70 mL). The aqueous layer was extracted twice with additional ethyl acetate (2×50 mL) and dried (Na2SO$_4$). After evaporation of the solvent, the residue was chromatographed on silica (EtOAc/hexanes, 5:95 to 15:85), then converted to the HCl salt to give the title compound as a colorless powder (2.5 g, 74%, mixture of two diastereomers): $^1$H NMR (400 MHz, CD$_3$OD) δ 1.74 (t, J=6.8 Hz, 3H, CH$_3$), 3.69 (s, 1.5 H, 0.5 CH$_3$), 3.82 (s, 1.5 H, 0.5 CH$_3$), 4.41 (q, J=6.8 Hz, 0.5 H, 0.5 CH), 4.49 (q, J=6.8 Hz, 0.5 H, 0.5 CH), 4.99 (s, 0.5 H, 0.5 CH), 5.12 (s, 0.5 H, 0.5 CH), 7.42–7.56 (m, 8H, ArH). Mass spectrum (LCMS, ESI pos.): Calcd for C$_{17}$H$_{17}$Cl$_2$NO$_2$: 337.0; found: 338.0 (M+H)$^+$.

c) (R,S)-α-(4-Chlorophenyl)-α-[(R)-N-[1-(4-chlorophenyl)ethyl]-N-(cinnamoyl)amino]acetic acid methyl ester To a stirred solution of (R,S)-α-(4-chlorophenyl)-α-[(R)-N-[1-(4-chlorophenyl)ethyl]amino]acetic acid methyl ester (1.0 g, 2.96 mmol) and 4-(N,N-dimethylamino)pyridine (100 mg, 0.82 mmol) in dichloromethane (30 mL) at 0° C. was added cinnamoyl chloride (542 mg, 3.25 mmol). Then, N,N-diisopropylethylamine (2.0 mL, 11.5 mmol) was slowly added. After 20 min. of stirring at 0° C., the reaction mixture was allowed warm up to 25° C. for 1 h., then diluted with ethyl acetate, washed with water, dried (Na$_2$SO$_4$), and concentrated to dryness under reduced pressure. Chromatography on silica (AcOEt/hexanes, 1:8) afforded the title compound (1.0 g, 74%) as a slightly yellow solid: Mass spectrum (LCMS, ESI pos.): Calcd for C$_{26}$H$_{23}$Cl$_2$NO$_3$: 467.0; found: 468.0 (M+H)$^+$.

d) α-(4-Chlorophenyl)-α-[(R)-N-[1-(4-chlorophenyl)ethyl]-N-(cinnamoyl)amino]acetic acid A solution of (R,S)-α-(4-chlorophenyl)-α-[(R)-N-[1-(4-chlorophenyl)ethyl]-N-(cinnamoyl)amino]acetic acid methyl ester (453 mg, 1.0 mmol) and sodium hydroxide (600 mg, 15.0 mmol) in tetrahydrofuran (5 mL), methanol (8 mL), and water (2 mL) was stirred for 2 h at 25° C. The reaction mixture was concentrated under reduced pressure and the pH adjusted to 4 with 1N HCl.

The resulting solution was extracted twice with AcOEt (20 mL), dried (Na$_2$SO$_4$) and evaporated to give the title compound as a colorless powder (420 mg, 92%, mixture of two diastereomers): $^1$H NMR (400 MHz, CDCl$_3$) δ 1.62 (d, J=7.0 Hz, 1.5 H, 0.5 CH$_3$), 1.84 (d, J=7.0 Hz, 1.5 H, 0.5 CH$_3$), 4.84 (s, 1H, CH), 4.88 (s, 1H, CH), 5.45–5.53 (m, 1H, CH), 6.93–7.91 (m, 15H, 13 ArH+2 CH). Mass spectrum (LCMS, ESI pos.): Calcd for C$_{25}$H$_{12}$Cl$_2$NO$_3$: 453.0; found: 454.0 (M+H)$^+$.

e) (S)-α-(4-Chlorophenyl)-α-[(R)-N-[1-(4-chlorophenyl)ethyl]-N-(cinnamoyl)amino]acetamide To a stirred solution of (R,S)-α-(4-Chlorophenyl)-α-[(R)-N-[1-(4-chlorophenyl)ethyl]-N-(cinnamoyl)amino]acetic acid (400 mg, 0.88 mmol), O-(7-azabenzotriazol-1-yl)-N,N,N',N'-tetramethyluronium hexafluorophosphate (502 mg, 1.32 mmol), ammonium chloride (94 mg, 1.76 mmol), and 1-hydroxybenzotriazole (178 mg, 1.32 mmol) in dimethylformamide (3mL) was slowly added N,N-diisopropylethylamine (613 μL, 3.52 mmol). After 2 h, the reaction mixture was partitioned between ethyl acetate (100 mL) and water (60 mL), dried (Na2SO$_4$), and evaporated. Purification by column chromatography (AcOEt/hexanes, 2:8) afforded the title compound (150 mg, 38%, "lower diastereomer in a TLC performed with AcOEt/Hexanes, 1:3") as a colorless solid: $^1$H NMR (400 MHz, CDCl$_3$) δ 1.86 (d, J=6.8 Hz, 3H, CH$_3$), 4.76 (s, 1H, CH), 5.40–5.49 (m, 1H, CH), 5.62 (br s, 1H, NH), 6.32 (br s, 1H, NH), 6.90–7.86 (m, 15H, 13 ArH+2 CH). Mass spectrum (LCMS, ESI pos.): Calcd for C$_{25}$H$_{22}$Cl$_2$N$_2$O$_2$: 452.0; found: 453.0 (M+H)$^+$.

f) (3S)-1,3,6,7-Tetrahydro-3-(4-chlorophenyl)-4-[(R)-1-(4-chlorophenyl)ethyl]-7-phenyl-6-(phenylseleno)-1,4-diazepine-2,5-dione Silver triflate (1.69 g, 6.6 mmol) was added to a stirred solution of (S)-α-(4-chlorophenyl)-α-[(R)-N-[1-(4-chlorophenyl)ethyl]-N-(cinnamoyl)amino]acetamide (1.5 g, 3.3 mmol), in acetonitrile (120 mL). To the resulting solution was successively added benzeneselenyl bromide (1.54 g, 6.53 mmol) and dimethylformamide (5.2 mL). After 6 h, the solvent was evaporated in vacuo. The residue was partitioned between ethyl acetate (100 mL) and 1N sodium hydrogenocarbonate (70 mL), dried (Na$_2$SO$_4$), and evaporated. Purification by column chromatography (AcOEt/hexanes, 1:3) afforded the title compound, which was recrystallized from Et$_2$O to give colorless prisms (855 mg, 43%): $^1$H NMR (400 MHz, CDCl$_3$) δ 1.68 (d, J=7.0 Hz, 3H, CH$_3$), 4.29 (d, J=12.2 Hz, 1H, CH), 4.79 (d, J=12.2 Hz, 1H, CH), 5.28 (s, 1H, CH), 6.21–6.25 (m, 3H, ArH), 6.31 (q, J=7.0 Hz, 1H, CH), 6.71–6.76 (m, 4H, ArH), 6.93–7.11 (m, 6H, NH+5ArH), 7.34–7.40 (m, 4H, ArH), 7.50 (d, J=8.4 Hz, 2H, ArH). Mass spectrum (LCMS, ESI pos.): Calcd for C$_{31}$H$_{26}$Cl$_2$N$_2$O$_2$Se: 608.0; found: 609.0 (M+H)$^+$.

g) (3S)-1,3-Dihydro-3-(4-chlorophenyl)-4-[(R)-1-(4chlorophenyl)ethyl]-7-phenyl-1,4-diazepine-2,5-dione Hydrogen peroxide (500 μL, 30% in water) was slowly added to a solution of (3S)-1,3,6,7-tetrahydro-3-(4-chlorophenyl)-4-[(R)-1-(4-chlorophenyl)ethyl]-7-phenyl-6-(phenylseleno)-1,4-diazepine-2,5-dione (300 mg, 0.49 mmol) in tetrahydrofuran (6 mL). After 20 min., the solvent was evaporated under reduced pressure and the residue was partitioned between 1N sodium hydrogenocarbonate (20 mL) and ethyl acetate (50 mL), dried (Na$_2$SO$_4$) and evaporated. Purification by column chromatography (AcOEt/hexanes/CH$_2$Cl$_2$, 1:2:2) afforded the title compound (200 mg, 85%) as a colorless powder: $^1$H NMR (400 MHz, CDCl$_3$) δ 1.70 (d, J=7.2 Hz, 3H, CH$_3$), 5.28 (s, 1H, CH), 5.70 (d, J=1.6 Hz, 1H, CH), 6.35 (q, J=7.2 Hz, 1H, CH), 6.83 (d, J=8.8 Hz, 2H, ArH), 7.09 (d, J=8.8 Hz, 2H, ArH), 7.18–7.42 (m, 7H, ArH), 7.53 (d, J=8.8 Hz, 2H, ArH). Mass spectrum (LCMS, ESI pos.): Calcd for C$_{25}$H$_{20}$Cl$_2$N$_2$O$_2$: 450.0; found: 451.0 (M+H)$^+$.

h) 5-[(3S)-3-(4-Chlorophenyl)-4-[(R)-1-(4-chlorophenyl)ethyl]-2,5-dioxo-7-phenyl-1,4-diazepin-1-yl]valeric acid sodium salt.

The title compound was synthesized from (3S)-1,3-Dihydro-3-(4-chlorophenyl)-4-[(R)-1-(4-chlorophenyl)ethyl]-7-phenyl-1,4-diazepine-2,5-dione following the general procedure for the alkylation of the 1-position, followed by deprotection following the procedure for example 1, step b: $^1$H NMR (400 MHz, CDCl$_3$) δ 1.45–1.53 (m, 4H, 2 CH$_2$), 1.68 (d, J=7.2 Hz, 3H, CH$_3$), 2.29 (t, J=6.8 Hz, 2H, CH$_2$), 2.87–2.93 (m, 1H, CH), 4.15–4.23 (m, 1H, CH), 5.40 (s, 1H, CH), 5.72 (s, 1H, CH), 6.32 (q, J=7.2 Hz, 1H, CH), 6.81 (d, J=7.6 Hz, 2H, ArH), 7.02–7.08 (m, 4H, ArH), 7.26–7.34 (m, 5H, ArH), 7.48 (d, J=8.4 Hz, 2H, ArH). Mass spectrum (LCMS, ESI pos.): Calcd for C$_{30}$H$_{28}$Cl$_2$N$_2$O$_4$: 550.0; found: 551.0 (M+H)$^+$.

Example 57

5-[(3S)-7-(2-Bromophenyl)-3-(4-chlorophenyl)-4-[(R)-1-(4-chlorophenyl)ethyl]-2,5-dioxo-1,4-diazepin-1-yl]valeric acid sodium salt.

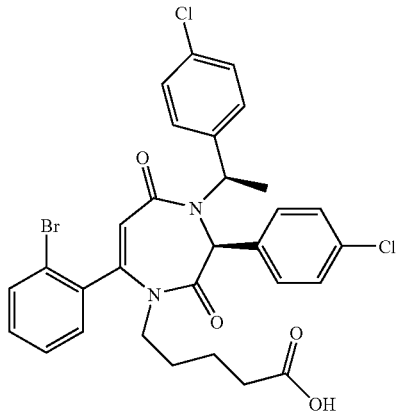

$^1$H NMR (400 MHz, CDCl$_3$) δ 1.46–1.53 (m, 4H, 2 CH$_2$), 1.69 (d, J=7.2 Hz, 3H, CH$_3$), 2.29 (t, J=6.8 Hz, 2H, CH$_2$), 2.87–2.93 (m, 1H, CH), 4.15–4.23 (m, 1H, CH), 5.41 (s, 1H, CH), 5.66 (s, 1H, CH), 6.31 (q, J=7.2 Hz, 1H, CH), 6.88 (d, J=7.6 Hz, 2H, ArH), 7.10–7.60 (m, 10H, ArH). Mass spectrum (LCMS, ESI pos.): Calcd for C$_{30}$H$_{27}$BrCl$_2$N$_2$O$_4$: 628.0; found: 629.0 (M+H)$^+$.

Example 58

5-[(3S)-3-(4-Chlorophenyl)-4-[(R)-1-(4-chlorophenyl)ethyl]-7-(2,5-dimethylphenyl)-2,5-dioxo-1,4-diazepin-1-yl]valeric acid sodium salt.

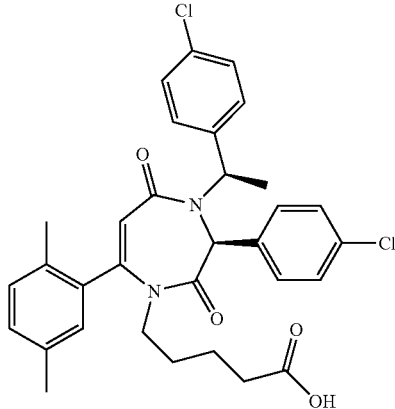

$^1$H NMR (400 MHz, CDCl$_3$) δ 1.43–1.63 (m, 4H, 2 CH$_2$), 1.70 (d, J=7.2 Hz, 3H, CH$_3$), 2.04 (s, 3H, CH$_3$), 2.12 (s, 3H, CH$_3$), 2.27–2.34 (m, 2H, CH$_2$), 2.87–2.93 (m, 1H, CH), 4.15–4.23 (m, 1, CH), 5.51 (s, 1H, CH), 5.75 (s, 1; H, CH), 6.26 (q, J=7.2 Hz, 1H, CH), 6.77 (d, J=7.6 Hz, 2H, ArH), 6.80–7.65 (m, 9H, ArH). Mass spectrum (LCMS, ESI pos.): Calcd for C$_{32}$H$_{32}$Cl$_2$N$_2$O$_4$: 578.0; found: 5.79.0 (M+H)$^+$.

Example 59

5-[(3S)-3-(4-Chlorophenyl)-4-[(R)-1-(4-chlorophenyl)ehtyl]-7-(2-methylphenyl)-2,5-dioxo-1,4-benzodiazepipne-1-yl]valeric acid sodium salt

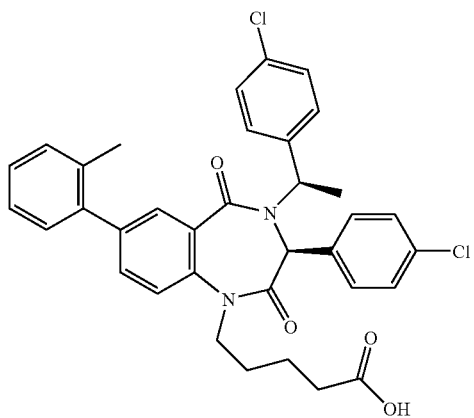

a) (3S)-3-(4-Chlorophenyl)-4-[(R)-1-(4-chlorophenyl)ethyl]-7-(2-methylphenyl)-1,4-benzodiazepine-2,5-dione A solution of (3S)-3-(4-chlorophenyl)-4-[(R)-1-(4-chlorophenyl)ethyl]-7-iodo-1,4-benzodiazepine-2,5-dione (120 mg, 0.22 mmol), tetrakis(triphenylphosphine)palladium(0) (25 mg, 0.022 mmol), 2-methylbenzene boronic acid (35 mg, 0.26 mmol) and sodium carbonate (220 μL, 2M in H$_2$O) in ethanol (300 μL) and toluene (5 mL) was heated under argon, at 90° C., for 10 h. After the mixture was cooled at room temperature, the solvent was evaporated in vacuo. The residue was partitioned between AcOEt (20 mL) and water (15 mL), dried (Na$_2$SO$_4$) and evaporated. Chromatography on silica (AcOEt/hexanes/CH$_2$Cl$_2$, 1:6:3) afforded the title compound (92 mg, 68%) as a colorless powder: $^1$H NMR (400 MHz, CDCl$_3$) δ 1.78 (d, J=7.2 Hz, 3H, CH$_3$), 1.99 (s, 3H, CH$_3$), 5.29 (s, 1H, CH), 6.51 (q, J=7.2 Hz, 1H, CH), 6.64–6.67 (m, 2H, ArH, 6.71 (d, J=8.4 Hz, 1H, ArH), 6.93 (d, J=8.4 Hz, 2H, ArH), 7.05–7.11 (m, 1H, ArH), 7.15 (dd, J=8.0 Hz, J=2.0 Hz, 1H, ArH), 7.20–7.26 (m, 3H, ArH), 7.35 (d, J=8.4 Hz, 2H, ArH), 7.56 (d, J=8.4 Hz, 2H, ArH), 7.61 (d, J=2.0 Hz, 1H, ArH), 7.91 (br s, 1H, NH). Mass spectrum (LCMS, ESI pos.): Calcd for C$_{30}$H$_{24}$Cl$_2$N$_2$O$_2$: 514.0; found: 515.0 (M+H)$^+$.

b) 5-[(3S)-3-(4-Chloropghenyl)-4-[(R)-1-(4-chlorophenyl)ethyl]-7-(2-methylphenyl)-2,5-dioxo-1,4-benzoepin-1-yl] valeric acid sodium salt.

The title compound was prepared from (3S)-3-(4-chlorophenyl)-4-[(R)-1-(4-chlorophenyl)ethyl]-7-(2-methylphenyl)-1,4-benzodiazepine-2,5-dione following successively the general procedure for the alkylation at the 1-position followed by the deprotection procedure described for example 1, step b: $^1$H NMR (400 MHz, CDCl$_3$) δ 1.65 (m, 7H, CH₃+2 CH₂), 1.98 (s, 3H, CH₃), 2.41 (t, J=7.6 Hz, 2H, CH₂), 3.70–3.77 (m, 1H, CH), 4.39–4.46 (m, 1H, CH), 5.37 (s, 1H, CH), 6.44 (q, J=7.2 Hz, 1H, CH), 6.50–6.53 (m, 2H, ArH), 6.86 (d, J=8.8 Hz, 2H, ArH), 6.91 (d, J=8.4 Hz, 1H, ArH), 7.06–7.15 (m, 2H, ArH), 7.20–7.26 (m, 3H, ArH), 7.32 (d, J=8.4 Hz, 2H, ArH), 7.50–7.52 (m, 3H, ArH). Mass spectrum (LCMS, ESI pos.): Calcd for $C_{35}H_{32}Cl_2N_2O_4$: 614.0; found: 615.0 (M+H)⁺.

Example 60

5-[4-[1-(2-Amino-4-chlorophenyl)ethyl]-3-(4-chlorophenyl)-7-iodo-2,5-dioxo-1,4-benzodiazepin-1-yl] valeric acid sodium salt

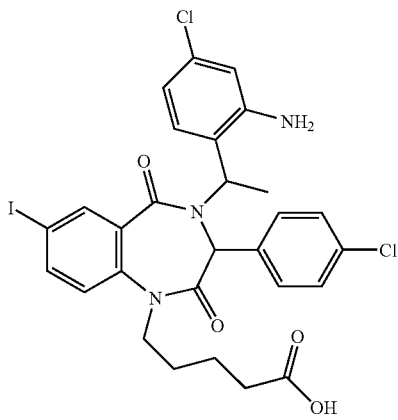

a) 1-(4-Chloro-2-nitrophenyl)ethanol

A solution of methyl lithium (46 mL, 1.4 M in Et₂O), was slowly added under argon, at –78° C., to a stirred solution of 4-chloro-2-nitrobenzaldehyde (10 g, 53.9 mmol) in dry tetrahydrofuran (150 mL). After 20 min. at –78° C., the reaction mixture was quenched with water (400 mL), extracted twice with ethyl acetate (500 mL), dried (Na₂SO₄), and concentrated to dryness under reduced pressure. Chromatography on silica (EtOAc/CH₂Cl₂/EtOH, 1:6:1) yielded the title compound (7.2 g, 66%) as yellow oil: ¹H NMR (400 MHz, CDCl₃) δ 1.56 (d, J=6.4 Hz, 3H, ArH), 2.40 (br s, 1H, OH), 5.42 (q, J=6.4 Hz, 1H, CH), 7.63 (dd, J=8.4 Hz, J=2.0 Hz, 1H, ArH), 7.82 (d, J=8.4 Hz, 1H, ArH), 7.92 (d, J=2.0 Hz, 1H, ArH).

b) [(S)-1-(4-Chloro-2-nitrophenyl)ethyl] (1S)-camphanoate and [(R)-1-(4-Chloro-2-nitrophenyl)ethyl](1S)-camphanoate Diisopropylethylamine (9.3 mL, 53.3 mmol) was slowly added at 0° C. under argon to a solution of (R,S)-1-(4-chloro-2-nitrophenyl)ethanol (10.2 g, 50.8 mmol), 4-dimethylaminopyridine (244 mg, 2.0 mmol) and (1S)-camphanyl chloride (11.0 g, 50.8 mmol) in tetrahydrofuran (70 mL). Then, the reaction mixture was allowed warm up to room temperature. After 8 h, the solvent was evaporated in vacuo and the residue was partitioned between CH₂Cl₂ and 1N NaHCO₃, dried (Na₂SO4) and filtered through silica gel. The solvent was evaporated under reduced pressure. The residue was dissolved in chloroform (100 mL), then hexanes (300 mL) was slowly added. After 10 min, the title compound started to crystallize. After 20 min, the prisms were filtered off and washed with small protions of dichloromethane/hexanes (1:5). This compound (4.8 g, 25%) was characterized as the title compound: ¹HNMR (400 MHz, CDCl₃) δ 1.03 (s, 3H, CH₃), 1.07 (s, 3H, CH₃), 1.15 (s, 3H, CH₃), 1.70 (d, J=6.4 Hz, 4H, 2 CH₂), 1.88–2.01 (m, 2H, CH₂), 2.35–2.42 (m, 1H, CH), 6.52 (q, J=6.4 Hz, 1H, CH), 7.64 (dd, J=8.8 Hz, J=2.4 Hz, 1H, ArH), 7.71 (d, J=8.8 Hz, 1H, ArH), 7.99 (d, J=2.0 Hz, 2H, ArH). The filtrte was evaporated and the residue recrystallized in ether to give the other diastereomer [(R)-1-(4-Chloro-2-nitrophenyl)ethyl] (1S)-camphanoate.

c) (R,S)-N-[1-(4-Chloro-2-nitrophenyl)ethyl]phthalimide

Diisopropyl azodicarboxylate (1.46 mL, 7.44 mmol) was added under argon, at –78° C., to a solution of (R,S)-1-(4-chloro-2-nitrophenyl)ethanol (1.0 g, 4.96 mmol), triphenyl phosphine (730 mg, 4.96 mmol) and phthalimide (730 mg, 4.96 mmol) in tetrahydrofuran (20 mL). Then, the reaction mixture was allowed warm up to 25° C. After 2 h, the solvent was evaporated under reduced pressure. Chromatography on silica (AcOEt/hexanes, 1:1) afforded the title compound (1.4 g, 85%) as a colorless solid: ¹H NMR (400 MHz, CDCl₃) δ 1.97 (d, J=7.2 Hz, 3H, CH₃), 6.04 (q, J=7.2 Hz, 1H, ArH), 7.58–7.61 (m, 1H, ArH), 7.72–7.75 (m, 2H, ArH), &.81–7.84 (m, 3H, ArH), 7.81 (d, J=8.8, 1H, ArH).

d) (R,S)-1-(4-Chloro-2-nitrophenyl)ethylamine

A mixture of (R,S)-N-[1-(4-chloro-2-nitropheyl)ethyl]phthalimide (1.2 g, 3.63 mmol) and hydroazine (1.2 mL, 3.82 mmol) in ethanol (10 mL) was heated at reflux for 1 h. After the mixture was cooled at room temerature, the precipitated was filtered off and the solvent was evaporated in vacuo. The crude material was purified by column chromatography on silica (tOAc/EtOH/CH₂Cl₂, 4:1:5) to give the title compound (600 mg, 82%) as a colorless oil: ¹H NMR (400 MHz, CDCl₃) δ 1.44 (d, J=6.5 Hz, 3H, CH₃), 1.58 (br s, 2H, NH₂), 4.60 (q, J=6.5 Hz, 1H, CH), 7.58 (dd, J=8.8 Hz, J=2.0 Hz, 1H, ArH), 7.79–7.81 (m, 2H, ArH).

e) 5-[3-(4-Chlorophenyl)-4-[1-(4-chloro-2-nitrophenyl)ethyl]-7-iodo-2,5-dioxo-1,4-benzoazepin-1-yl]valeric acid tert-butyl ester The title compound was prepared from (R,S)-1-(4-chloro-2-nitrophenyl)ethylamine following the general proceuder for the syunthesis of diazepines: ¹H NMR (400 MHz, CDCl₃) δ 1.45 (s, 9H, 3 CH₃), 1.60–1.69 (m, 4H, 2 CH₂), 1.79 (d, J=6.8 Hz, 3H, CH₃), 2.22 (t, J=7.0 Hz, 2H, CH₂), 3.58–3.67 (m, 1H, ArH), 6.62–6.70 (m, 3H, 2 ArH+CH), 6.94 (d, J=8.8 Hz, 2H, ArH), 7.45 (dd, J=8.4 Hz, J=2.0 Hz, 1H, ArH), 7.56 (dd, J=8.8 Hz, J=2.4 Hz, 1H, ArH), 7.67 (d, J=8.4 Hz, 1H, ArH), 7.86 (d, J=2.4 Hz, 1H, ArH), 7.97 (d, J=2.0 H, 1H, ArH).

f) 5-[4-[1-(2-Amino-4-chlorophenyl)ethyl]-3-(4-chlorophenyl)-7-iodo-2,5-dioxo-1,4-benzodiazepin-1-yl]valeric acid tert-butyl ester A solution of ammonium chloride (220 mg, 4.3 mmol) in water (2.5 mL) was added to a solution of 5-[3-(4-chlorophenyl)-4-[1-(4-chloro-2-nitrophenyl)ethyl]-7-iodo-2,5-dioxo-1,4-benzodiazepin-1-yl]valeric acid tert-butyl ester (230 mg, 0.306 mmol) in ethanol (5 mL). The resulting solution was heated to 80° C. and iron (200 mg, 3.58 mmol) was added. After 2 h at 80° C., the reaction mixture was cooled at room temperature, filtered through celite and evaporated. The residue was partitioned between ethyl acetat and water, dried (Na₂SO₄), and evaporated. Chromatography on silica (EtOAc/hexans, 1:1) afforded the title compound (210 mg, 95%) as a colorless solid: ¹H NMR (400 MHz, CDCl₃) δ 1.44 (s, 9H, 3 CH₃)), 1.57–1.63 (m, 4H, 2 CH₂), 1.74 (d, J=7.2 Hz, 3H, CH₃), 2.24 (t, J=7.2 Hz, 2H, CH₂), 3.63–3.70 (m, 1H, CH), 4.28–4.35 (m, 1H, CH), 4.75 (br s, 2H, NH$_2$), 5.28 (s, 1H, CH), 6.27 (q, J=7.2 Hz, 1H, CH), 6.60–6.69 (m, 5H, ArH), 6.90 (d, J=9.2 Hz, 2H, ArH), 7.20 (d, J=8.4 Hz, 1H, ArH), 7.49 (dd, J=8.8 Hz, J=2.4 Hz, 1H, ArH), 7.93 (d, J=2.0 Hz, 1H, ArH). Mass spectrum (LCMS, ESI pos.): Calcd for C$_{32}$H$_{34}$Cl$_2$IN$_3$O$_4$: 721.0; found: 722.0 (M+H)$^+$.

g) 5-[4-[1-(2-Amino-4-chlorophenyl)ethyl]-3-(4-chlorophenyl)-7-iodo-2,5-dioxo-1,4-benzodiazepin-1-yl]valeric acid sodium salt The title compound was prepared (76%) from 5-[4-[1-(2-amino-4-chlorophenyl)ethyl]-3-(4-chlorophenyl)-7-iodo-2,5-dioxo-1,4-benzodiazepin-1-yl]valeric acid tert-butyl ester following the procedure described for example 1, step b: $^1$H NMR (400 MHz, CDCl$_3$) δ 1.63–1.68 (m, 4H, 2 CH$_2$), 1.75 (d, J=6.8 Hz, 3H, CH$_3$), 2.37–2.41 (m, 2H, CH$_2$), 3.64–3.71 (m, 1H, CH), 4.33–4.40 (m, 1H CH), 5.29 (s, 1H, CH), 6.26 (q, J=6.8 Hz, 1H, CH), 6.61–6.68 (m, 5H, ArH), 6.90 (d, J=8.8 Hz, 2H, ArH), 7.21 (d, J=8.4 Hz, 1H, ArH), 7.50 (dd, J=8.8 Hz, 1H, ArH), 7.93 (d, J=2.0 Hz, 1H, ArH). Mass spectrum (LCMS, ESI pos.): Calcd for C$_{28}$H$_{26}$Cl$_2$IN$_3$O$_4$: 665.0; found: 666.0 (M+H)$^+$.

Example 61

5-[4-[(2-Amino-4-chlorobenzyl]-7-bromo-3-(4-chlorophenyl)-2,5-dioxo-1,4-benzodiazepin-1-yl]valeric acid sodium salt

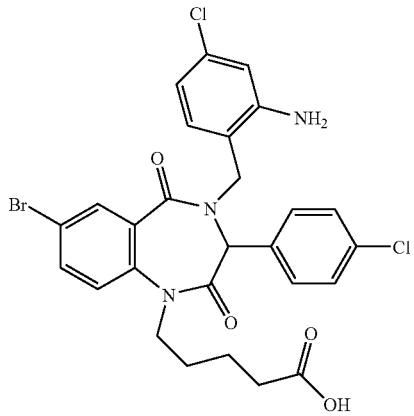

a) 5-[7-Bromo-3-(4-chlorophenyl)-4-[(4-chloro-2-nitrobenzyl]-2,5-dioxo-1,4-benzodiazepin-1-yl]valeric acid tert-butyl ester The title compound was prepared (63%) from 5-[7-bromo-3-(4-chlorophenyl)-3,4-dihydro-2,5-dioxo-1,4-benzodiazepin-1-yl]valeric acid tert-butyl ester and 4-chloro-2-nitrobenzyl chloride following the procedure described for the general procedure for the dialkylation of the benzodiazepine: Mass spectrum (LCMS, ESI pos.): Calcd for C$_{31}$H$_{30}$BrCl$_2$N$_3$O$_6$: 689.0; found: 690.0 (M+H)$^+$.

b) 5-[4-(2-Amino-4-chlorobenyl)-7-bromo-3-(4-chlorophenyl)-2,5-dioxo-1,4-benzodiazepin-1-yl]valeric acid sodium salt.

The title compound was prepared (46%) from 5-[7-bromo-3-(4-chloropehnyl)-4-[(4-chloro-2-nitrophenyl)methyl]-2,5-dioxo-1,4-benzodiazepin-1-yl]valeric acid tert-butyl ester following successively the procedure described for example 60, step e, f: $^1$H NMR (400 MHz, CDCl$_3$) δ 1.62–1.78 (m, 4H, 2 CH$_2$), 2.36–2.40 (m, 2H, CH$_2$), 3.66–3.73 (m, 1H, CH), 4.24–4.31 (m, 1H, CH), 4.37 (d, J=14.8 Hz, 1H, CH), 5.39 (s, 1H, CH), 5.42 (d, J=14.8 Hz, 1H, CH), 6.60 (dd, J=8.4 Hz, J=2.4 Hz, 1H, ArH), 6.68–6.71 (m, 3H, ArH), 6.80 (d, J=8.8 Hz, 1H, ArH), 6.97 (d, J=8.4 Hz, 2H, ArH), 7.07 (d, J=8.4 Hz, 1H, ArH), 7.34 (dd, J=8.8 Hz, J=2.4 Hz, 1H, ArH), 7.74 (d, J=2.4 Hz, 1H, ArH). Mass spectrum (LCMS, ESI pos.): Calcd for C$_{27}$H$_{24}$BrCl$_2$N$_3$O$_4$: 603.0; found: 604.0 (M+H)$^+$.

Example 62

4-(4-Chloro-benzyl)-3-(4-chloro-phenyl)-7-iodo-3,4-dihydro-1H-benzo[e][1,4]diazepine-2,5-dione

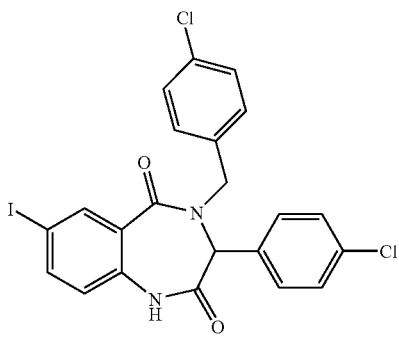

$^1$H NMR (400 MHz, CDCl$_3$) δ 8.09 (s, 1H), 7.87 (s, 1H), 7.52 (d, J=8.3 Hz, 1H), 7.44–7.37 (br m, 2H), 7.36–7.30 (m, 2H), 7.10–7.04 (m, 2H), 6.87–6.77 (br m, 2H), 6.43 (d, J=8.3 Hz, 1H), 5.33 (s, 1H), 5.03–4.91 (m, 2H). Mass Spectrum (LCMS, ESI, pos.): calcd. for C$_{22}$H$_{15}$Cl$_2$IN$_2$O$_2$: 535.9; found 537.03 (M+H).

Example 63

4-(R)-[1-(2-Amino-4-chloro-5-fluoro-phenyl)-ethyl]-3-(S)-(4-chloro-phenyl)-7-iodo-1-(2-morpholin-4-yl-ethyl)-3,4-dihydro-1H-benzo[e][1,4]diazepine-2,5-dione

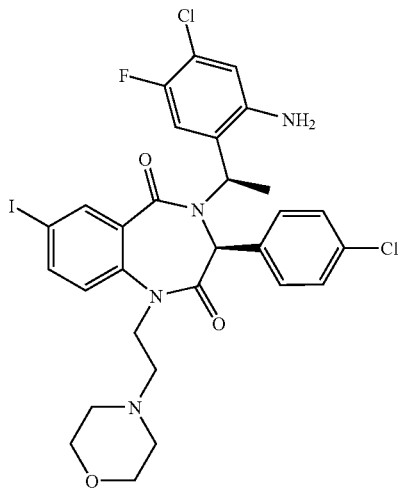

a) 1-(4-Chloro-3-fluoro-phenyl)-ehtnaol

4-Chloro-3-fluoro-benzaldehyde (5.14 g, 32.4 mmol) was dissolved in THF (100 mL) and place at −78° C. under nitrogen atmosphere. Methyl Lithium (1.6 M in diethyl ether, 22.3 mL) was added to the reaction during a period of 3 minutes maintianing the same temperature. After the addition, the reaction was stirred at room temperature for 1 h. Then, the reaction was poured over ice water and extracted with ethyl acetate and hydrochloric acid 1N. The organic layer was collected, dried with sodium sulfate, filtered and concentrated under vacuum to produce a crude, which it was chromatograph over silica gel using 50% hexane-ethyl Acetate as solvent to yield 5.1 g of 1-(4-chloro-3-fluoro-phenyl)-ethanol. $^1$H NMR (400 MHz, Cl$_3$CD) δ 7.37 (t, J=8.14 Hz, 1H), 7.20 (dd, J=1.86, 10.00 Hz, 1H), 7.09 (dd, J=1.86, 8.14 Hz, 1H), 4.89 (m, 1H), 1.93 (br s, 1H), 1.49 (d, J=6.51, 3H).

b) 2-[1-(4-Chloro-3-fluoro-phenyl)-ethyl]-isoindole-1,3-dione 1-(4-Chloro-3-fluoro-phenyl)-ehtanol (5.1 g, 29.2 mmol), phthalimide (4.3 g, 29.2 mmol) and triphenylphosphine (11.49 g, 43.8 mmol) were dissolved in THF (100 ml) and place at −78° C. under nitrogen atmosphere. Then, diisopropyl azodicarboxylate (8.86 g, 43.8 mmol) was added in one shot. The reaction was place at room temperature and stirred for 30 minutes. The solvent was evaporated and the crude was chromatograph over silica gel using 70% hexane-ethyl acetate as solvent to yield 4.08 g of 2-[1-(4-Chloro-3-fluoro-phenyl)-ethyl]-isoindole-1,3-dione. $^1$H NMR (400 MHz, Cl3CD) δ 7.83 (m, 2H), 7.73 (m, 2H), 7.34 (m, 2H), 7.21 (dd, J=1.93, 8.14 Hz, 1H), 5.53 (m, 1H), 1.91 (d, J=7.29, 3H).

c) 1-(4-Chloro-3-fluoro-phenyl)-ethylamine

2-[1-(4-Chloro-3-fluoro-phenyl)-ethyl]-isoindole-1,3-dione (4.08 g, 13.4 mmol) was dissolved in THF (100 mL). Hydrazine (4 mL) was added. The reaction was stirred at 80° C. for 1 h. Then, the solvent was evaporated and the crude was chromatograph over silica gel using ethyl acetate as solvent to yield 2.0 g of 1-(4-chloro-3-fluoro-phenyl)-ehtylamine. $^1$H NMR (400 Hz, Cl3CD) δ 7.34 (t, J=7.97 Hz, 1H), 7.18 (dd, J=1.90, 10.25 Hz, 1H), 7.08 (dd, J=1.90, 7.97 Hz, 1H), 4.12 (m, 1H), 1.36 (d, J=6.64, 3H).

d) N-[1-(4-Chloro-3-fluoro-phenyl)-ethyl]-2,2,2-trifluoro-acetamide 1-(4-Chloro-3-fluoro-phenyl)-ethylamine (2.0 g, 11.5 mmol) was dissolved in pyridine (20 ml) and place at 0° C. under nitrogen atmosphere. Then, trifluoroacetic anhydride (3.63 g, 17.2 mmol) was added in one shot. The reaction was allowed to reach room temperature and stirred for 16 h. The solvent was removed under vacuum and the crude was extracted with ethyl acetate-sodium hydroxide 1N. The organic layer was collected and extracted again using hydrochloric acid (1N) and brine. The organic layer was collected, dried with sodium sulfate, filtered and concentrated under vacuum to produce a crude, which it was chromatograph over silica gel using 50% hexane-ethyl acetate as solvent to yield 1.374 g of N-[1-(4-chloro-3-fluoro-phenyl)-ethyl]-2,2,2-trifluoro-acetamide. $^1$H NMR (400 MHz, Cl3CD) δ 7.49 (d, J=7.29 Hz, 1H), 7.35 (t, J=7.92 Hz, 1H), 7.11 (dd, J=1.93, 9.86 Hz, 1H), 7.04 (dd, J=1.93, 7.29 Hz, 1H), 5.06 (m, 1H), 1.53 (d, J=7.07, 3H).

e) N-[1-(4-Chloro-3-fluoro-2-nitro-phenyl)-ethyl]-2,2,2-trifluoro-acetamide

N-[1-(4-Chloro-3-fluoro-phenyl)-ethyl]-2,2,2-trifluoro-acetamide (1.374 g, 5.09 mmol) was dissolved at room temperature in concentrated sulfuric acid (25 mL). The solution was place at 0° C. using an ice water bath, and potassium nitride (0.567 mg, 5.60 mmol) was added. The reaction was stirred at the same temperature for 15 minutes and then allowed to reach room temperature and stirred for 16 h. Then, the reaction was poured over ice water and extracted with ethyl Acetate-water. The organic layer was collected and extracted again using sodium hydroxide (1N) and brine. The organic layer was collected, dried with sodium sulfate, filtered and concentrated under vacuum to produce a crude, which it was chromatograph over silica gel using 80% hexane-ethyl acetate as solvent to yield 1.13 g of N-[1-(4-chloro-3-fluoro-2-nitro-phenyl)-ethyl]-2,2,2-trifluoro-acetamide.
$^1$H NMR (400 MHz, C13CD) δ 8.16 (d, J=6.43 Hz, 1H), 7.30 (d, J=9.00 Hz, 1H), 7.08 (br s, 1H), 5.52 (m, 1H), 1.65 (d, J=7.07, 3H).

f) 1-(4-Chloro-3-fluoro-2-nitro-phenyl)-ethylamine

N-[1-(4-Chloro-3-fluoro-2-nitro-phenyl)-ethyl]-2,2,2-trifluoro-acetamide (286 mg, 0.909 mmol) was dissolved at room temperature in THF (10 mL). Then, a solution of lithium hydroxide monohydrate (46 mg, 1.09 mmol) in water (2 mL) was added. The reaction was followed by TLC, using ethyl acetate as solvent. After 2 h., more lithium hydroxide monohydrate (46 mg, 1.09 mmol) in water (2 mL) was added. The reaction was stirred at room temperature for three days. Then, the reaction was extracted with ethyl acetate-sodium hydroxide (1N) and brine. The organic layer was collected, dried with sodium sulfate, filtered and concentrated under vacuum to produce a crude, which it was chromatograph over silica gel to yield 148 mg of 1-(4-chloro-3-fluoro-2-nitro-phenyl)-ethylamine. $^1$H NMR (400 MHz, Cl3CD) δ 7.90 (d, J=6.43 Hz, 1H), 7.64 (d, J=10.07 Hz, 1H), 4.62 (m, 1H), 1.58 (br s, 2H), 1.33 (d, J=6.43, 3H).

g) 4-(R,S)-[1-(2-Amino-4-chloro-5-fluoro-phenyl)-ethyl]-3-(S,R)-(4-chloro-phenyl)-7-iodo-1-(2-morpholin-4-yl-ethyl)-3,4-dihydro-1H-benzo[e][1,4]diazepine-2,5-dione The title compound was synthesized following the general procedure for the synthesis of diazepines. $^1$H NMR (400 MHz, Cl3CD) δ 7.79 (d, J=1.93 Hz, 1H), 7.57 (dd, J=1.93, 6.64 Hz, 1H), 7.32 (d, J=10.23 Hz, 1H), 7.03 (d, J=6.64 Hz, 1H), 6.85 (m, 3H), 6.57 (d, J=8.36 Hz, 2H), 6.10 (m, 1H), 5.54 (s, 1H), 4.42 (m, 1H), 4.23 (m, 1H), 3.97 (br s, 2H), 3.74 (br s, 2H), 3.46 (m, 6H), 1.67 (d, J=7.07 Hz, 3H). Mass spectrum (LCMS, ESI pos.): Calcd for $C_{29}H_{28}Cl_2FIN_4O_3$: 696.06; found 696.9 (M+H).

Example 64

4-(R,S)-[1-(2-Amino-4-chloro-5-hydroxy-phenyl)-ethyl]-3-(S,R)-(4-chloro-phenyl)-7-iodo-1-(2-morpholin-4-yl-ehtyl)-3,4-dihydro-1H-benzo[e][1,4]diazepine-2,5-dione

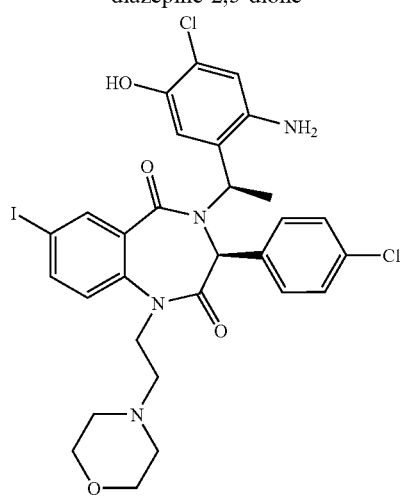

This compound was obtained as bi-product from Example 63 (step g). ¹H NMR (400 MHz, Cl3CD) δ 7.82 (d, J=1.93 Hz, 1H), 7.59 (dd, J=1.93, 8.79 Hz, 1H), 7.31 (s, 1H), 7.02 (s, 1H), 6.88 (m, 3H), 7.37 (d, J=8.57 Hz, 2H), 6.05 (m, 1H), 5.76 (s, 1H), 4.41 (m, 1H), 4.24 (m, 1H), 3.97 (br s, 2H), 3.75 (br s, 2H), 3.47 (m, 6H), 1.75 (d, J=6.86 Hz, 3H). Mass spectrum (LCMS, ESI pos.): Calcd for $C_{29}H_{29}Cl_2IN_4O_4$: 694.06; found 694.9 (M+H).

Example 65

3(S)-(4-Chloro-2-hydroxy-phenyl)-4(R)-[1-(4-chloro-phenyl)-ethyl]-7-iodo-3,4-dihydro-1H-benzo[e][1,4]diazepine-2,5-dione

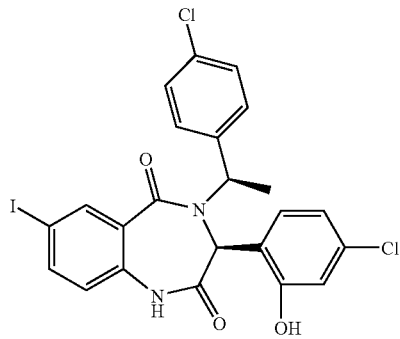

¹H NMR (400 MHz, Cl3CD) δ 8.97 (s, 1H), 8.03 (d, J=1.93 Hz, 1H), 7.66 (br s, 1H), 7.34 (d, J=8.57 Hz, 2H), 7.21 (dd, J=1.93, 8.36 Hz, 1H), 7.16 (d, J=8.36 Hz, 2H), 6.42 (m, 2H), 6.31 (m, 2H), 6.22 (d, J=8.57 Hz, 1H), 5.13 (s, 1H), 1.88 (br s, 1H), 1.62 (d, J=7.07 Hz, 3H). Mass spectrum (LCMS, ESI pos.): Calcd for $C_{23}H_{17}Cl_2IN_2O_3$: 565.9; found 566.4 (M+H).

Example 66

4-[1-(2-Amino-4-chloro-phenyl)-ethyl]-3-(4-chloro-phenyl)-7-iodo-1-[3-(4-methyl-piperazin-1-yl)-propyl]-3,4-dihydro-1H-benzo[e][1,4]diazepine-2,5-dione

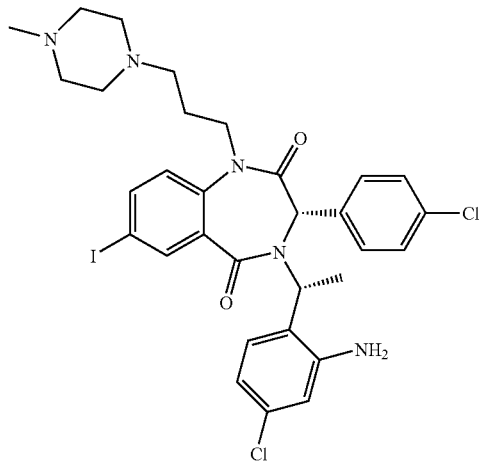

¹H NMR (400 MHz, CD₃OD) δ 7.91 (s, 1H), 7.72 (m, 1H), 7.67 (d, 1H, J=6.4 Hz), 7.51 (m, 1H), 7.34 (m, 1H), 6.98 (m, 3H), 6.45 (m, 2H), 6.23 (q, 1H, J=6.4 Hz), 5.98 (m, 1H), 4.28 (m, 1H), 4.05–3.56 (bm, 10H), 3.40 (bs, 1H), 3.05 (s, 3H), 2.36–2.18 (bm, 2H), 1.89 (d, J=6.8 Hz). Mass spectrum (LCMS, ESI pos.): Calcd for $C_{31}H_{34}Cl_2IN_5O_2$: 705.1; found 705.9 (M+H).

Example 67

4-(2-Amino-4-chloro-benzyl)-3-(4-chloro-phenyl)-1-(4-dimethylamino-butyl)-7-iodo-3,4-dihydro-1H-benzo[e][1,4]diazepine-2,5-dione

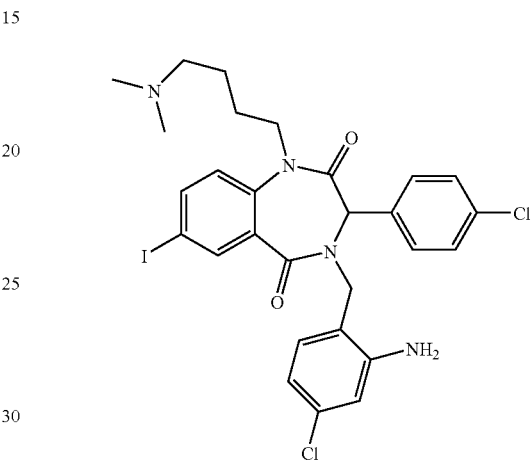

¹H NMR (400 MHz, CD₃OD) δ 7.85 (d, 1H, J=2.0 Hz), 7.48 (dd, 1H, J=2.0, 8.8 Hz), 7.21 (d, 1H, J=8.4 Hz), 7.04 (d, 2H, J=8.4 Hz), 6.94 (d, 1H, J=8.8 Hz), 6.81 (m, 3H), 6.62 (dd, 1H, J=2.0, 8.8 Hz), 5.53 (s, 1H), 5.23 (d, 1H, J=14.4 Hz), 4.63 (d, 1H, J=14.4 Hz), 4.40 (m, 1H), 3.77 (m, 1H), 3.07 (m, 2H), 2.85 (d, 6H, J=5.2 Hz), 1.71–1.52 (m, 4H). Mass spectrum (LCMS, ESI pos.): Calcd for $C_{28}H_{29}Cl_2IN_4O_2$: 650.07; found 651.0 (M+H).

Example 68

4-(2-Amino-4-chloro-benzyl)-3-(4-chloro-phenyl)-7-iodo-1-(4-morpholin-4-yl-butyl)-3,4-dihydro-1H-benzo[e][1,4]diazepien-2,5-dione

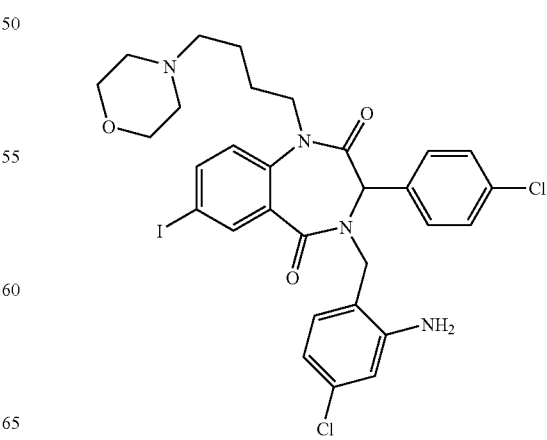

$^1$H NMR (400 MHz, CD$_3$OD) δ 7.86 (d, 1H, J=2.0 Hz), 7.65 (dd, 1H, J=2.0, 8.8 Hz), 7.21 (d, 1H, J=8.4 Hz), 7.04 (d, 2H, J=8.8 Hz), 6.94 (d, H, J=8.8 Hz), 6.80 (m, 3H), 6.60 (dd, 1H, J=2.0, 8.8 Hz), 5.54 (s, 1H), 5.25 (d, 1H, J=14.4 Hz), 4.62 (d, 1H, J=14.4 Hz), 4.40 (m, 1H), 4.09 (m, 2H), 3.75 (m, 3H), 3.41 (m, 2H), 3.09 (m, 4H), 1.60 (m, 4H). Mass spectrum (LCMS, ESI pos.): Calcd for C$_{30}$H$_{31}$Cl$_2$IN$_4$O$_3$: 692.08; found 693.0 (M+H).

Example 69

4-(2-Amino-4-chloro-benzyl)-3-(4-chloro-phenyl)-7-iodo-1-[4-(4-methyl-piperazin-1-yl)-butyl]-3,4-dihydro-1H-benzo[e][1,4]diazepine-2,5-dione

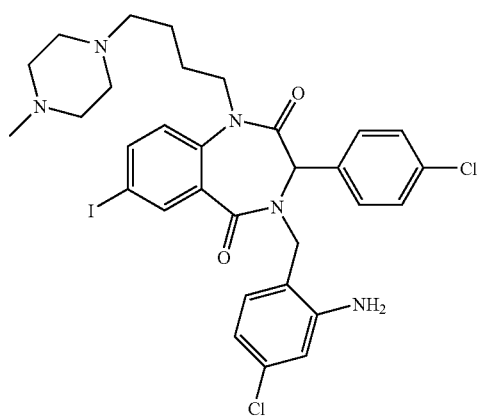

$^1$H NMR (400 MHz, CD$_3$OD) δ 7.84 (d, 1H, J=2.4 Hz), 7.64 (dd, 1H, J=2.0, 8.4 Hz), 7.21 (d, 1H, J=8.0 Hz), 7.04 (d, 2H, J=8.4 Hz), 6.94 (d, H, J=8.8 Hz), 6.80 (m, 3H), 6.63 (dd, 1H, J=2.4, 8.4 Hz), 5.53 (s, 1H), 5.27 (d, 1H, J=14.4 Hz), 4.61 (d, 1H, J=14.4 Hz), 4.39 (m, 1H), 3.78 (m, 1H), 3.40 (m, 4H), 3.20 (m, 4H), 2.91 (s, 3H), 2.88 (m, 2H), 1.70–1.52 (m, 4H). Mass spectrum (LCMS, ESI pos.): Calcd for C$_{31}$H$_{34}$Cl$_2$IN$_5$O$_2$: 705.1; found 706.2 (M+H).

Example 70

4-(2-Amino-4-chloro-benzyl)-3-(4-chloro-phenyl)-1-(3-dimethylamino-propyl)-7-iodo-3,4-dihydro-1H-benzo[e][1,4]diazepine-2,5-dione

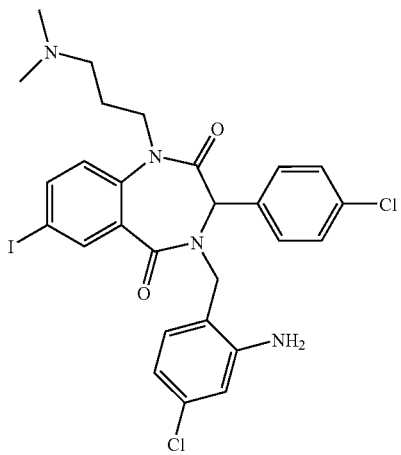

$^1$H NMR (400 MHz, CD$_3$OD) δ 7.88 (d, 1H, J=2.4 Hz), 7.67 (dd, 1H, J=2.0, 8.4 Hz), 7.23 (d, 1H, J=8.0 Hz), 7.07 (d, 2H, J=8.4 Hz), 6.93 (d, 1H, J=8.8 Hz), 6.85 (d, 2H, J=8.8 Hz), 6.78 (d, 1H, J=2.0 Hz), 6.62 (dd, 1H, J=2.4, 8.0 Hz), 5.57 (s, 1H), 5.06 (d, J=14.4 Hz), 4.85 (d, 1H, J=14.4 Hz), 4.36 (m, 1H), 3.83 (m, 1H), 3.04 (m, 2H), 2.85 (d, 6H, J=3.2 Hz), 2.04–1.90 (m, 2H). Mass spectrum (LCMS ESI pos.): Calcd for C$_{27}$H$_{27}$Cl$_2$IN$_4$O$_2$: 636.06; found 636.9 (M+H).

Example 71

4-(2-Amino-4-chloro-benzyl)-3-(4-chloro-phenyl)-7-iodo-1-(3-morpholin-4-yl-propyl)-3,4-dihydro-1H-benzo[e][1,4]diazepine-2,5-dione

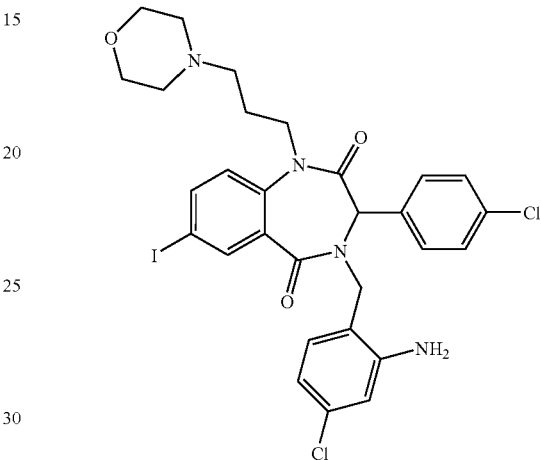

$^1$H NMR (400 MHz, CD$_3$OD) δ 7.88 (d, 1H, J=2.4 Hz), 7.66 (dd, 1H, J=2.0, 8.4 Hz), 7.24 (d, 1H, J=8.0 Hz), 7.08 (d, 23H, J=2.4 Hz), 6.95 (d, 1H, J=8.8 Hz), 6.86 (d, 2H, J=8.4 Hz), 6.79 (d, 1H, J=2.0 Hz), 6.63 (dd, 1H, J=2.4, 8.4 Hz), 5.58 (s, 1H), 5.04 (d, 1H, J=14.8 Hz), 4.84 (d, 1H, J=14.8 Hz), 4.39 (m, 1H), 4.09 (m, 2H), 3.82 (m, 1H), 3.74 (m, 2H), 3.42 (m, 2H), 3.08 (m, 4H), 2.04–1.95 (m, 2H). Mass spectrum (LCMS, ESI pos.): Calcd for C$_{29}$H$_{29}$Cl$_2$IN$_4$O$_3$: 678.07; found 679.0 (M+H).

Example 72

4-(4-Chloro-2-hydroxybenzyl)-3-(4-chlorophenyl)-7-iodo-1-[2-(2-methoxy-ethoxy)ethyl]-3,4-dihydro-1H-benzo[e][1,4]diazepine-2,5-dione

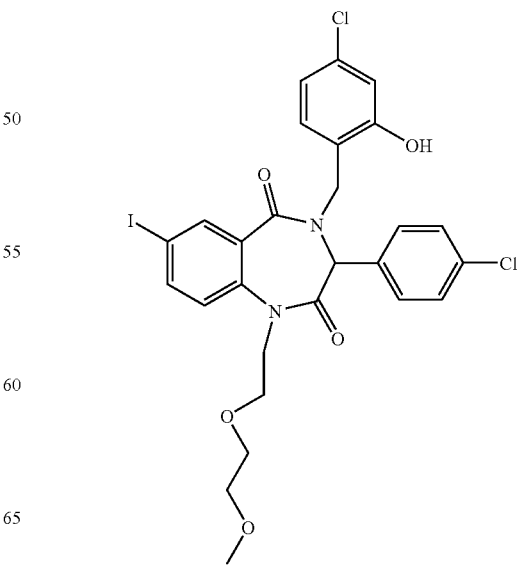

¹H NMR (400 MHz, CDCl₃) δ 7.95 (d, J=2.1 Hz, 1H), 7.56 (dd, J=2.2 Hz, 8.6 Hz, 1H), 7.13 (t, J=8.0 Hz, 2H), 7.07 (d, J=2.1 Hz, 1H), 6.98 (d, J=8.6 Hz, 2H), 6.82 (dd, J=2.1 Hz, 7.9 Hz, 1H), 6.59 (dd, J=1.0 Hz, 8.8 Hz, 2H), 5.51 (s, 1H), 5.41 (d, J=15.0 Hz, 1H), 5.33 (s, 1H), 4.41 (d, 15.0 Hz, 1H), 4.05–4.11 (m, 2H), 3.92–3.99 (m, 1H), 3.76–3.69 (m, 1H), 3.64–3.56 (m, 2H), 3.54–3.48 (m, 2H), 3.37 (s, 3H). Mass spectrum (LCMS, ESI pos.): Calcd for C₂₇H₂₅Cl₂IN₂O₅: 654.02; found 654.8 (M+H).

Example 73

4-[(S)-1-(2-Amino-4-chlorophenyl)ethyl]-(3R)-3-(4-chlorophenyl)-7-iodo-1-(2-morpholin-4-ylethyl)-3,4-dihydro-1H-benzo[e][1,4]diazepine-2,5-dione

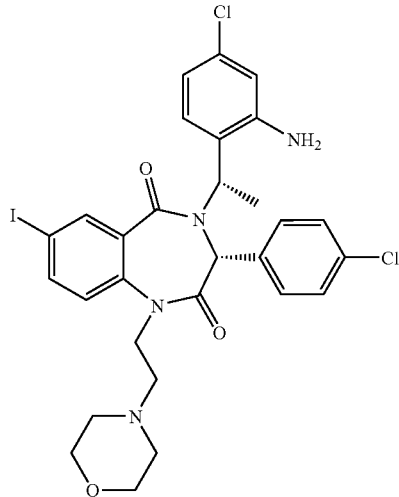

¹H NMR (400 MHz, CDCl₃) δ 7.86 (d, J=2.1 Hz, 1H), 7.58 (dd, J=2.1 Hz, 8.5 Hz, 1H), 7.28 (d, J=8.1 Hz, 1H), 6.92 (m, 3H), 6.76 (m, 3H), 6.57 (dd, J=2.1 Hz, 8.4 Hz, 1H), 6.27 (q, J=7.3 Hz, 1H), 5.31 (s, 1H), 4.63–4.55 (m, 1H), 3.82–3.73 (m, 1H), 3.60–3.54 (m, 2H), 3.53–3.45 (m, 2H), 2.69–2.61 (m, 1H), 2.46–2.34 (m, 3H), 2.27–2.19 (m, 2H), 1.75 (s, 3H). Mass spectrum (LCMS, ESI pos.): Calcd for C₂₉H₂₉Cl₂IN₄O₃: 678.07; found 678.9 (M+H).

Example 74

4-(2-Amino-4-chlorobenzyl)-3-(4-chlorophenyl)-7-iodo-1-[3-(4methyl-piperazin-1-yl)propyl]-3,4-dihydro-1H-benzo[e][1,4]diazepine-2,5-dione

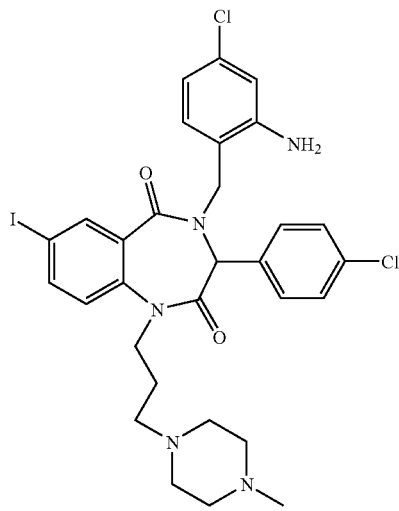

¹H NMR (400 MHz, CD₃OD) δ 7.83 (d, J=2.1 Hz, 1H), 7.63 (dd, J=2.1 Hz, 8.6 Hz, 1H), 7.20 (d, J=7.9 Hz, 1H), 7.07–7.02 (m, 2H), 6.95 (d, J=8.8 Hz, 1H), 6.85–6.80 (m, 2H), 6.77 (d, J=2.1 Hz, 1H), 6.57 (dd, J=2.1 Hz, 7.9 Hz 1H), 5.50 (s, 1H), 5.13 (d, J=14.4 Hz, 1H), 4.73 (d, J=14.6 Hz 1H), 4.44–4.32 (m, 1H), 3.81–3.70 (m, 1H), 3.37 (s, 2H), 2.10–2.72 (m, 11H), 1.63–1.85 (m, 2H). Mass spectrum (LCMS, ESI pos.): Calcd for C₃₀H₃₂Cl2IN₅O₂: 691.1; found 692.0 (M+H).

Example 75

5-(2-Allyloxy-4-chlorobenzyloxy)-3-(4-chlorophenyl)-7-iodo-1-[2-(2-methoxyethoxy)ethyl]-1,3-dihydrobenzo[e][1,4]diazepin-2-one

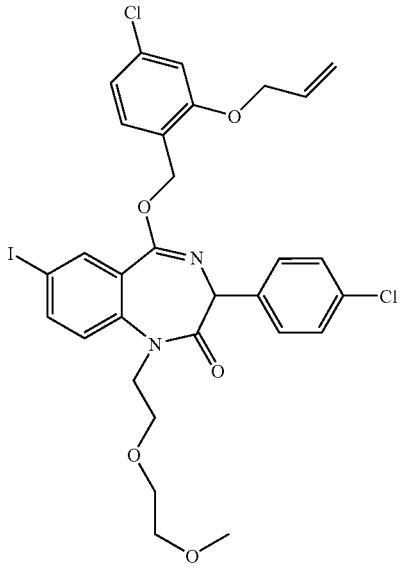

¹H NMR (400 MHz, CDCl₃) δ 8.01 (d, J=2.1 Hz, 1H), 7.86 (dd, J=2.1 Hz, 8.5 Hz, 1H), 7.58–7.47 (m, 3H), 7.42–7.330 (m, 3H), 6.96 (dd, J=1.9 Hz, 8.1 Hz, 1H), 6.92 (d, J=1.9 Hz, 1H), 6.13–6.02 (m, 1H), 5.51–5.31 (m, 4H), 4.67 (s, 1H), 4.63 (m, 2H), 4.12–4.02 (m, 1H), 3.97–3.89 (m, 1H), 3.87–3.79 (m, 1H), 3.66–3.59 (m, 1H), 3.58–3.54 (m, 2H), 3.51–3.45 (m, 2H), 3.36 (s, 3H). Mass spectrum (LCMS, ESI pos.): Calcd for C₃₀H₂₉Cl₂IN₂O₅: 694.05; found 694.9 (M+H).

Example 76

4-(2-Amino-4-chlorobenzyl)-3-(4-chlorophenyl)-7-iodo-3,4-dihydro-1H-benzo[e][1,4]diazepine-2,5-dione

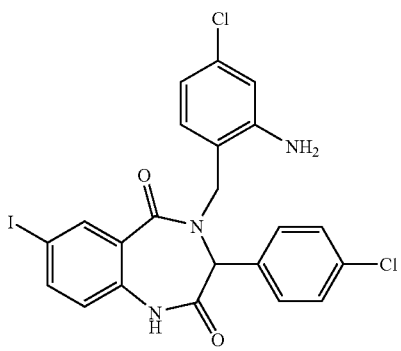

¹H NMR (400 MHz, CDCl₃) δ 8.74 (s, 1H), 8.04 (s, 1H), 7.56 (dd, J=1.9 Hz, 8.3 Hz, 1H), 7.12–7.69 (m, 3H), 6.91–6.81 (m, 2H), 6.71 (d, J=1.9 Hz, 1H), (dd, J=1.9 Hz, 7.9 Hz, 1H), 6.52 (d, J=8.3 Hz, 1H), 5.5 (d, J=14.5 Hz, 1H), 4.93 (s, 2H), 4.34 (d, J=15.0 Hz, 1H).

Example 77

4-[1-(3-Amino-4-chlorophenyl)ethyl]-3-(4-chlorophenyl)-7-iodo-3,4-dihydro-1H-benzo[e][1,4]diazepine-2,5-dione

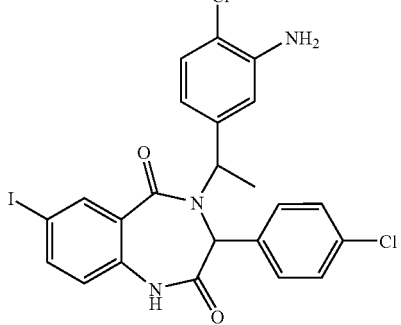

¹H NMR (400 MHz, CD₃OD) δ 8.06 (d, J=2.1 Hz, 1H), 7.85 (s, 1H), 7.49 (dd, J=2.1 Hz, 8.3 Hz, 1H), 7.22 (d, J=8.1 Hz, 1H), 7.02 (s, 1H), 6.97 (d, J=8.5 Hz, 2H), 6.91 (dd, J=1.9 Hz, 8.3 Hz, 1H), 6.66 (m, 2H), 6.43 (d, J=8.3 Hz, 1H), 6.40–6.36 (m, 1H), 5.31 (s, 1H), 1.7 (d, J=7.3 Hz, 3H). Mass spectrum (LCMS, ESI pos.): Calcd for $C_{23}H_{18}Cl_2IN_3O_2$: 564.98; found 565.5 (M+H).

Example 78

4-Benzyl-7-bromo-3-(4-chlorophenyl)-1-methyl-1,4-benzodiazepine-2,5-dione

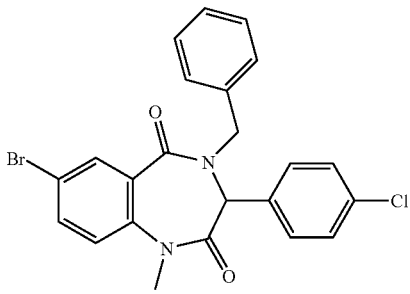

¹H NMR (400 MHz, CDCl₃) δ 3.43 (s, 3H), 4.65 (d, J=14.4 Hz, 1H), 5.38 (d, J=14.4 Hz, 1H), 5.47 (s, 1H), 6.60 (dd, J=8.4 Hz, 1.2 Hz, 2H), 6.75 (d, J=8.8 Hz, 1H), 6.96 (d, J=8.8 Hz, 2H), 7.28–7.41 (m, 4H), 7.48–7.51 (m, 2H), 7.80 (d, J=2.4 Hz, 1H). Mass spectrum (LCMS, ESI pos.): Calcd for $C_{23}H_{18}BrClN_2O_2$: 468; found: 469 (M+H)⁺.

Example 79

7-Bromo-3-(4-chlorophenyl)-1-methyl-4-(1-phenethyl)-1,4-benzodiazepine-2,5-dione

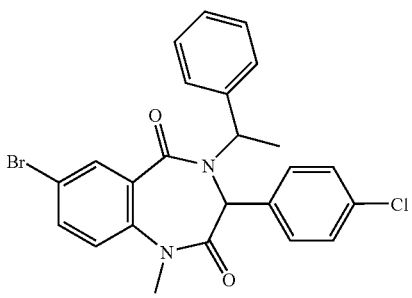

Mass spectrum (LCMS, ESI pos.): Calcd for $C_{24}H_{20}BrClN_2O_2$: 482; found: 483 (M+H)⁺.

Example 80

1,3-Dihydro-4-[1-(2-amino-4-chlorophenyl)ethyl]-3-(4-chlorophenyl)-7-iodo-1,4-benzodiazepine-2,5-dione

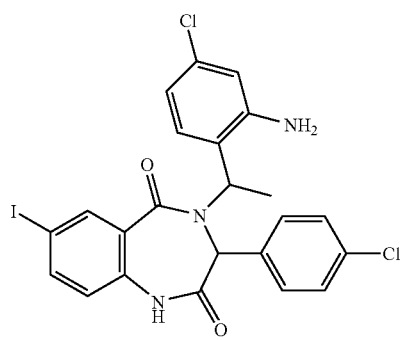

¹H NMR (400 MHz, DMSO-d₆) δ 1.61 (d, J=6.8 Hz, 3H), 5.00 (s, 1H), 5.78 (s, 2H), 6.09 (q, J=6.8 Hz, 1H), 6.51–6.54 (m, 1H), 6.67 (d, J=8.4 Hz, 1H), 6.77–6.81 (m, 3H), 7.08 (d, J=8.8 Hz, 2H), 7.26 (d, J=8.0 Hz, 1H), 7.59 (dd, J=8.8 Hz, J=2.0 Hz, 1H), 7.79 (d, J=1.6 Hz, 1H), 10.98 (br s, 1H). Mass spectrum (LCMS, ESI pos.): Calcd for $C_{23}H_{18}Cl_2IN_3O_2$: 565; found: 566 (M+H)⁺.

Example 81 b 3-(4-Chlorophenyl)-4-[1-(4-chloro-2-nitrophenyl)ethyl]-7-iodo-1-[2-(4-morpholino)ethyl]-1,4-enzodiazepine-2,5-dione

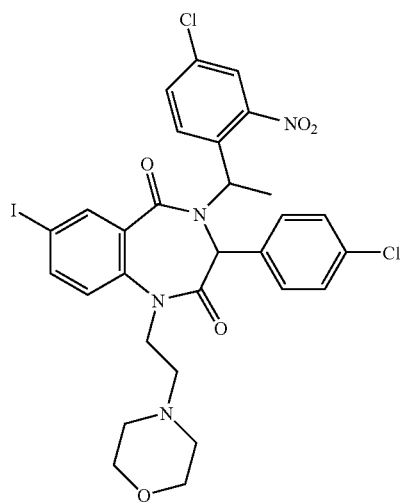

¹H NMR (400 MHz, CDCl₃) δ 1.81 (d, J=6.8 Hz, 3H), 2.23–2.28 (m, 2H), 2.37–2.46 (m, 3H), 2.59–2.66 (m, 1H), 3.54–3.63 (m, 5H), 4.44–4.51 (m, 1H), 5.42 (s, 1H), 6.57–6.70 (m, 4H), 6.94 (d, J=8.4 Hz, 2H), 7.44 (dd, J=8.8 Hz, 2.0 Hz, 1H), 7.55 (dd, J=8.4 Hz, 2.0 Hz, 1H), 7.63 (d, J=8.0 Hz, 1H), 7.86 (d, J=2.0 Hz, 1H), 7.96 (d, J=2.0 Hz, 1H). Mass spectrum (LCMS, ESI pos.): Calcd for C₂₉H₂₇Cl₂IN₄O₅: 708; found: 709 (M+H)⁺.

Example 82

5-[(3S)-3-(4-Chlorophenyl)-4-[(R)-1-(4-chlorophenyl)ethyl]-2,5-dioxo-7-(propyn-1-yl)-1,4-benzodiazepin-1-yl]valeric acid sodium salt

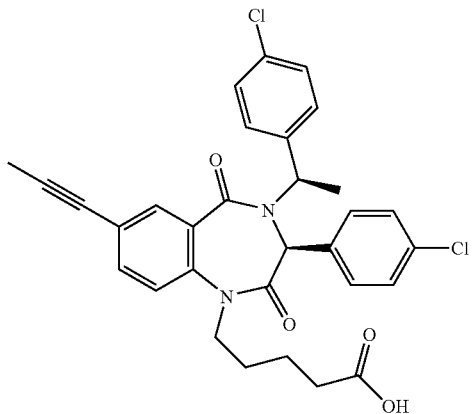

a) (3S)-3-(4-Chlorophenyl)-4-[(R)-1-(4-chlorophenyl)ethyl]-7-(propyn-1-yl)-1,4-benzodiazepine-2,5-dione Propyne (2 mL) was condensed in a sealed tube at −78° C. Then, (3S)-3-(4-Chlorophenyl)-4-[(R)-1-(4-chlorophenyl)ethyl]-7-iodo-1,4-benzodiazepine-2,5-dione (200 mg, 0.362 mmol), copper iodide (15 mg, 0.0788 mmol), dichlorobis(triphenylphosphine)palladium (II) (39 mg, 0.0556 mmol), triethylamine (2 mL), and acetonitrile (4 mL) were added. The sealed tube was closed and the reaction mixture was allowed warm up to room temperature. After 12 h, the reaction mixture was cooled to −78° C. and the sealed tube was opened and allowed to warm up to room temperature under vigorous stirring. Then, solvents were evaporated in vacuo and the residue was purified by column chromatgraphy on silica (EtOAc/Hexanes, 1:1) to give the title compound as colorless solid (150 mg, 89%): ¹H NMR (400 MHz, CDCl₃) δ 1.73 (d, J=7.1 Hz, 3H), 2.06 (s, 3H), 5.24 (s, 1H), 6.49 (q, J=7.1 Hz, 1H), 6.62–6.65 (m, 3H), 6.93 (d, J=8.4 Hz, 2H), 7.20 (dd, J=8.0 Hz, J=2.0 Hz, 1H), 7.33 (d, J=8.4 Hz, 2H), 7.53 (d, J=8.8 Hz, 2H), 7.79 (d, J=2.0 Hz, 1H), 8.57 (br s, 1H). Mass spectrum (LCMS, ESI pos.): Calcd for C₂₆H₂₀Cl₂N₂O₂: 463; found: 464 (M+H)⁺.

b) 5-[(3S)-3-(4-Chlorophenyl)-4-[(R)-1-(4-chlorophenyl)ethyl]-2,5-dioxo-7-(propyn-1-yl)-2,4-benzodiazepin-1-yl]valeric acid sodium salt The title compound was prepared (58%) from (3S)-3-(4-chlorophenyl)-4-[(R)-1-(4-chlorophenyl)ethyl]-7-(propyn-1-yl)-1,4-benzodiazepine-2,5-dione following successively the general procedure for the alkylation of diazepines at position 1, followed by example 1, step b. ¹H NMR (400 MHz, CDCl₃) δ 1.60–1.74 (m, 7H), 2.02 (s, 3H), 2.37 (t, J=6.8 Hz, 2H), 3.64–3.71 (m, 1H), 4.27–4.34 (m, 1H), 5.31 (s, 1H), 6.42 (q, J=6.8 Hz, 1H), 6.46–6.49 (m, 2H), 6.76 (d, J=8.4 Hz, 1H), 6.87 (d, J=8.4 Hz, 2H), 7.16 (dd, J=8.4 Hz, 2.0 Hz, 1H), 7.29 (d, J=8.4 Hz, 2H), 7.48 (d, J=8.8 Hz, 2H), 7.67 (d, J=2.0 Hz, 1H), 7.90 (br s, 1H). Mass spectrum (LCMS, ESI pos.): Calcd for C₃₁H₂₈Cl₂N₂O₄: 562; found: 563 (M+H)⁺.

Example 83

4-[1-(2-Amino-4-chlorophenyl)ethyl]-3-(4-chlorophenyl)-7-iodo-1-[2-(2-methoxyethoxy)ethyl]-1,4-benzodiazepine-2,5-dione

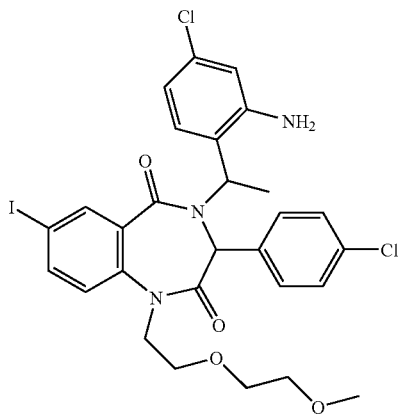

¹H NMR (400 MHz, CDCl₃) δ 1.75 (d, J=6.8 Hz, 3H), 3.36 (s, 3H), 3.54–3.64 (m, 4H), 3.71–3.76 (m, 1H), 3.85–3.90 (m, 1H), 3.97–4.03 (m, 1H), 4.17–4.24 (m, 1H), 4.77 (br s, 2H), 5.27 (s, 1H), 6.27 (q, J=6.8 Hz, 1H), 6.62 (dd, J=8.4 Hz, 2.4 Hz, 1H), 6.66–6.70 (m, 3H), 6.90 (d, J=8.4 Hz, 2H), 6.97 (d, J=8.8 Hz, 1H), 7.21 (d, J=8.4 Hz, 1H), 7.48 (dd, J=8.4 Hz, 2.0 Hz, 1H), 7.90 (d, J=2.0 Hz, 1H). Mass spectrum (LCMS, ESI pos.): Calcd for C₂₈H₂₈Cl₂IN₃O₄: 667; found: 668 (M+H)⁺.

Example 84

4-[(R)-1-(2-amino-4-chlorophenyl)ethyl]-(3S)-3-(4-chlorophenyl)-7-iodo-1-[2-(2-methoxyethoxy)ethyl]-1,4-benzodiazepine-2,5-dione

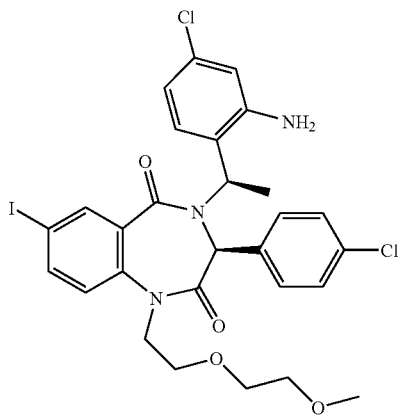

Mass spectrum (LCMS, ESI pos.): Calcd for C$_{28}$H$_{28}$Cl$_2$IN$_3$O$_4$: 667; found: 668 (M+H)$^+$.

Example 85

(3R)-4-[(S)-1-(2-amino-4-chlorophenyl)ethyl]-3-(4-chlorophenyl)-7-iodo-1-[2-(2-methoxyethoxy)ethyl]-1,4-benzodiazepine-2,5-dione

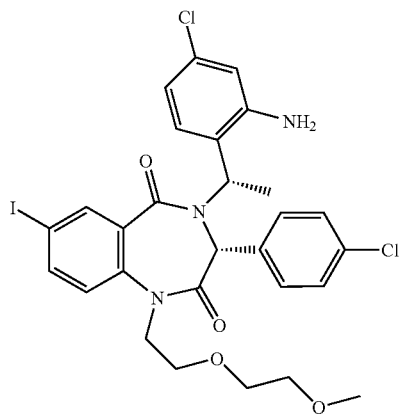

Mass spectrum (LCMS, ESI pos.): Calcd for C$_{28}$H$_{28}$Cl$_2$IN$_3$O$_4$: 667; found: 668 (M+H)$^+$.

Example 86

4-[1-(2-Amino-4-chlorophenyl)ethyl]-3-(4-chlorophenyl)-7-iodo-1-[2-(4-morpholino)ethyl]-1,4-benzodiazepine-2,5-dione

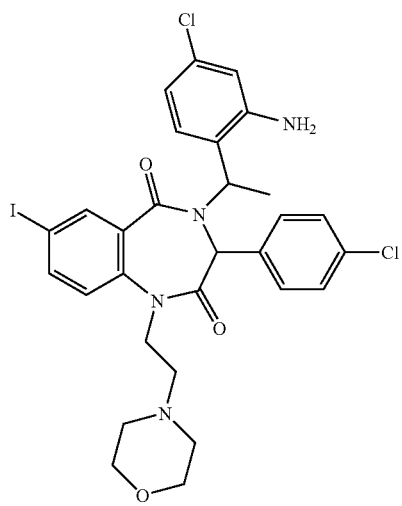

$^1$H NMR (400 MHz, CDCl$_3$) δ 1.76 (d, J=7.1 Hz, 3H), 2.26–2.31 (m, 2H), 2.42–2.50 (m, 3H), 2.60–2.66 (m, 1H), 3.53–3.70 (m, 5H), 4.48–4.55 (m, 1H), 4.74 (br s, 2H), 5.28 (s, 1H), 6.28 (q, J=7.1 Hz, 1H), 6.60 (dd, J=8.8 Hz, 2.4 Hz, 1H), 6.66–6.69 (m, 3H), 6.89 (d, J=8.4 Hz, 2H), 7.21–7.19 (d, J=8.4 Hz, 1H), 7.48 (dd, J=8.4 Hz, 2.0 Hz), 7.93 (d, J=2.0 Hz, 1H). Mass spectrum (LCMS, ESI pos.): Calcd for C$_{29}$H$_{29}$Cl$_2$IN$_4$O$_3$: 678; found: 679 (M+H)$^+$.

Example 87

(3S)-4-[(R)-1-(2-Amino-4-chlorophenyl)ethyl]-3-(4-chlorophenyl)-7-iodo-1-[2-(4-morpholino)ethyl]-1,4-benzodiazepine-2,5-dione

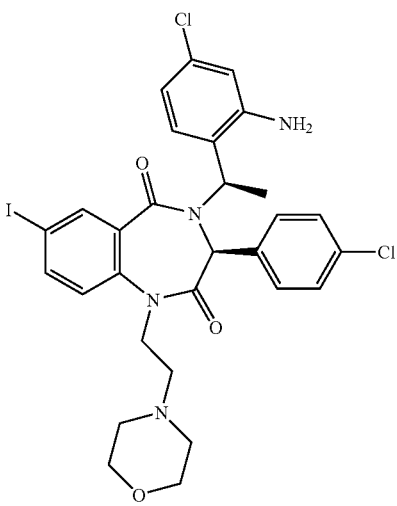

Mass spectrum (LCMS, ESI pos.): Calcd for C$_{29}$H$_{29}$Cl$_2$IN$_4$O$_3$: 678; found: 679 (M+H)$^+$.

Example 88

(3R)-4-[(S)-1-(2-amino-4-chlorophenyl)ethyl]-3-(4-chlorophenyl)-7-iodo-1-[2-(4-morpholino)ethyl]-1,4-benzodiazepine-2,5-dione

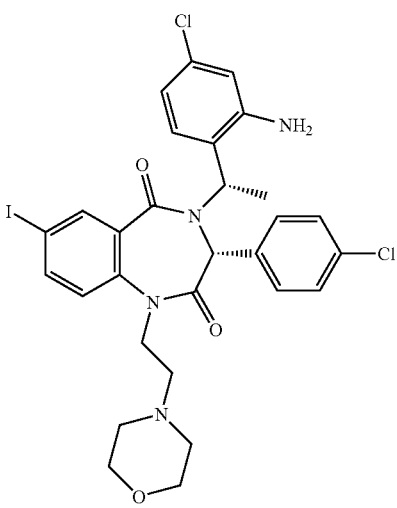

Mass spectrum (LMCS, ESI pos,): Calcd for C$_{29}$H$_{29}$Cl$_2$IN$_4$O$_3$: 678; found: 679 (M+H)$^+$.

Example 89

3-(4-Chlorophenyl)-4-[1-(2,6-dichloro-3-pyridyl)ethyl]-7-iodo-1,4-benzodiazepine-2,5-dione

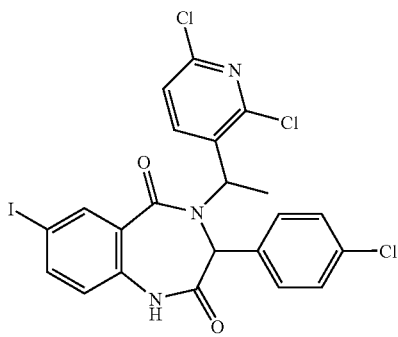

$^1$H NMR (400 MHz, DMSO-d$_6$) δ 1.69 (d, J=6.8 Hz, 3H), 5.28 (s, 1H), 6.09 (q, J=6.8 Hz, 1H), 6.59 (d, J=8.4 Hz, 1H), 6.87 (d, J=8.4 Hz, 2H), 7.20 (d, J=8.8 Hz, 2H), 7.55–7.59 (m, 2H), 7.78 (d, J=2.0 Hz, 1H), 8.21 (d, J=8.0 Hz, 1H), 10.9 (s, 1H). Mass spectrum (LCMS, ESI pos.): Calcd for C$_{22}$H$_{15}$Cl$_3$IN$_3$O$_3$: 585; found 586 (M+H)$^+$.

Example 90

1,3-Dihydro-4-[1-(2-amino-4-chlorophenyl)ethyl]-3-(4-chlorophenyl)-7-iodo-1-methyl-1,4-benzodiazepine-2,5-dione

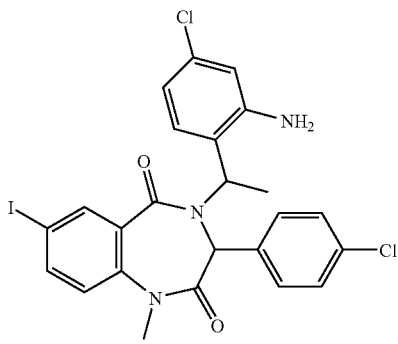

$^1$H NMR (400 MHz, CDCl$_3$) δ 1.75 (d, J=6.8 Hz, 3H), 3.46 (s, 3H), 5.34 (s, 1H), 5.95 (q, J=6.8 Hz, 1H), 6.55 (d, J=8.4 Hz, 2H), 6.61 (d, J=8.8 Hz, 1H), 6.88–6.91 (m, 3H), 7.30–7.32 (m, 2H), 7.53 (dd, J=8.8 Hz, 2.0 Hz, 1H), 7.97 (d, J=2.0 Hz, 1H). Mass spectrum (LCMS, ESI pos.): Calcd for C$_{24}$H$_{20}$Cl$_2$IN$_3$O$_2$: 579; found: 580 (M+H)$^+$.

Example 91

1,3-Dihydro-4-[1-(2-acetylamino-4-chlorophenyl)ethyl]-3-(4-chlorophenyl)-7-iodo-1,4-benzodiazepine-2,5-dione

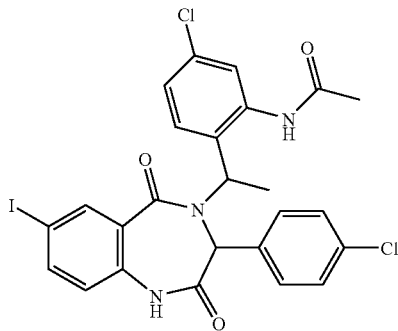

Acetyl chloride (15 μL, 0.212 mmol) was added at 0° C. under argon to a solution of 1,3-dihydro-4-[1-(2-amino-4-chlorophenyl)ethyl]-3-(4-chloropenyl)-7-iodo-1,4-benzodiazepine-2,5-dione (100 mg, 0.177 mmol), in tetrahydrofuran (5 mL) and chloroform (5 mL). Then, triethylamine (30 μL, 0.21 mmol) was added drop wise and the reaction mixture was allowed warm up to room temperature. After 30 minutes, the solution was concentrated under reduced pressure and the residue was petitioned between ethylacetate and 1N sodium bicarbonate. Organic layer was dried (Na$_2$SO$_4$), evaporated, and the residue was purified by column chromatography to give the title compound (49 mg, 45%) as a colorless powder: $^1$H NMR (400 MHz, CDCl$_3$) δ 1.81 (d, J=6.8 Hz, 3H), 2.44 (s, 3H), 5.33 (s, 1H), 6.37 (q, J=6.8 Hz, 1H), 6.47 (d, J=8.4 Hz, 2H), 6.55 (d, J=8.4 Hz, 1H), 6.98 (d, J=8.4 Hz, 2H), 7.03 (dd, J=8.4 Hz, 2.0 Hz, 1H), 7.36 (d, J=8.4 Hz, 1H), 7.59 (dd, J=8.4 Hz, 2.0 Hz, 1H), 7.98 (d, J=2.0 Hz, 1H), 8.28 (br s, 1H), 8.54 (d, J=2.0 Hz, 1H), 9.94 (s, 1H). Mass spectrum (LCMS, ESI pos.): Calcd for C$_{25}$H$_{20}$Cl$_2$IN$_3$O$_3$: 607; found: 608 (M+H)$^+$.

Example 92

1,3-Dihydro-4-[1-(2-azido-3-pyridyl)ethyl]-3-(4-chlorophenyl)-7-iodo-1,4-benzodiazepine-2,5-dione

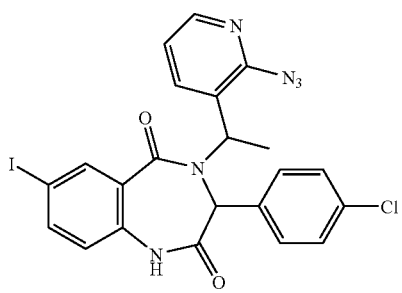

$^1$H NMR (400 MHz, CD$_3$OD) δ 1.94 (d, J=6.8 Hz, 3H), 5.06 (s, 1H), 6.50 (d, J=8.4 Hz, 1H), 6.85 (q, J=6.8 Hz, 1H), 7.01–7.04 (m, 2H), 7.19 (d, J=8.8 Hz, 2H), 7.45 (t, J=7.0 Hz, 1H), 7.56 (dd, J=8.8 Hz, 2.0 Hz, 1H), 7.94 (d, J=7.2 Hz, 1H), 8.06 (d, J=2.4 Hz, 1H), 9.12 (d, J=6.8 Hz, 1H). Mass spectrum (LCMS, ESI pos.): Calcd for C$_{22}$H$_{16}$ClIN$_6$O$_2$: 559; found: 560 (M+H)$^+$.

Example 93

4-[1-(2-Amino-4-chlorophenyl)ethyl]-3-(4-chlorophenyl)-1-[2-(2-methoxyethoxy)ethyl]-7-(propyn-1-yl)-1,4-benzodiazepine-2,5-dione hydrochloride

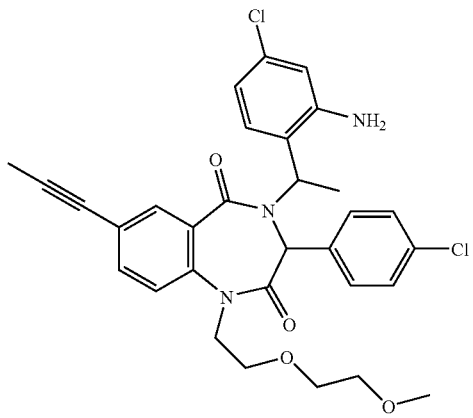

$^1$H NMR (400 MHz, DMSO-d$_6$) δ 1.61 (d, J=6.8 Hz, 3H), 2.00 (s, 3H), 3.17 (s, 3H), 3.30–3.65 (m, 6H), 3.85–3.92 (m, 1H), 4.33–4.39 (m, 1H), 5.13 (s, 1H), 6.08 (q, J=6.8 Hz, 1H), 6.52 (dd, J=8.4 Hz, 2.0 Hz, 1H), 6.69 (d, J=7.6 Hz, 2H), 6.78 (d, J=2.0 Hz, 1H), 6.98 (d, J=8.4 Hz, 2H), 7.20–7.28 (m, 3H), 7.40 (d, J=2.0 Hz, 1H). Mass spectrum (LCMS, ESI pos.): Calcd for C$_{31}$H$_{31}$Cl$_2$N$_3$O$_4$: 579; found: 580 (M+H)$^+$.

Example 94

(3S)-4-[(R)-1-(2-Amino-4-chlorophenyl)ethyl]-3-(4-chlorophenyl)-1-[2-(2-methoxyethoxy)ethyl]-7-(propyn-1-yl)-1,4-benzodiazepine-2,5-dione hydrochloride

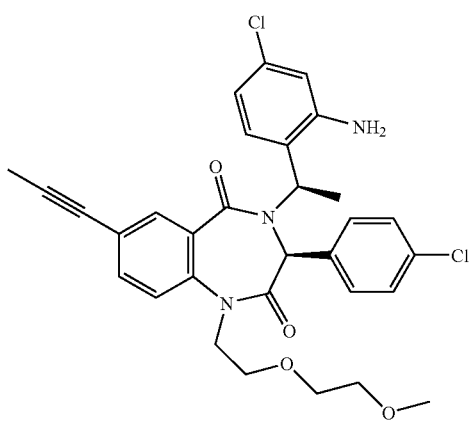

Mass spectrum (LCMS, ESI pos.): Calcd for C$_{31}$H$_{31}$Cl$_2$N$_3$O$_4$: 579; found: 580 (M+H)$^+$.

Example 95

4-[1-Amino-4-chlorophnyl)ethyl]-3-(4-chlorophenyl)-1-[2-(4-morpholino)ehtyl]-7-(propyn-1-yl)-1,4-benzodiazepine-2,5-dione hydrochloride

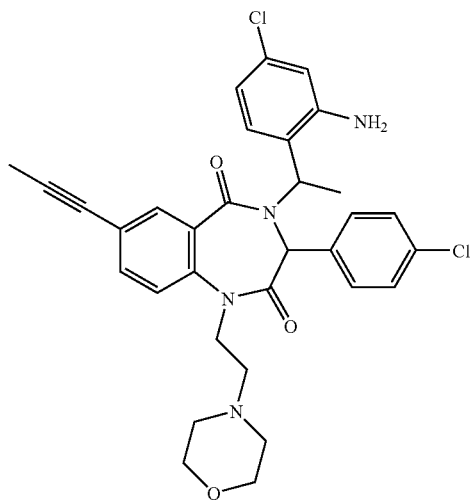

$^1$H NMR (400 MHz, CDCl$_3$) δ 1.76 (d, J=6.8 Hz, 3H), 2.02 (s, 3H)), 2.22–2.49 (m, 5H), 2.61–2.67 (m, 1H), 3.53–3.71 (m, 5H), 4.49–4.56 (m, 1H), 4.76 (s, 2H), 5.27 (m, 3H ), 6.30 (q, J=6.8 Hz, 1H), 6.60 (dd, J=8.4 Hz, 2.0 Hz, 1H), 6.66–6.68 (m, 3H), 6.83 (d, J=8.8 Hz, 1H), 6.87 (d, J=8.4 Hz, 2H), 7,16–7.21 (m, 2H), 7.66 (d, J=2.0 Hz, 1H). Mass spectrum (LCMS, ESI pos.): Calcd for C$_{32}$H$_{32}$Cl$_2$N$_4$O$_3$: 590; found 591 (M+H)$^+$.

Example 96

(3S)-4-[(R)-1-(2-Amino-4-chlorophenyl)-ethyl]-3-(4-chlorophenyl)-1-[2-(4-morpholino)ethyl]-7-(propyn-1-yl)-1,4-benzodiazepine-2,5-one hydrochloride

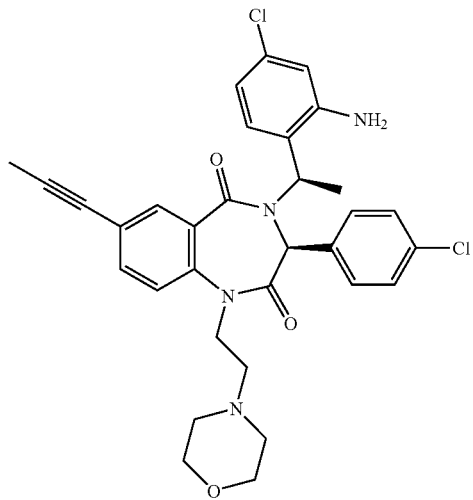

Mass spectrum (LCMS, ESI pos.): Calcd for C$_{32}$H$_{32}$Cl$_2$N$_4$O$_3$: 590.19; found: 591.0 (M+H)$^+$.

Example 97

4-[1-(2-Amino-4-chlorophenyl)ethyl]-3-(4-chlorophenyl)-7-iodo-2,3-dihydro-1H-1,4-benzodiazepin-5-one

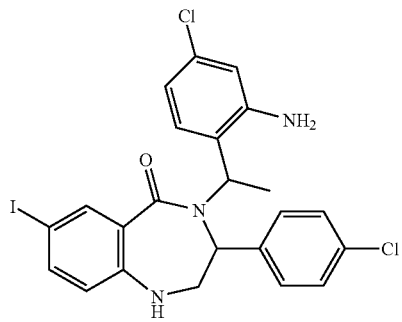

a) 4-[1-(4-Chloro-2-nitrophenyl)ethyl]-3-(4-chlorophenyl)-7-iodo-2,3-dihydro-1H-1,4-benzodiazepin-5-one A solution of borane methyl sulfide complex (1.68 mL, 2M in THF) was slowly added to a solution of 4-[1-(4-chloro-2-nitrophenyl)ethyl]-3-(4-chlorophenyl)-7-iodo-1,3-dihydro-1,4-benzodiazepine-2,5-one (500 mg, 0.839 mmol) in anhydrous tetrahydrofuran (25 mL). The resulting solution was heated at 65° C. for 2 h. Then, the reaction mixture was cooled at 0° C. and NaOH (10 mL, 3N) was slowly added. The solvent was evaporated and the residue partitioned between ice-cold water and ethyl acetate, dried ($Na_2SO_4$), and evaporated. Purification by chromatography on silica (AcOEt/Hexanes/$CH_2Cl_2$, 1:2:1) afforded a powder, which was triturated in ether to give the title compound (370 mg, 76%) a yellow solid: $^1$H NMR (400 MHz, $CDCl_3$) δ 1.70 (d, J=6.8 Hz, 3H, $CH_3$), 3.50 (d, J=14.0 Hz, 1H), 3.73 (dd, J=14.0, 6.4 Hz, 1H), 4.42 (br s, 1H, NH), 4.67 (d, J=6.4 Hz, 1H), 6.17 (q, J=6.8 Hz, 1H), 6.72 (d, J=8.4 Hz, 2H), 7.07 (d, J=8.4 Hz, 2H), 7.37 (dd, J=8.4, 2.0 Hz, 1H), 7.50 (dd, J=8.4, 2.0 Hz, 1H), 7.61–7.64 (m, 2H), 8.58 (d, J=2.0 Hz, 1H). Mass spectrum (LCMS, ESI pos.): Calcd for $C_{23}H_{18}Cl_2IN_3O_3$: 580.9; found: 582.0 (M+H)$^+$.

b) 4-[1-(2-Amino-4-chlorophenyl)ethyl]-3-(4-chlorophenyl)-7-iodo-2,3-dihydro-1H-1,4-benzodiazepin-5-one $^1$H NMR (400 MHz, $CDCl_3$) δ 1.63 (d, J=6.8 Hz, 3H), 3.60 (d, J=14.0 Hz, 1H), 4.05 (dd, J=14.0, 6.0 Hz, 1H), 4.72 (d, J=5.2 Hz, 1H), 6.12 (d, J=8.8 Hz, 1H), 6.33 (q, J=6.8 Hz, 1H), 6.49 (br s, 1H), 6.54 (dd, J=8.0, 1.6 Hz, 1H), 6.77 (d, J=8.4 Hz, 2H), 6.95–7.01 (m, 3H), 7.28 (dd, J=8.4, 2.0 Hz, 1H), 8.46 (d, J=2.0 Hz, 1H). Mass spectrum (LCMS, ESI pos.): Calcd for $C_{23}H_{20}Cl_2IN_3O$: 551.0; found: 552.0 (M+H)$^+$.

Example 98

4-[1-(2-amino-6-chloro-3-pyridyl)methyl]-3-(4-chlorophenyl)-7-iodo-1-[2-(2-methoxyethoxy)ethyl]-1,4-benzodiazepine-2,5-dione hydrochloride

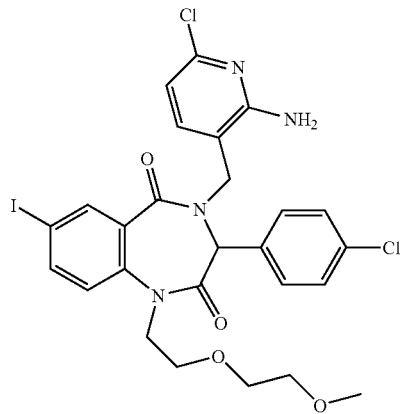

$^1$H NMR (400 MHz, $CDCl_3$) δ 3.31 (s, 3H), 3.42–3.53 (m, 4H), 3.64–3.67 (m, 2H), 3.91–3.97 (m, 1H), 4.31–4.38 (m, 1H), 5.00 (dd, J=33.6, 15.2 Hz, 2H), 5.56 (s, 1H), 6.85 (d, J=7.6 Hz, 1H), 6.86–6.89 (m, 2H), 7.10–7.13 (m, 3H), 7.64 (dd, J=8.4, 2.0 Hz, 1H), 7.86–7.88 (m, 2H). Mass spectrum (LCMS, ESI pos.): Calcd for $C_{26}H_{25}Cl_2IN_4O_4$: 654.0; found: 655.0 (M+H)$^+$.

Example 99

4-[1-(3-Amino-4-chlorophenyl)cyclopropyl]-3-(4-chlorophenyl)-1-[2-(4-morpholino)ethyl]-7-iodo-1,4-benzodiazepine-2,5-dione methanesulfonate

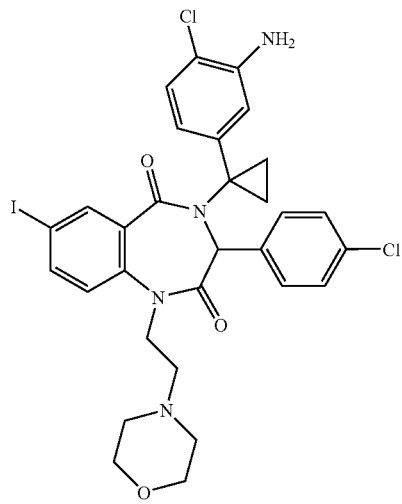

$^1$H NMR (400 MHz, $CDCl_3$) δ 1.29–1.38 (m, 2H), 1.53–1.60 (m, 1H), 1.81–1.86 (m, 1H), 3.17–3.29 (m, 4H), 3.65–4.11 (m, 7H), 4.47–4.54 (m, 1H), 5.98 (s, 1H), 6.75 (d, J=8.0 Hz, 2H), 6.86 (d, J=8.8 Hz, 1H), 7.11 (d, J=8.0 Hz, 2H), 7.21 (d, J=8.0 Hz, 1H), 7.33 (d, J=8.0 Hz, 1H), 7.42 (s,

1H), 7.64–7.67 (m, 1H), 7.83 (d, J=1.6 Hz, 1H). Mass spectrum (LCMS, ESI pos.): Calcd for $C_{30}H_{29}Cl_2IN_4O_3$: 690.0; found: 691.0 (M+H)+.

Example 100

(3S)-4-[1-(2-Amino-4-chlorophenyl)ethyl]-3-(4-chlorophenyl)-7-iodo-1-[(R)-2-(1-piperazinyl)-2-oxoethyl]-1,4-benzodiazepine-2,5-dione hydrochloride

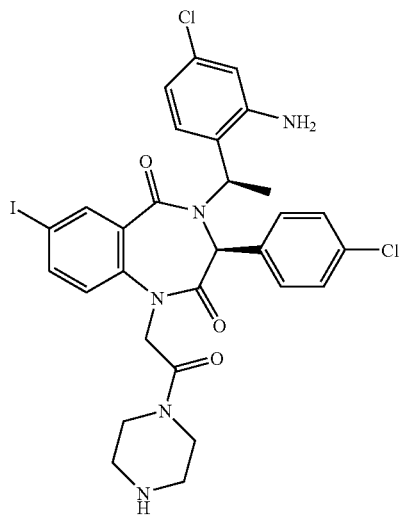

$^1$H NMR (400 MHz, CD$_3$OD) δ 1.72 (d, J=7.0 Hz, 3H), 3.31–3.40 (m, 2H), 3.88–3.95 (m, 6H), 4.64 (d, J=16.8 Hz, 1H), 5.05 (d, J=16.8 Hz, 1H), 5.31 (s, 1H), 6.26 (q, J=7.0 Hz, 1H), 6.59 (dd, J=8.4, 2.4 Hz, 1H), 6.79–6.83 (m, 2H), 6.93–7.00 (m, 4H), 7.28–7.30 (d, J=8.0 Hz, 1H), 7.60 (dd, J=8.8, 2.4 Hz, 1H), 7.80 (d, J=2.0 Hz, 1H). Mass spectrum (LCMS, ESI pos.): Calcd for $C_{29}H_{28}Cl_2IN_5O_3$: 691.0; found: 692.0 (M+H)+.

Example 101

4-(4-Chloro-2-methyl-benzyl)-3-(4-chloro-phenyl)-7-iodo-1-(2-morpholin-4-yl-ethyl)-3,4-dihydro-1H-benzo[e][1,4]diazepine-2,5-dione

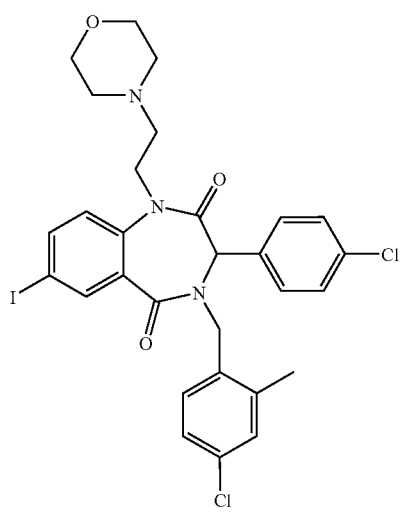

$^1$H NMR (400 MHz, DMSO-d$_6$) δ 7.95–7.96 (d, J=2.1 Hz, 1H), 7.46–7.52 (m, 1H), 7.33–7.36 (m, 1H), 7.28–7.29 (m, 4H), 7.16–7.24 (m, 2H), 6.99–7.02 (m, 2H), 6.68–6.73 (m, 3H), 5.34–5.40 (d, J=14.6 Hz, 1H), 5.30 (s, 1H), 4.68–4.72 (d, J=14.6 Hz, 1H), 4.46–4.56 (m, 1H), 3.58–3.63 (m, 5H), 2.40–2.54 (m, 5H). Mass spectrum (LCMS, ESI pos.): Calcd for $C_{29}H_{28}Cl_2IN_3O_3$: 663.0; found 664.1 (M+H).

Example 102

3-(S)-(4-Chloro-phenyl)-4-[1-(R)-(4-chloro-phenyl)-ethyl]-7-iodo-1-(2-morpholin-4-yl-2-oxo-ethyl)-3,4-dihydro-1H-benzo[e][1,4]diazepine-2,5-dione

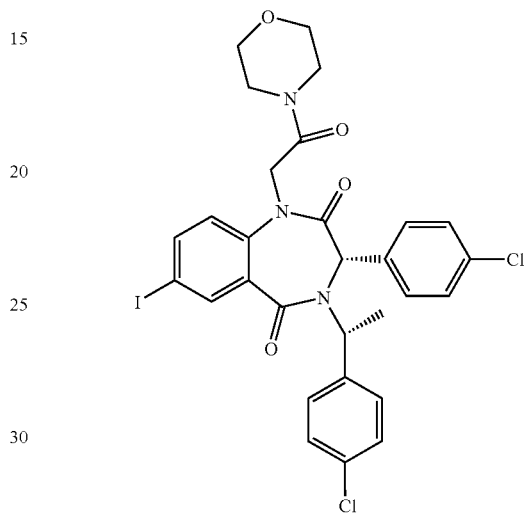

$^1$H NMR (400 MHz, DMSO-d$_6$) δ 7.91–7.92 (d, J=2.1 Hz, 1H), 7.51–7.35 (m, 2H), 7.43–7.46 (m, 1H), 7.35–7.40 (m, 2H), 6.90–6.96 (m, 2H), 6.72–6.76 (m, 2H), 6.60–6.63 (d, J=8.6 Hz, 1H), 6.40–6.48 (m, 1H), 5.35–5.36 (s, 1H), 5.00–5.042 (d, J=16.0 Hz, 1H), 4.02–4.07 (d, J=16.1 Hz, 1H), 3.44–3.88 (m, 9H), 1.71–1.74 (d, J=7.1 Hz, 2H). Mass spectrum (LCMS, ESI pos.): Calcd for $C_{29}H_{26}Cl_2IN_3O_4$: 677.0; found 677.8 (M+H).

Example 103

3-(S)-(4-Chloro-phenyl)-4-[1-(R)-(4-chloro-phenyl)-ethyl]-7-iodo-1-(2-morpholin-4-yl-ethyl)-3,4-dihydro-1H-benzo[e][1,4]diazepine-2,5-dione

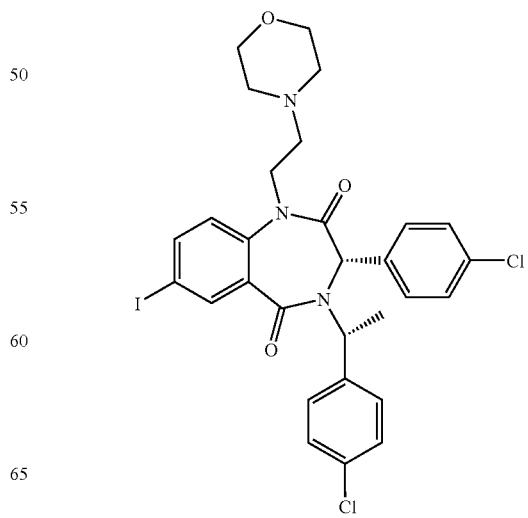

¹H NMR (400 MHz, DMSO-d₆) δ 7.94–7.95 (d, J=2.1 Hz, 1H), 7.40–7.48 (m, 3H), 7.26–7.30 (m, 2H), 6.84–6.88 (m, 2H), 6.60–6.68 (d, J=8.8 Hz, 2H), 6.46–6.50 (d, J=7.5 Hz, 2H), 6.36.44(m, 1H), 5.30 (s, 1H), 4.44–4.54 (m, 1H), 4.04–4.10 (m, 1H), 3.50–3.68 (m, 5H), 2.58–2.60 (m, 1H), 2.36–2.46 (m, 3H), 2.24–2.28 (m, 1H), 1.73–1.75 (d, J=7.1 Hz, 2H). Mass spectrum (LCMS, ESI pos.): Calcd for $C_{29}H_{28}Cl_2IN_3O_3$: 663.0; found 664.1 (M+H).

Example 104

3-(R)-(4-Chloro-phenyl)-4-[1-(R)-(4-chloro-phenyl)-ethyl]-7-iodo-1-(2-morpholin-4-yl-ethyl)-3,4-dihydro-1H-benzo[e][1,4]diazepine-2,5-dione

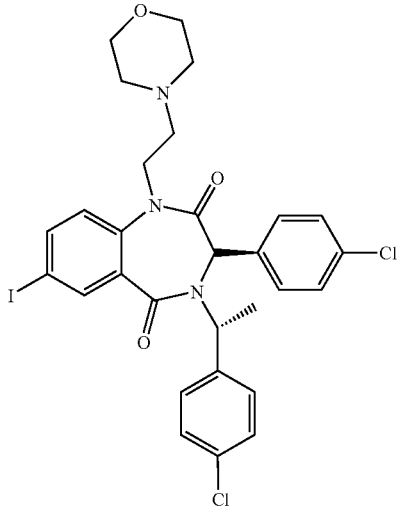

¹H NMR (400 MHz, DMSO-d₆) δ 7.99–8.01 (d, J=2.1 Hz, 1H), 7.28–7.48 (m, 5H), 7.08–7.10 (d, J=8.6 Hz, 2H), 6.83–6.85 (d, J=8.6 Hz, 2H), 6.59–6.62 (d, J=8.6 Hz, 2H), 6.34–6.40 (m, 1H), 5.32–5.34 (s, 1H), 4.04–4.22 (m, 2H), 3.42–3.58 (m, 5H), 2.40–2.46 (m, 1H), 2.20–2.32 (m, 3H), 1.58–1.63 (d, J=7.1 Hz, 3H). Mass spectrum (LCMS, ESI pos.): Calcd for $C_{29}H_{28}Cl_2IN_3O_3$: 663.0; found 664.2 (M+H).

Example 105

3-(S)-(4-Chloro-phenyl)-4-[1-(R)-(4-chloro-phenyl)-ethyl]-7-iodo-1-[2-(2-methoxy-ethoxy)-ethyl]-3,4-dihydro-1H-benzo[e][1,4]diazepine-2,5-dione

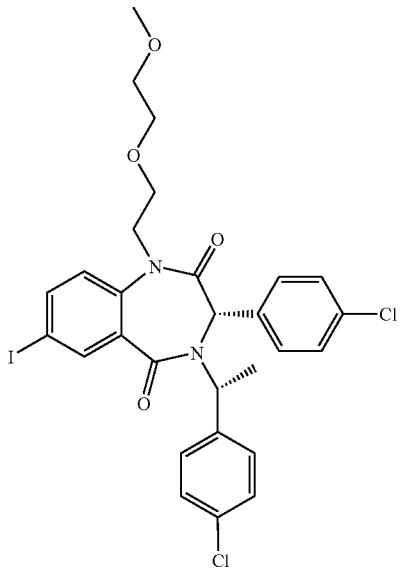

¹H NMR (400 MHz, DMSO-d₆) δ 7.91–7.92 (d, J=2.1 Hz, 1H), 7.40–7.50 (m, 3H), 7.28–7.30 (m, 2H), 6.82–6.86 (m, 3H), 6.46–6.49 (m, 2H), 6.36–6.42 (m, 2H), 5.28 (s, 1H), 4.10–4.20 (m, 2H), 3.92–4.00 (m, 2H), 3.80–3.88 (m, 1H), 3.68–3.72 (m, 2H), 3.44–3.60 (m, 4H), 1.70–1.73 (d, J=7.3 Hz, 3H). Mass spectrum (LCMS, ESI pos.): Calcd for $C_{28}H_{27}Cl2IN_2O_4$: 652.0; found 653.3 (M+H).

Example 106

3-(S)-(4-Chloro-phenyl)-4-[1-(R)-(4-chloro-phenyl)-ethyl]-7-(1-hydroxyimino-ethyl)-3,4-dihydro-1H-benzo[e][1,4]diazepine-2,5-dione

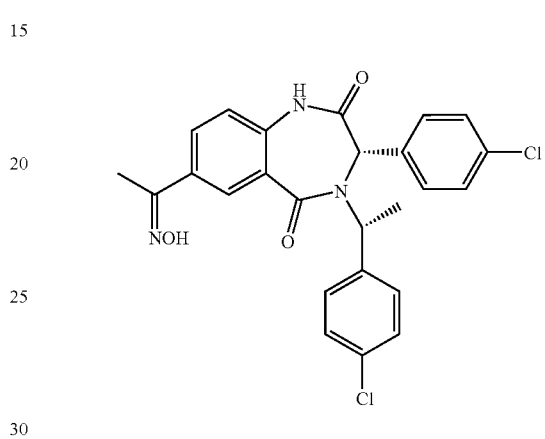

A solution of 7-Acetyl-3-(S)-(4-chloro-phenyl)-4-[1-(R)-(4-chloro-phenyl)-ethyl]-3,4-dihydro-1H-benzo[e][1,4]diazepine-2,5-dione (50 mg, 0.11 mmol), hydroxylamine hydrochloride salt (22 mg, 0.33 mmol), triethylamine (0.074 mL, 0.55 mmol) in EtOH (0.5 mL) was heated to 80° C. After 2 h reaction solution was applied to a prep tlc plate (Analtech Silica Gel GF, 20×20 cm, 2000 microns) and developed using methylene chloride/MeOH 10:1. Desired bands were scraped off, extracted with MeOH, filtered and concentrated to give the title compound (2.4 mg). ¹H NMR (400 MHz, DMSO-d₆) δ 7.82–7.83 (m, 1H), 7.47–7.51 (m, 3H), 7.32 (s, 3H), 7.26–7.30 (m, 2H), 6.80–6.84 (m, 2H), 6.66–6.70 (d, J=8.4 Hz, 2H), 6.52–6.55 (d, J=8.6 Hz, 2H), 6.36–6.42 (m, 2H), 5.17 (s, 1H), 1.67–1.71 (d, J=7.3 Hz, 3H). Mass spectrum (LCMS, ESI pos.): Calcd for $C_{25}H_{21}Cl_2N_3O_3$: 481.1; found 482.1 (M+H).

Example 107

7-Iodo-4-naphthalen-1-ylmethyl-3-(4-trifluoromethoxy-phenyl)-3,4-dihydro-1H-benzo[e][1,4]diazepine-2,5-dione

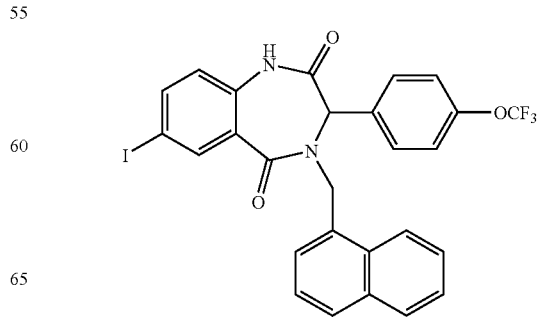

¹H NMR (400 MHz, DMSO-d₆) δ 10.76–10.80 (s, 1H), 8.16–8.20 (d, J=8.0 Hz, 1H), 7.85–8.00 (m, 2H), 7.80–7.82 (m, 1H), 7.54–7.61 (m, 5H), 7.00–7.20 (m, 4H), 6.60–6.64 (d, J=8.6 Hz, 1H), 5.86–6.00 (d, J=14.9 Hz, 1H), 5.50 (s, 1H), 5.10–5.16 (d, J=15.1 Hz, 1H). Mass spectrum (LCMS, ESI pos.): Calcd for C₂₇H₁₈F₃IN₂O₃: 602.0; found 603.3 (M+H).

Example 108

4-Benzo[1,3]dioxol-5-ylmethyl-3-(4-chloro-phenyl)-7-iodo-3,4-dihydro-1H-benzo[e][1,4]diazepine-2,5-dione

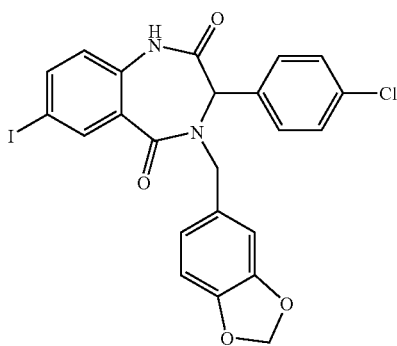

¹H NMR (400 MHz, DMSO-d₆) δ 7.91–7.92 (m, 1H), 7.55–7.60 (m, 1H), 7.38–7.41 (m, 1H), 7.25–7.30 (m, 3H), 7.10–7.13 (d, J=8.6 Hz, 2H), 6.87–7.00 (m, 2H), 6.77–6.81 (d, J=7.7 Hz, 1H), 6.57–6.63 (m, 1H), 6.33–6.37 (m, 1H), 5.93–5.96 (m, 1H), 5.85–5.88 (m, 1H), 5.43–5.45 (s, 1H). Mass spectrum (LCMS, ESI pos.): Calcd for C₂₃H₁₆ClIN₂O₄: 545.9; found 547.8 (M+H).

Example 109

4-Benzo[1,3]dioxol-5-ylmethyl-7-iodo-3-(4-trifluoromethoxy-phenyl)-3,4-dihydro-1H-benzo[e][1,4]diazepine-2,5-dione

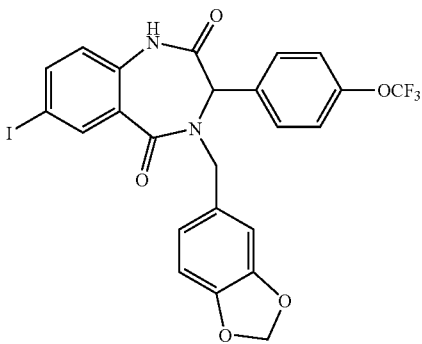

¹H NMR (400 MHz, DMSO-d₆) δ 7.88–7.90 (m, 1H), 7.54–7.70 (m, 1H), 7.30–7.40 (m, 1H), 7.15–7.17 (m, 1H), 6.95–7.04 (m, 3H), 6.78–6.81 (d, J=7.9 Hz, 2H), 6.59–6.63 (d, J=8.6 Hz, 2H), 6.32–6.36 (m, 1H), 5.93–5.96 (m, 1H), 5.83–5.87 (m, 2H), 5.48–5.49 (s, 1H). Mass spectrum (LCMS, ESI pos.): Calcd for C₂₄H₁₆F₃IN₂O₅: 596.01; found 597.2 (M+H).

Example 110

7-Iodo-4-(2-pyridin-2-yl-ethyl)-3-(4-trifluoromethoxy-phenyl)-3,4-dihydro-1H-benzo[e][1,4]diazepine-2,5-dione

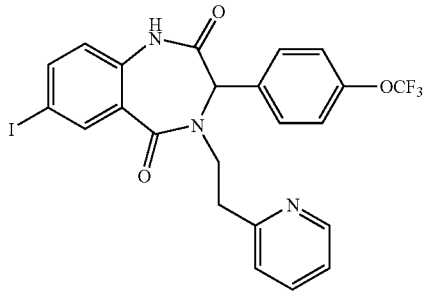

¹H NMR (400 MHz, DMSO-d₆) δ 8.45–8.47 (m, 1H), 7.82–7.84 (m, 2H), 7.71–7.76 (m, 1H), 7.51–7.53 (m, 1H), 7.38–7.41 (m, 1H), 7.23–7.27 (m, 1H), 7.08–7.14 (m, 4H), 6.58–6.61 (d, J=8.4 Hz, 1H), 5.60 (s, 1H), 4.54–4.62 (m, 1H), 3.92–4.01 (m, 1H), 3.18–3.28 (m, 2H). Mass spectrum (LCMS, ESI pos.): Calcd for C₂₃H₁₇F₃IN₃O₃: 567.0; found 568.1 (M+H).

Example 111

4-Benzyl-3-(4-chloro-phenyl)-7-iodo-3,4-dihydro-1H-benzo[e][1,4]diazepine-2,5-dione

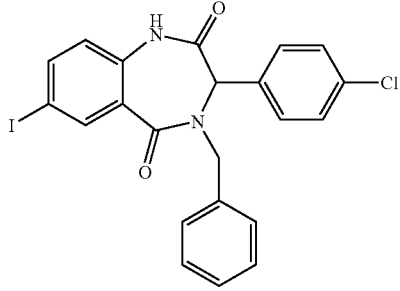

¹H NMR (400 MHz, DMSO-d₆) δ 7.80–7.82 (m, 1H), 7.59–7.62 (m, 2H), 7.20–7.50 (m, 7H), 6.90–7.00 (m, 2H), 6.65–6.70 (d, J=8.6 Hz, 1H), 5.55–5.58 (m, 1H), 5.20–5.30 (d, J=14 Hz, 1H), 4.77–4.84 (d, J=14.6 Hz, 1H). Mass spectrum (LCMS, ESI pos.): Calcd for C₂₂H₁₆ClIN₂O₂: 501.9; found 503.1 (M+H).

Example 112

3-(4-Chloro-phenyl)-7-iodo-4-phenethyl-3,4-dihydro-1H-benzo[e][1,4]diazepine-2,5-dione

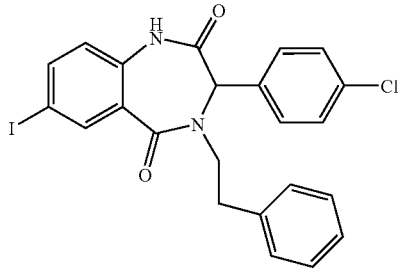

$^1$H NMR (400 MHz, DMSO-d$_6$) δ 10.8–10.9 (s, 1H), 7.78–7.80 (m, 1H), 7.56–7.60 (m, 2H), 7.24–7.36 (m, 5H), 7.16–7.20 (m, 2H), 6.95–7.04 (m, 1H), 6.64–6.68 (d, J=8.4 Hz, 1H), 5.70–5.76 (s, 1H), 4.18–4.28 (m, 1H), 3.76–3.84 (m, 1H), 2.84–3.10 (m, 2H). Mass spectrum (LCMS, ESI pos.): Calcd for C$_{23}$H$_{18}$ClIN$_2$O$_2$: 516.0; found 517.1 (M+H).

Example 113

4-Benzyl-7-iodo-3-(4-trifluoromethoxy-phenyl)-3,4-dihydro-1H-benzo[e][1,4]diazepine-2,5-dione

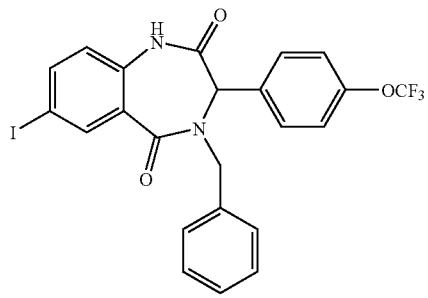

$^1$H NMR (400 MHz, DMSO-d$_6$) δ 7.72–7.80 (s, 1H), 7.56–7.60 (m, 2H), 7.28–7.50 (m, 7H), 7.10–7.18 (m, 2H), 6.60–6.70 (m, 1H), 5.60 (s, 1H), 5.28–5.34 (d, J=14.6 Hz, 1H), 4.76–4.82 (d, J=14.8 Hz, 1H). Mass spectrum (LCMS, ESI pos.): Calcd for C$_{23}$H$_{16}$F$_3$IN$_2$O$_3$: 552.0; found 553.1 (M+H).

Example 114

7-Iodo-4-phenethyl-3-(4-trifluoromethoxy-phenyl)-3,4-dihydro-1H-benzo[e][1,4]diazepine-2,5-dione

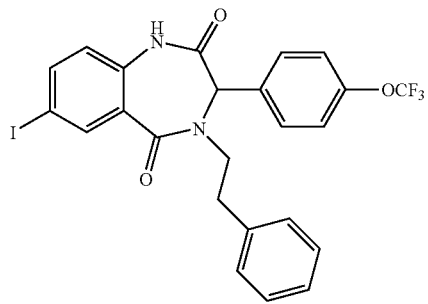

$^1$H NMR (400 MHz, DMSO-d$_6$) δ 10.8–11.0 (s, 1H), 7.50–7.64 (m, 3H), 7.02–7.40 (m, 8H), 6.57–7.0 (m, 1H), 5.60 (s, 1H), 4.40–4.40 (m, 1H), 3.80–3.90 (m, 1H), 2.90–3.10 (m, 2H). Mass spectrum (LCMS, ESI pos.): Calcd for C$_{24}$H$_{18}$F$_3$IN$_2$O$_3$: 566.0; found 567.0 (M+H).

Example 115

Fluorescent Peptide Assay

The inhibition of MDM2 binding to p53 was measured using a p53 peptide analogue binding to MDM2 residues 17–125. The published crystal structure of this complex (Kussie et al., *Science* 274:948–953 (1996)) validates this fragment as containing the p53 binding site, and we have solved the x-ray structure of the p53 peptide analogue MPRFMDYWEGLN, described to be a peptide inhibitor of the MDM2 p53 interaction (Bottger et al., *J. Mol. Biol.* 269:744–756 (1997)). The assay uses N terminal fluorescein RFMDYWEGL peptide (Fl 9mer).

The mdm2 17–125 was produced as a glutathione S transferase fusion as follows: cDNA encoding residues 17–125 were cloned into pGEX4t-3 (Pharmacia) as follows. PCR was performed using ATCC item number 384988 containing partial human mdm2 sequence as template and the following primers: Forward: 5'-CTC TCT C GGATCCCA GAT TCC AGC TTC GGA ACA AGA G; Reverse: 5'-TAT ATA TCTCGAGTC AGT TCT CAC TCA CAG ATG TAC CTG AG. The PCR product was then digested with BamHI and XhoI (sequence recognition sites underlined in primers), gel purified, and ligated into pGEX4t-3 which had also been digested with BamHI and XhoI. Plasmids were transfected into *E. coli* X90 strain, grown to an OD of 1.0 in TB 0.2% glucose 100 µg/mL ampicillin and induced with 1 mM IPTG. Cells were harvested 5 hours post induction, centrifuged, and resuspended in PBS 10 mL/g cell paste. Cells were lysed in an Avestin microfluidizer, centrifuged, and the supernatant bound to a glutathione sepharose 4B resin (Pharmacia). The resin was washed with PBS and the MDM2 17–125 cleaved from the GST by the addition of 2 µg/mL thrombin (Enzyme Research Labs). The cleaved MDM2 was further purified on Sepharose SP Fast Flow resin (Pharmacia), eluting with 20 mM HEPES pH 7.5 150 mM NaCl. Glutathione was added to 5 mM, and the protein stored at −70° C.

Test compound was incubated for 15 minutes with 30 nM fluorescein peptide Fl 9mer and 120 nM MDM2 17–125 in 50 mM HEPES pH 7.5, 150 mM NaCl, 3 mM octyl glucoside. The polarization of the fluorescein label was thereafter measured by excitation at 485 nm and emission at 530 nm. Polarization was expressed as a percent of a no compound control, using buffer with Fl 9mer but without MDM2 as background.

Compounds of the present invention inhibited the binding of p53 to MDM2. The potency of the compounds was measured as IC$_{50}$, which is a measure of the concentration of the test compound required to inhibit 50% binding between MDM2 and p53. The IC$_{50}$ values for compounds of the present invention ranged from 0.05 µM to >100 µM. See examples below.

| Compound | range (µM) |
| --- | --- |
| 4-[(R)-1(2-amino-4-chlorophenyl)ethyl]-(3S)-3-(4-chlorophenyl)-7-iodo-1-[2-(2-methoxyethoxy)ethyl]-1,4-benzodiazepine-2,5-dione | 0.1–1.0 |
| 4-[(R)-1(2-Amino-4-chlorophenyl)-ethyl]-(3S)-3-(4-chloro-phenyl)-7-iodo-1-[3-(4-methyl-piperazin-1-yl)-prop,yl]-3,4-dihydro-1H-benzo[e][1,4]diazepine-2,5-dione | 0.1–1.0 |
| 5-{(3S)-3-(4-Chlorophenyl)-4-[(R)-1-(4-chloro-phenyl)-ethyl]-7-iodo-2,5-dioxo-2,3,4,5-tetrahydro-benzo[e][1,4]diazepin-1-yl}-pentanoic acid | 0.1–1.0 |
| (3S)-4-[1-(2-Amino-4-chlorophenyl)ethyl]-3-(4-chlorophenyl)-7-iodo-1-[(R)-2-(1-piperazinyl)-2-oxoethyl]-1,4-benzodiazepine-2,5-dione hydrochloride | 1.0–2.0 |
| 4-(R)-[1-(2-Amino-4-chloro-5-fluoro-phenyl)-ethyl]-3(S)-(4-chloro-phenyl)-7-iodo-1-(2-morpholin-4-yl-ethyl)-3,4-dihydro-1H-benzo[e][1,4]diazepine-2,5-dione | 1.0–3.0 |

Example 116

Tablet Preparation

Tablets containing 25.0, 50.0, and 100.0 mg, respectively, of the compound of Example 1 ("active compound") are prepared as illustrated below:

TABLET FOR DOSES CONTAINING FROM 25–100 MG OF THE ACTIVE COMPOUND

|  | Amount-mg | | |
| --- | --- | --- | --- |
| Active compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

Example 117

Intravenous Solution Preparation

An intravenous dosage form of the compound of Example 1 ("active compound") is prepared as follows:

| Active compound | 0.5–10.0 mg |
| --- | --- |
| Sodium citrate | 5–50 mg |
| Citric acid | 1–15 mg |
| Sodium chloride | 1–8 mg |
| Water for injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A compound of Formula II:

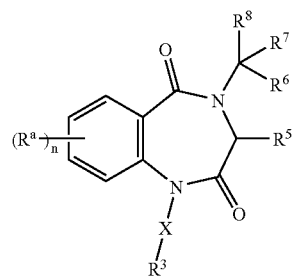

or a pharmaceutically acceptable salt thereof; wherein:
each instance of $R^a$ is independently halo, $C_{1-6}$ alkyl, $C_{2-6}$ alkenyl, $C_{2-6}$ alkynyl, cyano, $C_{3-8}$ cycloalkyl, hydroxy, $C_{1-6}$ alkoxy, carboxy, ($C_{1-6}$ alkoxy)carbonyl, $C_{1-6}$ acyl, carbamoyl, ($C_{1-6}$ alkyl)aminocarbonyl, alkylthio, amino or nitro;

n is 0; or n is 1 and $R^a$ occurs at the 7- or 8-position; or n is 2 and $R^a$ occurs at the 7- and 8-positions;

X is a bivalent radical of: a $C_{1-6}$ alkane, an optionally-substituted $C_{6-10}$ arene, an optionally-substituted 5- to 7-membered heteroarene wherein 1 or 2 ring atoms are heteroatoms, an optionally-substituted ($C_{6-10}$ aryl)$C_{1-6}$ alkane, or an optionally-substituted heteroaryl($C_{1-6}$) alkane in which the heteroaryl portion contains 5 to 7 ring atoms and wherein 1 or 2 of the ring atoms are heteroatoms;

$R^3$ is —$CO_2R^d$ or —$CO_2M$, where $R^d$ is hydrogen, $C_{1-6}$ alkyl or optionally-substituted $C_{3-8}$ cycloalkyl, and M is a cation;

$R^5$ is $C_{3-8}$ cycloalkyl, $C_{6-10}$ aryl, 5- to 7-membered heteroaryl wherein 1 or 2 of the ring atoms are heteroatoms, ($C_{3-8}$ cycloalkyl)alkyl, ($C_{6-10}$ aryl)alkyl, (heteroaryl)alkyl in which the heteroaryl portion contains 5 to 7 ring atoms and wherein 1 or 2 of the ring atoms are heteroatoms, or 5- to 7-membered saturated or partially unsaturated heterocycle wherein 1 or 2 of the ring atoms are heteroatoms, in which each of the preceding groups is optionally substituted;

$R^6$ is $C_{3-8}$ cycloalkyl, $C_{6-10}$ aryl, 5- to 7-membered heteroaryl wherein 1 or 2 of the ring atoms are heteroatoms, ($C_{3-8}$ cycloalkyl)alkyl, ($C_{6-10}$ aryl)alkyl, (heteroaryl)alkyl in which the heteroaryl portion contains 5 to 7 ring atoms and wherein 1 or 2 of the ring atoms are heteroatoms, or 5- to 7-membered saturated or partially unsaturated heterocycle wherein 1 or 2 of the ring atoms are heteroatoms, in which each of the preceding groups is optionally substituted;

$R^7$ is hydrogen, $C_{1-6}$ alkyl, $C_{3-8}$ cycloalkyl or ($C_{3-8}$ cycloalkyl)alkyl; and $R^8$ is hydrogen or $C_{1-6}$ alkyl.

2. The compound according to claim 1, wherein $R^a$ is halo, $C_{2-6}$ alkynyl, carboxy, ($C_{1-6}$ alkoxy)carbonyl, $C_{1-6}$ acyl or carbamoyl.

3. The compound according to claim 1, wherein $R^a$ is iodo, bromo, propynyl, chloro, ethynyl, acetyl, methoxycarbonyl, carboxy or carbamoyl.

4. The compound according to claim 1, wherein $R^a$ is iodo.

5. The compound according to claim 1, wherein n is 1.

6. The compound according to claim 1, wherein X is a bivalent radical of: a $C_{1-6}$ alkane, optionally-substituted benzene, optionally-substituted furan, optionally-substituted thiophene or optionally-substituted pyrrole.

7. The compound according to claim 1, wherein X is a bivalent radical of: methane, ethane, n-propane, n-butane, n-pentane, n-hexane, benzene or furan.

8. The compound according to claim 1, wherein X is a bivalent radical of n-butane.

9. The compound according to claim 1, wherein $R^3$ is —$CO_2R^d$ or —$CO_2M$, where $R^d$ is hydrogen or $C_{1-6}$ alkyl, and M is a cation.

10. The compound according to claim 1, wherein $R_3$ is —$CO_2R^d$, where $R^d$ is hydrogen or $C_{1-4}$ alkyl.

11. The compound according to claim 1, wherein $R^3$ is —COOH.

12. The compound according to claim 1, wherein $R^5$ is optionally-substituted phenyl.

13. The compound according to claim 1, wherein $R^5$ is phenyl substituted once in the 4-position or twice in the 3- and 4-positions, wherein each occurrence of substitution is independently selected from the group consisting of halo, trifluoromethyl, trifluoromethoxy, nitro and amino.

14. The compound according to claim 1, wherein $R^5$ is 4-chlorophenyl, 4-trifluoromethylphenyl, 4-trifluoromethoxyphenyl, 4-chloro-3-nitrophenyl, 3-amino-4-chlorophenyl or 3-bromophenyl.

15. The compound according to claim 1, wherein $R^5$ is 4-chlorophenyl.

16. The compound according to claim 1, wherein $R^6$ is optionally-substituted phenyl, optionally-substituted benzyl, optionally-substituted pyridyl or optionally-substituted naphthyl.

17. The compound according to claim 1, wherein $R^6$ is optionally-substituted phenyl.

18. The compound according to claim 1, wherein $R^6$ is phenyl optionally substituted once in the p-position or twice in the m- and p-positions, or twice at the o- and p-positions, wherein each occurrence of substitution is independently selected from the group consisting of halo, nitro and amino.

19. The compound according to claim 1, wherein $R^6$ is phenyl, 4-chlorophenyl, 3,4-dichlorophenyl, 3-amino-4-chlorophenyl, 2-amino-4-chlorophenyl, 2-amino-4-chloro-5-fluorophenyl or 4-chloro-3-nitrophenyl.

20. The compound according to claim 1, wherein $R^6$ is 2-amino-4-chlorophenyl.

21. The compound according to claim 1, wherein $R^7$ is hydrogen, $C_{1-6}$ alkyl or $C_{3-6}$ cycloalkyl.

22. The compound according to claim 1, wherein $R^7$ is hydrogen, methyl and cyclopropyl.

23. The compound according to claim 1, wherein $R^7$ is methyl.

24. The compound according to claim 1, wherein $R^8$ is hydrogen, methyl or ethyl.

25. The compound according to claim 1, wherein $R_8$ is hydrogen.

26. The compound according to claim 1, wherein:
each instance of $R^a$ is independently halo, $C_{2-6}$ alkynyl, carboxy, ($C_{1-6}$ alkoxy)carbonyl, $C_{1-6}$ acyl or carbamoyl;
n is 1 and $R^a$ occurs at the 7-position; or n is 2 and $R^a$ occurs at the 7- and 8-positions;
X is a bivalent radical of a $C_{1-6}$ alkane, optionally-substituted benzene, optionally-substituted furan, optionally-substituted thiophene, optionally-substituted pyrrole or optionally-substituted pyridine;
$R^3$ is —$CO_2R^d$ or —$CO_2M$, where $R^d$ is hydrogen or $C_{1-6}$ alkyl, and M is a cation;
$R^5$ is optionally-substituted phenyl;
$R^6$ is optionally-substituted phenyl, optionally-substituted benzyl, optionally-substituted pyridyl or optionally-substituted naphthyl;
$R^7$ is hydrogen, $C_{1-6}$ alkyl or $C_{3-6}$ cycloalkyl; and
$R^8$ is hydrogen.

27. A compound of Formula III:

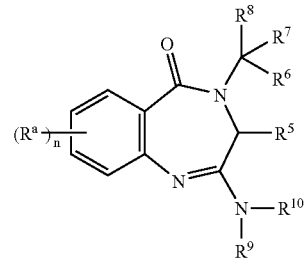

or a pharmaceutically acceptable salt thereof; wherein:
each instance of $R^a$ is independently halo, $C_{1-6}$ alkyl, $C_{2-6}$ alkenyl, $C_{2-6}$ alkynyl, cyano, $C_{3-8}$ cycloalkyl, hydroxy, $C_{1-6}$ alkoxy, carboxy, ($C_{1-6}$ alkoxy)carbonyl, $C_{1-6}$ acyl, carbamoyl, ($C_{1-6}$ alkyl)aminocarbonyl, amino, alkylthio or nitro;
n is 0; or n is 1 and $R^a$ occurs at the 7- or 8-position; or n is 2 and $R^a$ occurs at the 7- and 8-positions;
$R^5$ is $C_{3-8}$ cycloalkyl, $C_{6-10}$ aryl, 5- to 7-membered heteroaryl wherein 1 or 2 of the ring atoms are heteroatoms, ($C_{3-8}$ cycloalkyl)alkyl, ($C_{6-10}$ aryl)alkyl, (heteroaryl)alkyl in which the heteroaryl portion contains 5 to 7 ring atoms and wherein 1 or 2 of the ring atoms are heteroatoms, or 5- to 7-membered saturated or partially unsaturated heterocycle wherein 1 or 2 of the ring atoms are heteroatoms, in which each of the preceding groups is optionally substituted;
$R^6$ is $C_{3-8}$ cycloalkyl, $C_{6-10}$ aryl, 5- to 7-membered heteroaryl wherein 1 or 2 of the ring atoms are heteroatoms, ($C_{3-8}$ cycloalkyl)alkyl, ($C_{6-10}$ aryl)alkyl, (heteroaryl)alkyl in which the heteroaryl portion contains 5 to 7 ring atoms and wherein 1 or 2 of the ring atoms are heteroatoms, or 5- to 7-membered saturated or partially unsaturated heterocycle wherein 1 or 2 of the ring atoms are heteroatoms, in which each of the preceding groups is optionally substituted;
$R^7$ is hydrogen, $C_{1-6}$ alkyl, $C_{3-8}$ cycloalkyl or ($C_{3-8}$ cycloalkyl)alkyl;
$R^8$ is hydrogen or $C_{1-6}$ alkyl;
$R^9$ is hydrogen, $C_{1-6}$ alkyl, $C_{3-6}$ cycloalkyl, hydroxy($C_{1-6}$) alkyl, amino($C_{1-6}$) alkyl, carboxy($C_{1-6}$) alkyl, ($C_{1-6}$ alkoxy)carbonyl, ($C_{1-6}$ alkoxy)carbonyl($C_{1-6}$) alkyl, carbamoyl, carbamoyl($C_{1-6}$) alkyl, ($C_{1-6}$ alkylamino)carbonyl or ($C_{1-6}$ alkylamino)carbonyl($C_{1-6}$) alkyl; and
$R^{10}$ is hydrogen or $C_{1-6}$ alkyl.

28. The compound according to claim 27, wherein $R^a$ is halo, $C_{2-6}$ alkynyl, carboxy, ($C_{1-6}$ alkoxy)carbonyl, $C_{1-6}$ acyl or carbamoyl.

29. The compound according to claim 27, wherein $R^a$ is iodo, bromo, chloro, ethynyl, propynyl, acetyl, methoxycarbonyl, carboxy or carbamoyl.

30. The compound according to claim 27, wherein $R^a$ is iodo.

31. The compound according to claim 27, wherein n is 1.

32. The compound according to claim 27, wherein $R^5$ is optionally-substituted phenyl.

33. The compound according to claim 27, wherein $R^5$ is phenyl substituted once in the 4-position or twice in the 3- and 4-positions, wherein each occurrence of substitution is independently selected from the group consisting of halo, trifluoromethyl, trifluoromethoxy, nitro and amino.

34. The compound according to claim 27, wherein $R^5$ is 4-chlorophenyl, 4-trifluoromethylphenyl, 4-trifluoromethoxyphenyl, 4-chloro-3-nitrophenyl, 3-amino-4-chlorophenyl or 3-bromophenyl.

35. The compound according to claim 27, wherein $R^5$ is 4-chlorophenyl.

36. The compound according to claim 27, wherein $R^6$ is optionally-substituted phenyl, optionally-substituted benzyl, optionally-substituted pyryidyl or optionally-substituted naphthyl.

37. The compound according to claim 27, wherein $R^6$ is optionally-substituted phenyl.

38. The compound according to claim 27, wherein $R^6$ is phenyl optionally substituted once in the p-position or twice in the m- and p-positions, or twice at the o- and p-position, wherein each occurrence of substitution is independently selected from the group consisting of halo, nitro and amino.

39. The compound according to claim 27, wherein $R^6$ is phenyl, 4-chlorophenyl, 3,4-dichlorophenyl, 2-amino-4-chlorophenyl, 2-amino-4-chloro-5-fluorophenyl, 3-amino-4-chlorophenyl or 4-chloro-3-nitrophenyl.

40. The compound according to claim 27, wherein $R^6$ is 2-amino-4-chlorophenyl.

41. The compound according to claim 27, wherein $R^7$ is hydrogen, $C_{1-6}$ alkyl or $C_{3-6}$ cycloalkyl.

42. The compound according to claim 27, wherein $R^7$ is hydrogen, methyl and cyclopropyl.

43. The compound according to claim 27, wherein $R^7$ is methyl.

44. The compound according to claim 27, wherein $R^8$ is hydrogen, methyl or ethyl.

45. The compound according to claim 27, wherein $R^8$ is hydrogen.

46. The compound according to claim 27, wherein $R^9$ is hydrogen, $C_{1-6}$ alkyl, hydroxy($C_{1-6}$) alkyl, amino($C_{1-6}$) alkyl or carbamoyl($C_{1-6}$) alkyl.

47. The compound according to claim 27, wherein $R^9$ is hydrogen, methyl, 2-hydroxyethyl, 3-hydroxypropyl, 2-aminoethyl, carbamoylmethyl or carbamoylethyl.

48. The compound according to claim 27, wherein $R^{10}$ is hydrogen or $C_{1-6}$ alkyl.

49. The compound according to claim 27, wherein $R^{10}$ is hydrogen, methyl or ethyl.

50. The compound according to claim 27, wherein $R^{10}$ is hydrogen.

51. The compound according to claim 27, wherein:
each instance of $R^a$ is independently halo, $C_{2-6}$ alkynyl, carboxy, ($C_{1-6}$ alkoxy)carbonyl, $C_{1-6}$ acyl or carbamoyl;
n is 1 and $R^a$ occurs at the 7-position; or n is 2 and $R^a$ occurs at the 7- and 8-positions;
$R^5$ is optionally-substituted phenyl;
$R_6$ is optionally-substituted phenyl, optionally-substituted benzyl, optionally-substituted pyridyl or optionally-substituted naphthyl;
$R^7$ is hydrogen, $C_{1-6}$ alkyl or $C_{3-6}$ cycloalkyl;
$R^8$ is hydrogen;
$R^9$ is hydrogen, $C_{1-6}$ alkyl, hydroxy($C_{1-6}$) alkyl, amino ($C_{1-6}$) alkyl or carbamoyl($C_{1-6}$) alkyl; and
$R^{10}$ is hydrogen.

52. The compound according claim 1, wherein said compound is selected from the group consisting of:
a. 4-(2-Amino-4-chlorobenzyl)-3-(4-chlorophenyl)-7-iodo-3,4-dihydro-1H-benzo[e][1,4]diazepine-2,5-dione;
b. 1,3-Dihydro-4-[1-(2-amino-4-chlorophenyl)ethyl]-3-(4-chlorophenyl)-7-iodo-1,4-benzodiazepine-2,5-dione;
c. 4-[1-(2-Amino-4-chlorophenyl)ethyl]-3-(4-chlorophenyl)-7-iodo-1-[2-(4-morpholino)ethyl]-1,4-benzodiazepine-2,5-dione;
d. (3S)-4-[(R)-1-(2-Amino-4-chlorophenyl)ethyl]-3-(4-chlorophenyl)-1-[2-(2-methoxyethoxy)ethyl]-7-(propyn-1-yl)-1,4-benzodiazepine-2,5-dione hydrochloride;
e. (3S)-4-[(R)-1-(2-Amino-4-chlorophenyl)ethyl]-3-(4-chlorophenyl)-1-[2-(4-morpholino)ethyl]-7-(propyn-1-yl)-1,4-benzodiazepine-2,5-dione hydrochloride;
f. 4-[1-(2-Amino-4-chlorophenyl)ethyl]-3-(4-chlorophenyl)-7-iodo-2,3-dihydro-1H-1,4-benzodiazepin-5-one;
g. 4-[(R)-1-(2-amino-4-chlorophenyl)ethyl]-(3S)-3-(4-chlorophenyl)-7-iodo-1-[2-(2-methoxyethoxy)ethyl]-1,4-benzodiazepine-2,5-dione;
h. (3S)-4-[(R)-1-(2-Amino-4-chlorophenyl)ethyl]-3-(4-chlorophenyl)-7-iodo-1-[2-(4-morpholino)ethyl]-1,4-benzodiazepine-2,5-dione;
i. 4-[(R)-1-(2-Amino-4-chlorophenyl)-ethyl]-(3S)-3-(4-chloro-phenyl)-7-iodo-1-[3-(4-methyl-piperazin-1-yl)-propyl]-3,4-dihydro-1H-benzo[e][1,4]diazepine-2,5-dione; and
j. 5-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-yl}-pentanoic acid;
and pharmaceutically acceptable salts thereof.

53. The compound according to claim 52, wherein said compound is selected from the group consisting of:
e. (3S)-4-[(R)-1-(2-Amino-4-chlorophenyl)ethyl]-3-(4-chlorophenyl)-1-[2-(4-morpholino)ethyl]-7-(propyn-1-yl)-1,4-benzodiazepine-2,5-dione hydrochloride;
g. 4-[(R)-1-(2-amino-4-chlorophenyl)ethyl]-(3S)-3-(4chlorophenyl)-7-iodo-1-[2-(2-methoxyethoxy) ethyl]-1,4-benzodiazepine-2,5-dione;
h. (3S)-4-[(R)-1-(2-Amino-4-chlorophenyl)ethyl]-3-(4-chlorophenyl)-7-iodo-1-[2-(4-morpholino)ethyl]-1,4-benzodiazepine-2,5-dione;
i. 4-[(R)-1-(2-Amino-4-chlorophenyl)-ethyl]-(3S)-3-(4-chloro-phenyl)-7-iodo-1-[3-(4-methyl-piperazin-1-yl)-propyl]-3,4-dihydro-1H-benzo[e][1,4]diazepine-2,5-dione; and
j. 5-{(3S)-3-(4-Chlorophenyl)-4-[(R)-1-(4-chlorophenyl)-ethyl]-7-iodo-2,5-dioxo-2,3,4,5-tetrahydro-benzo[e][1,4]diazepin-1-yl}-pentanoic acid
and pharmaceutically-acceptable salts thereof.

54. A compound according to claim 1, in the form of a hydrochloride, acetate, trifluoroacetate or fumarate salt.

55. A pharmaceutical composition, comprising:
(a) a compound of claim 1, or a salt, thereof; and
(b) one or more pharmaceutically-acceptable excipients.

56. The composition of claim 55, wherein the composition is sterile.

57. The composition of claim 55, wherein said compound is present in an amount between about 0.5 and about 100 milligrams.

58. The composition of claim 55, suitable for administration by a subcutaneous, intravenous, intramuscular, intraperitoneal, buccal, or ocular route, rectally, parenterally, instrasystemically, intravaginally, topically, orally, or as an oral or nasal spray.

59. The composition of claim 55, suitable for parenteral administration, wherein said compound is present in an amount between about 0.5 and about 100 milligrams.

60. The composition of claim 55, suitable for parenteral administration, wherein said compound is present in an amount between about 0.5 and about 10 milligrams.

61. The composition of claim 55, suitable for oral administration, wherein said compound is present in an amount between about 0.5 and about 100 milligrams.

62. The composition of claim 55, suitable for oral administration, wherein said compound is present in an amount between about 25 and about 100 milligrams.

* * * * *